(12) United States Patent
Ramakrishna et al.

(10) Patent No.: US 10,596,187 B2
(45) Date of Patent: Mar. 24, 2020

(54) THERAPEUTIC COMPOSITIONS

(71) Applicants: Yale University, New Haven, CT (US); Flinders University of South Australia, South Australia (AU); Balakrishnan Siddartha Ramakrishna, Chennai (IN)

(72) Inventors: Balakrishnan Siddartha Ramakrishna, Chennai (IN); Graeme Paul Young, Victoria (AU); Ian Lewis Brown, New South Wales (AU); Henry Joseph Binder, New Haven, CT (US)

(73) Assignees: Yale University, New Haven, CT (US); Flinders University of South Australia, South Australia (AU); Balakrishnan Siddartha Ramakrishna, Chennai (IN)

( * ) Notice: Subject to any disclaimer, the term of this patent is extended or adjusted under 35 U.S.C. 154(b) by 0 days.

(21) Appl. No.: 15/034,965

(22) PCT Filed: Nov. 7, 2014

(86) PCT No.: PCT/AU2014/050338
§ 371 (c)(1),
(2) Date: May 6, 2016

(87) PCT Pub. No.: WO2015/006767
PCT Pub. Date: May 14, 2015

(65) Prior Publication Data
US 2016/0286838 A1    Oct. 6, 2016

(30) Foreign Application Priority Data

Nov. 7, 2013 (AU) .................... 2013904308

(51) Int. Cl.
*A61K 33/00* (2006.01)
*A23L 2/38* (2006.01)
(Continued)

(52) U.S. Cl.
CPC ............... *A61K 33/00* (2013.01); *A23L 2/38* (2013.01); *A23L 2/52* (2013.01); *A23L 29/212* (2016.08);
(Continued)

(58) Field of Classification Search
CPC .............................. A61K 33/00; A23L 29/212
See application file for complete search history.

(56) References Cited

U.S. PATENT DOCUMENTS

| 6,994,869 B1 * | 2/2006 | Bird .................. A23L 33/40 424/434 |
| 2008/0069861 A1 | 3/2008 | Brown et al. |
| 2008/0233260 A1 | 9/2008 | Woo et al. |

FOREIGN PATENT DOCUMENTS

| EP | 2505073 A2 | 10/2012 |
| WO | 0023517 A1 | 4/2000 |
| WO | 2006016349 A1 | 2/2006 |

OTHER PUBLICATIONS

Gancz, et al. "Adhesion of Vibrio cholerae to Granular Starches". Applied and Environmental Microbiology, Aug. 2005, p. 4850-4855. (Year: 2005).*

(Continued)

*Primary Examiner* — Jenna A Watts
(74) *Attorney, Agent, or Firm* — The Webb Law Firm

(57) ABSTRACT

Provided herein are compositions, for example: oral rehydration compositions, beverages, food items, methods and uses, which utilise resistant starch to prevent or treat dehydration, including dehydration which is caused by diarrhoea. Beverages, food items and oral rehydration solutions including a resistant starch, which are suitable for aiding in the (Continued)

maintenance and restoration of hydration levels in individuals undertaking physical activities, including sports, are also disclosed.

14 Claims, 3 Drawing Sheets

(51) Int. Cl.

| | |
|---|---|
| A61K 31/718 | (2006.01) |
| A61K 33/14 | (2006.01) |
| A61K 47/36 | (2006.01) |
| A61K 9/00 | (2006.01) |
| A23L 2/52 | (2006.01) |
| A61K 33/30 | (2006.01) |
| A61K 33/34 | (2006.01) |
| A61K 33/06 | (2006.01) |
| A23L 33/105 | (2016.01) |
| A23L 33/16 | (2016.01) |
| A23L 29/212 | (2016.01) |
| A23L 33/10 | (2016.01) |
| A23L 33/21 | (2016.01) |
| A23L 29/269 | (2016.01) |
| A23L 29/238 | (2016.01) |
| A23L 29/256 | (2016.01) |
| A23L 29/231 | (2016.01) |
| A23L 29/25 | (2016.01) |
| A23L 29/281 | (2016.01) |
| A61K 31/194 | (2006.01) |
| A61K 31/7004 | (2006.01) |

(52) U.S. Cl.
CPC ........... *A23L 29/231* (2016.08); *A23L 29/238* (2016.08); *A23L 29/25* (2016.08); *A23L 29/256* (2016.08); *A23L 29/27* (2016.08); *A23L 29/284* (2016.08); *A23L 33/10* (2016.08); *A23L 33/105* (2016.08); *A23L 33/16* (2016.08); *A23L 33/21* (2016.08); *A61K 9/0053* (2013.01); *A61K 9/0095* (2013.01); *A61K 31/194* (2013.01); *A61K 31/7004* (2013.01); *A61K 31/718* (2013.01); *A61K 33/06* (2013.01); *A61K 33/14* (2013.01); *A61K 33/30* (2013.01); *A61K 33/34* (2013.01); *A61K 47/36* (2013.01); *A23V 2002/00* (2013.01)

(56) References Cited

OTHER PUBLICATIONS

Rahim, et al. "The influence degree of substitution on the physicochemical properties of acetylated arenga starches". International Food Research Journal, 24(1): 102-107, Feb. 2017. (Year: 2017).*

Topping, et al. "Resistant starches as a vehicle for delivering health benefits to the human large bowel". Microbial Ecology in Health and Disease, 20:2, 103-108 (2008). (Year: 2008).*

Bhan, "Current Concepts in Acute Diarrhea". Indian Pediatrics. Published in 2003; 40: 463-476. (Year: 2003).*

Raghupathy, et al. "Amylase-Resistant Starch as Adjunct to Oral Rehydration Therapy in Children with Diarrhea". Journal of Pediatric Gastroenterology and Nutrition, 42: 362-368. Apr. 2006. (Year: 2006).*

Ramakrishna, et al. "Amylase-Resistant Starch Plus Oral Rehydration Solution for Cholera". The New England Journal of Medicine. Available Feb. 3, 2000. pp. 1-6. (Year: 2000).*

Clarke et al., "Acetylated High Amylose Maize Starch Improves the Efficacy of Oral Rehydration Solution in a Rat Model of Cholera," Gastroenterology, 2011, p. S-134, vol. 140, No. 5.

Barr, Effects of Dehydration on Exercise Performance, Can J Appl. Physiol., 1999, pp. 164-172, vol. 24.

Hasjim et al., Characterization of a Novel Resistant-Starch and Its Effects on Postprandial Plasma-Glucose and Insulin Responses, Cereal Chemistry, 2010, pp. 257-262, vol. 87, No. 4.

Ramakrishna et al., Amylase-Resistant Starch Plus Oral Rehydration Solution for Cholera, New England Journal of Medicine, Feb. 3, 2000, pp. 308-313, vol. 342, No. 5.

Ramakrishna et al., A Randomized Controlled Trial of Glucose versus Amylase Resistant Starch Hypo-Osmolar Oral Rehydration Solution for Adult Acute Dehydrating Diarrhea, PLoS One, Feb. 2008, pp. 1-8, vol. 3, No. 2.

Rehrer, Fluid and Electrolyte Balance in Ultra-Endurance Sport, Sports Med., 2001, pp. 701-715, vol. 31.

World Health Organization, Guidelines for Drinking-water Quality, 2011, 4th Ed.

Binder et al, "Oral Rehydration Therapy in the Second Decade of the Twenty-first Century", Curr Gastroenterol Rep, 2014, pp. 1-8, 16:376.

* cited by examiner

THERAPEUTIC COMPOSITIONS

CROSS-REFERENCE TO RELATED APPLICATIONS

This application is the United States national phase of International Application No. PCT/AU2014/050338 filed Nov. 7, 2014 and claims priority to Australian Patent Application No. 2013904308 filed on Nov. 7, 2013, the disclosures of which are hereby incorporated in their entirety by reference.

TECHNICAL FIELD

The invention discloses compositions, oral rehydration compositions, beverages, food items, methods and uses that utilise resistant starch to prevent or treat dehydration, including dehydration which is caused by diarrhoea. Beverages and oral rehydration solutions which are suitable for maintaining hydration levels in individuals undertaking physical activities, including sports, or rehydrate individuals after undertaking physical activities, are also disclosed.

BACKGROUND OF THE INVENTION

Oral rehydration solutions assist in rehydrating an individual after there has been a substantial loss of fluid, resulting in the individual experiencing dehydration. In both developing and developed countries, this dehydration is sometimes associated with benign activities such as sport. However oral rehydration solutions can also have a lifesaving role, where the cause of dehydration is not only through physical exertion or activity, but a consequence of a disease, such as excessive diarrhoea caused by, for example, rotavirus.

"Dehydration" as used herein, means a condition resulting from excessive loss of body fluid that occurs when an output of fluid exceeds a fluid intake.

Dehydration can be a significant problem. A 2% loss of body weight in fluids can diminish human performance in a number of areas (S. I. Barr, "Effects of dehydration on exercise performance", *Can. J. Appl. Physiol.*, 24, 164-172, 1999). Dehydration can occur, for example, in situations where an individual excessively sweats due to participation in a sport, or through medical conditions such as diarrhoea.

Dehydration Caused by Physical Activity

An individual taking part in intense exercise can lose approximately 1 to 3 litres of fluid in an hour (N. J. Rehrer, "Fluid and electrolyte balance in ultra-endurance sport", *Sports Med.*, 31, 701-715, 2001). This loss of fluid may be increased by exercising in a hot environment.

With regards to sports, during a football game or intensive training session Australian football league (AFL) players can lose between 1.15-3.45% of their body weight (Adelaide Football Club internal studies), due to fluid loss. This degree of fluid loss will result in a diversion of blood volume to kidneys and other vital organs with a reduced flow of fluids to muscles. An unfortunate consequence of this fluid diversion is a delay in muscle recovery for a player. Current sports drinks consumed by players during and after a game have a high glucose content, much higher than in proven rehydration solutions. Because the glucose content is high (hyperosmolar to body fluids), the sports drinks are inefficient for hydration, leading to a slower than achievable water absorption and only utilising the absorptive capacity of the small intestine and not the large intestine.

Water and salt absorption through the large intestine requires the presence of short chain fatty acids (SCFAs) which are fermented by colonic bacteria from carbohydrates. Direct ingestion of SCFAs is not an option as the SCFAs are absorbed by the small intestine before reaching the large intestine. Instead, an individual can ingest resistant starch (RS) (starches resistant to digestion), such as high amylose maize starch. These resistant starches can be found in baked foods and increase the absorption of water and salts in the large intestine in order to facilitate and enhance hydration in an individual.

Herein, beverages comprising a resistant starch, and oral rehydration compositions and solutions comprising a resistant starch are disclosed. Ingestion of these beverages, oral rehydration compositions or solutions, can enable an individual participating in a physical activity, for example a sport, to ensure they are sufficiently hydrated in order to: effectively prepare for participation in the physical activity; maintain their level of performance during the physical activity; and efficiently recover from said physical activity.

It is an aim of the present invention to provide oral rehydration compositions and solutions which show efficacy in the treatment of dehydration in individuals due to physical activity, including a sport, by formulating oral rehydration compositions which comprise starches that comprise resistant starch. These oral rehydration compositions and solutions can be consumed prior to the physical activity to ensure adequate hydration to enable an individual to participate in a physical activity, such as a sport. Alternatively, or additionally, these oral rehydration solutions can be consumed following a physical activity, such as a sport, in order to rehydrate an individual. In addition, the oral rehydration solutions can be consumed during a physical activity to ensure that an individual maintains adequate hydration for continued participation in the physical activity. These oral rehydration solutions can be consumed in combination with a food item that comprises a starch comprising a resistant starch, or an additional drink that comprises a starch comprising a resistant starch.

It is also an aim of the present invention to provide beverages that comprise a resistant starch, said beverages can be consumed be an individual before, during or after the individual undertakes a physical activity (for example a sport). The beverages can be consumed prior to the physical activity to ensure adequate hydration to enable an individual to participate in a physical activity, such as a sport. Alternatively, or additionally, the beverages can be consumed following a physical activity, such as a sport, in order to rehydrate an individual. In addition, the beverages can be consumed during a physical activity to ensure that an individual maintains adequate hydration for continued participation in the physical activity. The beverages can be consumed in combination with a food item that comprises a starch comprising a resistant starch, or an additional drink that may comprise a resistant starch.

Dehydration Caused by Diarrhoea

The World Health Organisation (WHO) states that diarrhoea is the second leading cause of death among children under five globally (The United Nations Children's Fund (UNICEF)/World Health Organization (WHO), Diarrhoea: Why children are still dying and what can be done). The diarrhoea can be caused by a number of conditions, including diseases such as cholera. According to WHO statistics only 39 percent of children suffering with diarrhoea receive the recommended treatment, which is oral rehydration therapy with continued feeding (from 2004 to present).

Currently, oral rehydration therapy consists of the delivery of a formulation that typically includes water and oral rehydration salts, the rehydration salts being a combination of sodium chloride, glucose (anhydrous), potassium chloride and trisodium citrate (dihydrate). Some rice-based oral rehydration therapies are also available.

The WHO has produced a reduced osmolarity oral rehydration solution to replace its previous standard oral rehydration solution (ORS). The recommended formulation for the reduced osmolarity oral rehydration solution is shown in Table 1. The WHO recommends a 10% tolerance with the recited values of the components recited in Table 1.

TABLE 1

WHO/UNICEF Recommendations for concentrations of components present in their reduced osmolarity oral rehydration solution.

| Element/Compound | Recommended concentration in current[a] WHO/UNICEF Reduced Osmolarity ORS/mmol/L. |
|---|---|
| Sodium | 75 |
| Chloride | 65 |
| Potassium | 20 |
| Citrate | 10 |
| Glucose | 75 |
| Total osmolarity of 245 mOsmol/L | |

[a] recommended values at 4 Sep. 2012.

Despite the WHO promoting oral rehydration solutions, these solutions have not achieved the wide-spread use that was initially expected. Although this may be due in considerable part to a lack of knowledge or appreciation of the effects of oral rehydration solutions, those in the developing world have been reluctant to use them as there is not a palpable effect in reducing diarrhoea despite evidence that they do provide a benefit, to a limited degree, in reducing the risk of dehydration and, in some cases, reducing the risk of death due to dehydration. Therefore, improved formulations need to be devised in order for the communities who need them to take them seriously and utilise them in the treatment of dehydration.

It is an aim of the present invention to provide oral rehydration compositions which show efficacy in the treatment of dehydration, including dehydration caused by diarrhoea, by formulating oral rehydration compositions which comprise a starch that comprises a resistant starch.

SUMMARY OF THE INVENTION

Disclosed herein are oral rehydration compositions which comprise: a starch comprising a resistant starch, a salt composition and a suspending agent.

Also disclosed herein are oral rehydration compositions which comprise: (a) a starch comprising a resistant starch, starch derived materials, (for example chemically treated starch materials), other starches or starch containing materials, or dietary fibre or combinations thereof; (b) a salt composition; and (c) a suspending agent.

Also disclosed herein is an oral rehydration composition which has been combined with an aqueous solution, preferably water, more preferably drinking water, to produce an aqueous composition that displays efficacy in the treatment of dehydration caused by a physical activity and/or dehydration which is a result of a disease.

Herein, the water which is to be combined with an oral rehydration composition of the invention is preferably "drinking water" as defined by the World Health Organisation (World Health Organization, Guidelines for Drinking-water Quality, fourth edition, 2011).

The present inventors have identified oral rehydration compositions which comprise a starch comprising a resistant starch and a suspending agent, which provide a treatment for dehydration caused by diarrhoea, wherein the diarrhoea is caused by diseases, including, but not limited to: bacterial and viral induced diarrhoea, travellers' diarrhoea, radiation induced diarrhoea, and also diarrhoea which is a result of weaning in both humans and animals.

The present inventors have also identified oral rehydration compositions which comprise a starch comprising a resistant starch and a suspending agent, which provide a treatment for dehydration caused by physical activity, such as a sport.

Furthermore, the inventors have identified the use of resistant starch in beverages that can be consumed before, during or after an individual takes part in a physical activity, such as a sport. Where the beverage is consumed prior to the physical activity, colonic bacteria can ferment the resistant starch in order to produce SCFAs by the action of colonic bacteria, which are beneficial in maintaining hydration in the hydration, or rehydrating the individual.

"Physical activity" is defined by the WHO as any bodily movement produced by skeletal muscles that require energy to be expended. The physical activity may be an activity, such as a sport, performed by a human. Alternatively, the physical activity may be an activity, such as a sport, performed by an animal.

"Sports" would be understood to be an activity pursued for exercise or pleasure governed by a set of rules or customs which involves a degree of physical exertion and skill wherein either individuals or teams compete against one another. Examples include, but are not limited to: athletics (including running), football (including soccer, American football and Australian football), rugby, tennis, swimming, cricket, basketball, netball, golf, cycling, badminton, volleyball, squash, ice hockey, baseball, skateboarding, surfing, skiing, snowboarding, martials arts, wrestling, gymnastics, hockey, rowing, motor racing, skating and boxing. Sports encompassing animals include, but are not limited to: horse racing and greyhound racing.

With oral rehydration compositions which are to be used in the developing or developed world, the components of these compositions should ideally be in a form that is easy to transport and store. In addition, it is advantageous if the components readily mix with water, although the components do not necessarily need to be fully soluble in the water.

In one embodiment, the current invention provides oral rehydration compositions wherein the components, including, for example: a starch comprising a resistant starch, a salt composition and a suspending agent, are in the form of solids, including, for example, powders, which can be introduced to water. The resulting aqueous composition can be ingested and used to treat dehydration, or conditions that might lead to dehydration, in an individual.

The inventors have importantly identified that for the oral rehydration compositions of the invention to be effective in the treatment of dehydration when they are combined in water and ingested by an individual, a suspending agent must be present. This suspending agent prevents the starch (es), including a starch comprising a resistant starch, and/or dietary fibre, as disclosed herein, from gravitating to the bottom of a solution once the oral rehydration compositions are combined in a solution, for example water, preferably drinking water. In addition, the suspending agent also plays an important role in improving the stability, the efficacy and palatability of the oral rehydration composition. The use of a suspending agent facilitates the ingestion of the starch(es) (and/or starch derived material and/or dietary fibre), and helps to ensure that they are consumed along with the other components of the oral rehydration composition.

It is also an aim of the present invention to provide compositions, for example oral rehydration compositions, which can be commercially produced in a manner which is economically viable for distribution in both the developing and developed world. Furthermore, it is beneficial if the oral rehydration compositions as disclosed herein, are able to be transported and stored for distribution in developing and developed countries, without any detrimental effects or reduced efficacy occurring when the components of the oral rehydration compositions are combined in water and distributed to individuals for the treatment, or prevention, of dehydration.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

In a first aspect, the invention provides an oral rehydration composition comprising:
  a salt composition;
  at least one substance selected from the group consisting of:
    a class V high amylose maize starch;
    a class VI high amylose maize starch;
    a class VII high amylose maize starch
    a class VIII high amylose maize starch;
    a class IX high amylose maize starch;
    a class X high amylose maize starch;
    a type IV resistant starch;
    a type V resistant starch; and
    combinations thereof;
  a suspending agent in an amount effective to suspend the at least one substance in water; and
  optionally one or more of:
    glucose;
    water soluble salts of zinc, magnesium or copper;
    sodium bicarbonate; or
    combinations thereof.

In a second aspect, the invention provides an oral rehydration composition consisting essentially of:
  a salt composition;
  a starch comprising a resistant starch;
  a suspending agent in an amount effective to suspend the starch comprising a resistant starch in water; and
  optionally one or more of:
    water soluble salts of zinc, magnesium or copper;
    sodium bicarbonate; and
    combinations thereof.

In a third aspect, the invention provides an aqueous composition comprising an oral rehydration composition according to the first or second aspect, and water.

In a fourth aspect the invention provides an aqueous composition comprising an oral rehydration composition according to the first or second aspect, and water, wherein the aqueous composition rehydrates an individual affected by dehydration.

In a fifth aspect, the invention provides a method of rehydrating an individual suffering from dehydration, the method comprising a step of administering an effective amount of an oral rehydration composition that comprises:
  a salt composition;
  a starch comprising a resistant starch;
  a suspending agent in an amount effective to suspend the starch comprising a
  resistant starch; and
  optionally one or more of:
    glucose;
    water soluble salts of zinc, magnesium or copper;
    sodium bicarbonate; or
    combinations thereof.

In a sixth aspect, the invention provides a use of an oral rehydration composition to rehydrate an individual suffering from dehydration, the oral rehydration composition comprising:
  a salt composition;
  a starch comprising a resistant starch;
  a suspending agent in an amount effective to suspend the starch comprising a
  resistant starch; and
  optionally one or more of:
    glucose;
    water soluble salts of zinc, magnesium or copper;
    sodium bicarbonate; or
    combinations thereof.

In a seventh aspect, the invention provides a beverage comprising a resistant starch selected from the group consisting of:
  a class V high amylose maize starch;
  a class VI high amylose maize starch;
  a class VII high amylose maize starch
  a class VIII high amylose maize starch;
  a class IX high amylose maize starch;
  a class X high amylose maize starch;
  a type IV resistant starch;
  a type V resistant starch; and
  combinations thereof,
  wherein the beverage is formulated for an individual to consume before, during or after the individual engages in a physical activity.

In an eighth aspect, the invention provides a beverage comprising an oral rehydration composition according to the first or second aspect that is formulated for an individual to consume before, during or after the individual engages in a physical activity.

In a ninth aspect, the invention provides a food item comprising a resistant starch selected from the group consisting of:
  a class V high amylose maize starch;
  a class VI high amylose maize starch;
  a class VII high amylose maize starch
  a class VIII high amylose maize starch;
  a class IX high amylose maize starch;
  a class X high amylose maize starch;
  a type IV resistant starch;
  a type V resistant starch; and
  combinations thereof,
  wherein the food item is formulated for an individual to consume before, during or after the individual engages in a physical activity.

In a tenth aspect, the invention provides a use of a starch comprising a resistant starch selected from the group consisting of:
  a class V high amylose maize starch;
  a class VI high amylose maize starch;
  a class VII high amylose maize starch
  a class VIII high amylose maize starch;
  a class IX high amylose maize starch;

a class X high amylose maize starch;
a type IV resistant starch;
a type V resistant starch; and
combinations thereof.
in a composition to maintain hydration in an individual and/or rehydrate the individual.

DESCRIPTION OF DRAWINGS

Whilst it will be appreciated that a variety of embodiments of the invention may be utilised, in the following, we describe a number of examples of the invention with reference to the following drawings.

DETAILED DESCRIPTION OF THE INVENTION

Figure 1:
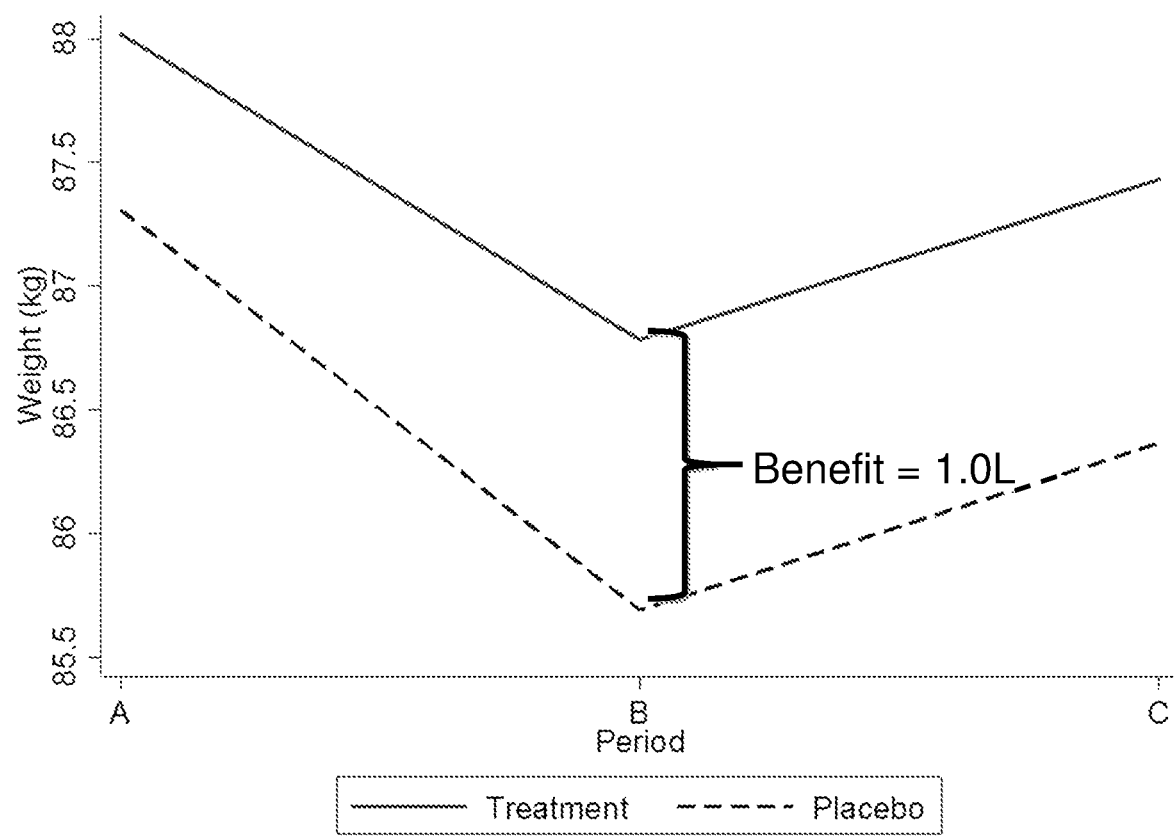
FIG. 1 shows a comparison in the mean weight of Australian football players during a control week and a week consuming compositions of the invention, at three time periods (A—before a training session; B—at the end of a training session; and C—1 hour after training has finished)

In one embodiment the compositions of the invention are oral rehydration compositions which comprise the following components: a starch comprising a resistant starch, a salt composition and a suspending agent. These components can be in the form of dry solids, including powders, which can be added to a solution, for example a solution of water, a protein shake, a milk based beverage or a fruit juice. The resulting solutions can then be ingested by an individual to treat, or prevent, dehydration.

In some embodiments of the invention the starch comprising a resistant starch, salt composition and the suspending agent, are combined in a single dry solids composition, including a dry powder composition, which can be introduced into water, preferably drinking water. The resulting solutions can then be ingested by an individual to treat dehydration.

In some embodiments of the invention the starch comprising a resistant starch, salt composition and suspending agent are separated in to more than one dry solid composition, which may be dry powder compositions.

In some embodiments of the invention, the starch comprising a resistant starch, salt composition and suspending agent, can be stored as dry solids, for example dry powders, in a single container such as a sachet, or multiple containers, for example in multiple sachets, prior to use and ingestion. For example, the starch comprising a resistant starch and the suspending agent is stored in one sachet and the salt composition is stored in another sachet. The contents of the two sachets in this example can be combined in water, preferably drinking water, wherein the resulting aqueous composition can then be ingested by an individual to treat dehydration.

Herein, the components of the oral rehydration compositions are disclosed in quantities in ranges of, for example, "g/L" or "mg/L". These values disclose the quantity of an element or compound that would be present in an aqueous composition produced by combining an oral rehydration composition of the invention with 1 L of water.

Suspending Agent

Herein "suspending agent" refers to a compound that is present in a composition of the invention, such as an oral rehydration composition of the invention, in an amount that is effective to suspend the starch comprising a resistant starch (or other starch and starch containing material, or dietary fibre), when the composition is added to a solution, preferably water, more preferably drinking water. The suspending agent is introduced so that it enables the starch comprising a resistant starch, or other starch and starch containing material, or dietary fibre, to be suspended in solution for a period of time and not merely gravitate to the bottom of a container holding the solution. The incorporation of a suspending agent helps to ensure that the starch comprising a resistant starch (or other starch, starch containing material, or dietary fibre), is ingested by an individual consuming the composition.

The current inventors have identified that in order for the starch comprising a resistant starch (or other starch, starch containing material, or dietary fibre if present), to remain suspended in solution, for example water or, more preferably drinking water, a compound which acts as a suspending agent should be present. The inventors also found that, surprisingly, not all compounds which would theoretically act as a suspending agent, that are known to a person skilled in the art, are appropriate for the present invention. The starch comprising a resistant starch (or other starch, starch containing material, or dietary fibre), needs to be suspended when a composition of the invention is combined with a solution, for example drinking water, to ensure that all the components of the composition are ingested by an individual to treat dehydration and provide the physiological benefits which includes increasing or maintaining an individual's hydration level.

In one embodiment, the suspending agent can be a gum or a gum derivative and can be selected from the group comprising, but not limited to:
  xanthan gum (including, for example, Grindsted® Xanthan Clear Easy A21191),
  guar gum,
  gelatine (derived from animal, fish, etc.),
  carrageenan (iota, lambda, kappa) (derived from seaweed),
  agar,
  alginate,
  locust bean gum,
  gum arabic,
  cellulose (including, for example, methyl-, carboxy methyl- and hydroxylpropyl methyl-cellulose),
  gellan,
  pectin, and
  combinations thereof.

In one embodiment, the suspending agent is xanthan gum.
In another embodiment, the suspending agent is guar gum.
In another embodiment, the suspending agent is agar.
In another embodiment, the suspending agent is alginate.
In another embodiment, the suspending agent is carrageenan.
In another embodiment, the suspending agent is cellulose (including, for example, methyl-, carboxy methyl- and hydroxyl propyl methyl-cellulose).
In another embodiment, the suspending agent is gelatine.

In another embodiment, the suspending agent is gellan.

In another embodiment, the suspending agent is gum arabic.

In yet another embodiment, the suspending agent is locust bean gum.

In yet another embodiment, the suspending agent is pectin.

In yet another embodiment, the suspending agent is a mixture of at least two compounds defined herein as a suspending agent.

A gum or gum derivative used herein as a suspending agent has the ability to rapidly rehydrate and have an appropriate viscosity, excellent palatability and provide the required dispersion and suspension of the starch comprising a resistant starch.

Herein, the suspending agent is disclosed in quantities in ranges of "g/L". These values disclose the quantity of the suspending agent that would be present in an aqueous composition produced by combining an oral rehydration composition of the invention with 1 L of water.

In another embodiment the suspending agent is xanthan gum, wherein the xanthan gum is present in a composition of the invention in an amount in a range of from about 0.5 g/L to about 5.0 g/L, preferably in an amount in a range from about 1 g/L to about 2.5 g/L, more preferably in an amount from about 1.5 g/L to about 2.25 g/L. Exemplified ranges include but are not limited to: about 0.5 g/L to about 4.5 g/L; about 0.5 g/L to about 4.0 g/L; about 0.5 g/L to about 3.5 g/L; about 0.5 g/L to about 3.0 g/L; about 0.5 g/L to about 2.5 g/L; about 0.5 g/L to about 2.0 g/L; about 0.5 g/L to about 1.5 g/L; about 0.5 g/L to about 1.0 g/L; about 1.0 g/L to about 5.0 g/L; about 1.5 g/L to about 5.0 g/L; about 2.0 g/L to about 5.0 g/L; about 2.5 g/L to about 5.0 g/L; about 3.0 g/L to about 5.0 g/L; about 3.5 g/L to about 5.0 g/L; about 4.0 g/L to about 5.0 g/L; or 4.5 g/L to about 5.0 g/L.

In another embodiment the suspending agent is guar gum, wherein the guar gum is present in a composition of the invention in an amount in a range of from about 1.0 g/L to about 10.0 g/L, preferably in an amount in a range from about 2.0 g/L to about 6.0 g/L, more preferably in an amount from about 3.0 g/L to about 5.0 g/L. Exemplified ranges include but are not limited to: about 1.0 g/L to about 10.0 g/L; about 1.5 g/L to about 10.0 g/L; about 2.0 g/L to about 10.0 g/L; about 2.5 g/L to about 10.0 g/L; about 3.0 g/L to about 10.0 g/L; about 3.5 g/L to about 10.0 g/L; about 4.0 g/L to about 10.0 g/L; about 4.5 g/L to about 10.0 g/L; about 5.0 g/L to about 10.0 g/L; about 5.5 g/L to about 10.0 g/L; about 6.0 g/L to about 10.0 g/L; about 6.5 g/L to about 10.0 g/L; about 7.0 g/L to about 10.0 g/L; about 7.5 g/L to about 10.0 g/L; about 8.0 g/L to about 10.0 g/L; about 8.5 g/L to about 10.0 g/L; about 9.0 g/L to about 10.0 g/L; about 9.5 g/L to about 10.0 g/L; about 1.0 g/L to about 9.5 g/L; about 1.0 g/L to about 9.0 g/L; about 1.0 g/L to about 8.5 g/L; about 1.0 g/L to about 8.0 g/L; about 1.0 g/L to about 7.5 g/L; about 1.0 g/L to about 7.0 g/L; about 1.0 g/L to about 6.5 g/L; about 1.0 g/L to about 6.0 g/L; about 1.0 g/L to about 5.5 g/L; about 1.0 g/L to about 5.0 g/L; about 1.0 g/L to about 4.5 g/L; about 1.0 g/L to about 4.0 g/L; about 1.0 g/L to about 3.5 g/L; about 1.0 g/L to about 3.0 g/L; about 1.0 g/L to about 2.5 g/L; about 1.0 g/L to about 2.0 g/L; or about 1.0 g/L to about 1.5 g/L.

In another embodiment the suspending agent is agar, wherein the agar is present in a composition of the invention in an amount in a range of from about 3 g/L to about 15 g/L, preferably in an amount in a range from about 4 g/L to about 12 g/L, more preferably in an amount from about 5.0 g/L to about 10.0 g/L. Exemplified ranges include but are not limited to: about 3 g/L to about 15 g/L; 3.5 g/L to about 15 g/L; 4.0 g/L to about 15 g/L; 4.5 g/L to about 15 g/L; 5 g/L to about 15 g/L; 5.5 g/L to about 15 g/L; about 6 g/L to about 15 g/L; about 6.5 g/L to about 15 g/L; about 7 g/L to about 15 g/L; about 7.5 g/L to about 15 g/L; about 8 g/L to about 15 g/L; about 8.5 g/L to about 15 g/L; about 9 g/L to about 15 g/L; about 9.5 g/L to about 15 g/L; about 10 g/L to about 15 g/L; about 10.5 g/L to about 15 g/L; about 11 g/L to about 15 g/L; about 11.5 g/L to about 15 g/L; about 12 g/L to about 15 g/L; about 12.5 g/L to about 15 g/L; about 13 g/L to about 15 g/L; about 13.5 g/L to about 15 g/L; about 14 g/L to about 15 g/L; about 14.5 g/L to about 15 g/L; about 3 g/L to about 14.5 g/L; about 3 g/L to about 14 g/L; about 3 g/L to about 13.5 g/L; about 3 g/L to about 13 g/L; about 3 g/L to about 12.5 g/L; about 3 g/L to about 12 g/L; about 3 g/L to about 11.5 g/L; about 3 g/L to about 11 g/L; about 3 g/L to about 10.5 g/L; about 3 g/L to about 10 g/L; about 3 g/L to about 9.5 g/L; about 3 g/L to about 9.0 g/L; about 3 g/L to about 8.5 g/L; about 3 g/L to about 8.0 g/L; about 3 g/L to about 7.5 g/L; about 3 g/L to about 7.0 g/L; about 3 g/L to about 6.5 g/L; about 3 g/L to about 6.0 g/L; about 3 g/L to about 5.5 g/L; about 3 g/L to about 5 g/L; about 3 g/L to about 4.5 g/L; about 3 g/L to about 4.0 g/L; or about 3 g/L to about 3.5 g/L.

In another embodiment the suspending agent is alginate, wherein the alginate is present in a composition of the invention in an amount in a range of from about 3 g/L to about 15 g/L, preferably in an amount in a range from about 4 g/L to about 12 g/L, more preferably in an amount from about 5.0 g/L to about 10.0 g/L. Exemplified ranges include but are not limited to: about 3 g/L to about 15 g/L; 3.5 g/L to about 15 g/L; 4.0 g/L to about 15 g/L; 4.5 g/L to about 15 g/L; 5 g/L to about 15 g/L; 5.5 g/L to about 15 g/L; about 6 g/L to about 15 g/L; about 6.5 g/L to about 15 g/L; about 7 g/L to about 15 g/L; about 7.5 g/L to about 15 g/L; about 8 g/L to about 15 g/L; about 8.5 g/L to about 15 g/L; about 9 g/L to about 15 g/L; about 9.5 g/L to about 15 g/L; about 10 g/L to about 15 g/L; about 10.5 g/L to about 15 g/L; about 11 g/L to about 15 g/L; about 11.5 g/L to about 15 g/L; about 12 g/L to about 15 g/L; about 12.5 g/L to about 15 g/L; about 13 g/L to about 15 g/L; about 13.5 g/L to about 15 g/L; about 14 g/L to about 15 g/L; about 14.5 g/L to about 15 g/L; about 3 g/L to about 14.5 g/L; about 3 g/L to about 14 g/L; about 3 g/L to about 13.5 g/L; about 3 g/L to about 13 g/L; about 3 g/L to about 12.5 g/L; about 3 g/L to about 12 g/L; about 3 g/L to about 11.5 g/L; about 3 g/L to about 11 g/L; about 3 g/L to about 10.5 g/L; about 3 g/L to about 10 g/L; about 3 g/L to about 9.5 g/L; about 3 g/L to about 9.0 g/L; about 3 g/L to about 8.5 g/L; about 3 g/L to about 8.0 g/L; about 3 g/L to about 7.5 g/L; about 3 g/L to about 7.0 g/L; about 3 g/L to about 6.5 g/L; about 3 g/L to about 6.0 g/L; about 3 g/L to about 5.5 g/L; about 3 g/L to about 5 g/L; about 3 g/L to about 4.5 g/L; about 3 g/L to about 4.0 g/L; or about 3 g/L to about 3.5 g/L.

In another embodiment the suspending agent is carrageenan, wherein the carrageenan is present in a composition of the invention in an amount in a range of from about 5 g/L to about 15 g/L, preferably in an amount in a range from about 6 g/L to about 12 g/L, more preferably in an amount from about 7.5 g/L to about 10.0 g/L. Exemplified ranges include but are not limited to: about 5.5 g/L to about 15 g/L; about 6 g/L to about 15 g/L; about 6.5 g/L to about 15 g/L; about 7 g/L to about 15 g/L; about 7.5 g/L to about 15 g/L; about 8 g/L to about 15 g/L; about 8.5 g/L to about 15 g/L; about 9 g/L to about 15 g/L; about 9.5 g/L to about 15 g/L; about 10 g/L to about 15 g/L; about 10.5 g/L to about 15 g/L; about 11 g/L to about 15 g/L; about 11.5 g/L to about 15 g/L;

about 12 g/L to about 15 g/L; about 12.5 g/L to about 15 g/L; about 13 g/L to about 15 g/L; about 13.5 g/L to about 15 g/L; about 14 g/L to about 15 g/L; about 14.5 g/L to about 15 g/L; about 5 g/L to about 14.5 g/L; about 5 g/L to about 14 g/L; about 5 g/L to about 13.5 g/L; about 5 g/L to about 13 g/L; about 5 g/L to about 12.5 g/L; about 5 g/L to about 12 g/L; about 5 g/L to about 11.5 g/L; about 5 g/L to about 11 g/L; about 5 g/L to about 10.5 g/L; about 5 g/L to about 10 g/L; about 5 g/L to about 9.5 g/L; about 5 g/L to about 9.0 g/L; about 5 g/L to about 8.5 g/L; about 5 g/L to about 8.0 g/L; about 5 g/L to about 7.5 g/L; about 5 g/L to about 7.0 g/L; about 5 g/L to about 6.5 g/L; about 5 g/L to about 6.0 g/L; or about 5 g/L to about 5.5 g/L.

In another embodiment the suspending agent is cellulose (including methyl-, carboxy methyl-, and hydroxylpropyl methyl-cellulose), wherein the cellulose (including methyl-, carboxy methyl-, and hydroxylpropyl methyl-cellulose), is present in a composition of the invention in an amount in a range of from about 5 g/L to about 20 g/L, preferably in an amount in a range from about 6 g/L to about 15 g/L, more preferably in an amount from about 7.5 g/L to about 12.0 g/L. Exemplified ranges include but are not limited to: about 5.5 g/L to about 20 g/L; about 6 g/L to about 20 g/L; about 6.5 g/L to about 20 g/L; about 7 g/L to about 20 g/L; about 7.5 g/L to about 20 g/L; about 8 g/L to about 20 g/L; about 8.5 g/L to about 20 g/L; about 9 g/L to about 20 g/L; about 9.5 g/L to about 20 g/L; about 10 g/L to about 20 g/L; about 10.5 g/L to about 20 g/L; about 11 g/L to about 20 g/L; about 11.5 g/L to about 20 g/L; about 12 g/L to about 20 g/L; about 12.5 g/L to about 20 g/L; about 13 g/L to about 20 g/L; about 13.5 g/L to about 20 g/L; about 14 g/L to about 20 g/L; about 14.5 g/L to about 20 g/L; about 15 g/L to about 20 g/L; about 15.5 g/L to about 20 g/L; about 16 g/L to about 20 g/L; about 16.5 g/L to about 20 g/L; about 17 g/L to about 20 g/L; about 17.5 g/L to about 20 g/L; about 18 g/L to about 20 g/L; about 18.5 g/L to about 20 g/L; about 19 g/L to about 20 g/L; about 19.5 g/L to about 20 g/L; about 5 g/L to about 19.5 g/L; about 5 g/L to about 19 g/L; about 5 g/L to about 18.5 g/L; about 5 g/L to about 18 g/L; about 5 g/L to about 17.5 g/L; about 5 g/L to about 17 g/L; about 5 g/L to about 16.5 g/L; about 5 g/L to about 16 g/L; about 5 g/L to about 15.5 g/L; about 5 g/L to about 15 g/L; about 5 g/L to about 14.5 g/L; about 5 g/L to about 14 g/L; about 5 g/L to about 13.5 g/L; about 5 g/L to about 13 g/L; about 5 g/L to about 12.5 g/L; about 5 g/L to about 12 g/L; about 5 g/L to about 11.5 g/L; about 5 g/L to about 11 g/L; about 5 g/L to about 10.5 g/L; about 5 g/L to about 10 g/L; about 5 g/L to about 9.5 g/L; about 5 g/L to about 9.0 g/L; about 5 g/L to about 8.5 g/L; about 5 g/L to about 8.0 g/L; about 5 g/L to about 7.5 g/L; about 5 g/L to about 7.0 g/L; about 5 g/L to about 6.5 g/L; about 5 g/L to about 6.0 g/L; or about 5 g/L to about 5.5 g/L.

In another embodiment the suspending agent is gelatine, wherein the gelatine is present in a composition of the invention in an amount in a range of from about 5 g/L to about 20 g/L, preferably in an amount in a range from about 7 g/L to about 17.5 g/L, more preferably in an amount from about 10.0 g/L to about 15.0 g/L. Exemplified ranges include but are not limited to: about 5.5 g/L to about 20 g/L; about 6 g/L to about 20 g/L; about 6.5 g/L to about 20 g/L; about 7 g/L to about 20 g/L; about 7.5 g/L to about 20 g/L; about 8 g/L to about 20 g/L; about 8.5 g/L to about 20 g/L; about 9 g/L to about 20 g/L; about 9.5 g/L to about 20 g/L; about 10 g/L to about 20 g/L; about 10.5 g/L to about 20 g/L; about 11 g/L to about 20 g/L; about 11.5 g/L to about 20 g/L; about 12 g/L to about 20 g/L; about 12.5 g/L to about 20 g/L; about 13 g/L to about 20 g/L; about 13.5 g/L to about 20 g/L; about 14 g/L to about 20 g/L; about 14.5 g/L to about 20 g/L; about 15 g/L to about 20 g/L; about 15.5 g/L to about 20 g/L; about 16 g/L to about 20 g/L; about 16.5 g/L to about 20 g/L; about 17 g/L to about 20 g/L; about 17.5 g/L to about 20 g/L; about 18 g/L to about 20 g/L; about 18.5 g/L to about 20 g/L; about 19 g/L to about 20 g/L; about 19.5 g/L to about 20 g/L; about 5 g/L to about 19.5 g/L; about 5 g/L to about 19 g/L; about 5 g/L to about 18.5 g/L; about 5 g/L to about 18 g/L; about 5 g/L to about 17.5 g/L; about 5 g/L to about 17 g/L; about 5 g/L to about 16.5 g/L; about 5 g/L to about 16 g/L; about 5 g/L to about 15.5 g/L; about 5 g/L to about 15 g/L; about 5 g/L to about 14.5 g/L; about 5 g/L to about 14 g/L; about 5 g/L to about 13.5 g/L; about 5 g/L to about 13 g/L; about 5 g/L to about 12.5 g/L; about 5 g/L to about 12 g/L; about 5 g/L to about 11.5 g/L; about 5 g/L to about 11 g/L; about 5 g/L to about 10.5 g/L; about 5 g/L to about 10 g/L; about 5 g/L to about 9.5 g/L; about 5 g/L to about 9.0 g/L; about 5 g/L to about 8.5 g/L; about 5 g/L to about 8.0 g/L; about 5 g/L to about 7.5 g/L; about 5 g/L to about 7.0 g/L; about 5 g/L to about 6.5 g/L; about 5 g/L to about 6.0 g/L; or about 5 g/L to about 5.5 g/L.

In another embodiment the suspending agent is gellan, wherein the gellan is present in a composition of the invention in an amount in a range of from about 2 g/L to about 15 g/L, preferably in an amount in a range from about 4 g/L to about 12 g/L, more preferably in an amount from about 5.0 g/L to about 10.0 g/L. Exemplified ranges include but are not limited to: about 2.5 g/L to about 15 g/L; about 3 g/L to about 15 g/L; 3.5 g/L to about 15 g/L; 4.0 g/L to about 15 g/L; 4.5 g/L to about 15 g/L; 5 g/L to about 15 g/L; 5.5 g/L to about 15 g/L; about 6 g/L to about 15 g/L; about 6.5 g/L to about 15 g/L; about 7 g/L to about 15 g/L; about 7.5 g/L to about 15 g/L; about 8 g/L to about 15 g/L; about 8.5 g/L to about 15 g/L; about 9 g/L to about 15 g/L; about 9.5 g/L to about 15 g/L; about 10 g/L to about 15 g/L; about 10.5 g/L to about 15 g/L; about 11 g/L to about 15 g/L; about 11.5 g/L to about 15 g/L; about 12 g/L to about 15 g/L; about 12.5 g/L to about 15 g/L; about 13 g/L to about 15 g/L; about 13.5 g/L to about 15 g/L; about 14 g/L to about 15 g/L; about 14.5 g/L to about 15 g/L; about 2 g/L to about 14.5 g/L; about 2 g/L to about 14 g/L; about 2 g/L to about 13.5 g/L; about 2 g/L to about 13 g/L; about 2 g/L to about 12.5 g/L; about 2 g/L to about 12 g/L; about 2 g/L to about 11.5 g/L; about 2 g/L to about 11 g/L; about 2 g/L to about 10.5 g/L; about 2 g/L to about 10 g/L; about 2 g/L to about 9.5 g/L; about 2 g/L to about 9.0 g/L; about 2 g/L to about 8.5 g/L; about 2 g/L to about 8.0 g/L; about 2 g/L to about 7.5 g/L; about 2 g/L to about 7.0 g/L; about 2 g/L to about 6.5 g/L; about 2 g/L to about 6.0 g/L; about 2 g/L to about 5.5 g/L; about 2 g/L to about 5 g/L; about 2 g/L to about 4.5 g/L; about 2 g/L to about 4.0 g/L; about 2 g/L to about 3.5; about 2 g/L to about 3.0 g/L; or about 2 g/L to about 2.5 g/L.

In another embodiment the suspending agent is gum arabic, wherein the gum arabic is present in a composition of the invention in an amount in a range of from about 5 g/L to about 25 g/L, preferably in an amount in a range from about 7 g/L to about 20 g/L, more preferably in an amount from about 10.0 g/L to about 20.0 g/L. Exemplified ranges include but are not limited to: about 5.5 g/L to about 25 g/L; about 6 g/L to about 25 g/L; about 6.5 g/L to about 25 g/L; about 7 g/L to about 25 g/L; about 7.5 g/L to about 25 g/L; about 8 g/L to about 25 g/L; about 8.5 g/L to about 25 g/L; about 9 g/L to about 25 g/L; about 9.5 g/L to about 25 g/L; about 10 g/L to about 25 g/L; about 10.5 g/L to about 25 g/L; about 11 g/L to about 25 g/L; about 11.5 g/L to about 25 g/L; about 12 g/L to about 25 g/L; about 12.5 g/L to about 25 g/L; about 13 g/L to about 25 g/L; about 13.5 g/L to about 25 g/L; about 14 g/L to about 25 g/L; about 14.5 g/L to about 25 g/L;

about 15 g/L to about 25 g/L; about 15.5 g/L to about 25 g/L; about 16 g/L to about 25 g/L; about 16.5 g/L to about 25 g/L; about 17 g/L to about 25 g/L; about 17.5 g/L to about 25 g/L; about 18 g/L to about 25 g/L; about 18.5 g/L to about 25 g/L; about 19 g/L to about 25 g/L; about 19.5 g/L to about 25 g/L; about 20 g/L to about 25 g/L; about 20.5 g/L to about 25 g/L; about 21 g/L to about 25 g/L; about 21.5 g/L to about 25 g/L; about 22 g/L to about 25 g/L; about 22.5 g/L to about 25 g/L; about 23 g/L to about 25 g/L; about 23.5 g/L to about 25 g/L; about 24 g/L to about 25 g/L; about 24.5 g/L to about 25 g/L; about 5 g/L to about 24.5 g/L; about 5 g/L to about 24 g/L; about 5 g/L to about 23.5 g/L; about 5 g/L to about 23 g/L; about 5 g/L to about 22.5 g/L; about 5 g/L to about 22 g/L; about 5 g/L to about 21.5 g/L; about 5 g/L to about 21 g/L; about 5 g/L to about 20.5 g/L; about 5 g/L to about 20 g/L; about 5 g/L to about 19.5 g/L; about 5 g/L to about 19 g/L; about 5 g/L to about 18.5 g/L; about 5 g/L to about 18 g/L; about 5 g/L to about 17.5 g/L; about 5 g/L to about 17 g/L; about 5 g/L to about 16.5 g/L; about 5 g/L to about 16 g/L; about 5 g/L to about 15.5 g/L; about 5 g/L to about 15 g/L; about 5 g/L to about 14.5 g/L; about 5 g/L to about 14 g/L; about 5 g/L to about 13.5 g/L; about 5 g/L to about 13 g/L; about 5 g/L to about 12.5 g/L; about 5 g/L to about 12 g/L; about 5 g/L to about 11.5 g/L; about 5 g/L to about 11 g/L; about 5 g/L to about 10.5 g/L; about 5 g/L to about 10 g/L; about 5 g/L to about 9.5 g/L; about 5 g/L to about 9.0 g/L; about 5 g/L to about 8.5 g/L; about 5 g/L to about 8.0 g/L; about 5 g/L to about 7.5 g/L; about 5 g/L to about 7.0 g/L; about 5 g/L to about 6.5 g/L; about 5 g/L to about 6.0 g/L; or about 5 g/L to about 5.5 g/L.

In another embodiment the suspending agent is locust bean gum, wherein the locust bean gum is present in a composition of the invention in an amount in a range of from about 3 g/L to about 15 g/L, preferably in an amount in a range from about 4 g/L to about 12 g/L, more preferably in an amount from about 5.0 g/L to about 10.0 g/L. Exemplified ranges include but are not limited to: about 3 g/L to about 15 g/L; 3.5 g/L to about 15 g/L; 4.0 g/L to about 15 g/L; 4.5 g/L to about 15 g/L; 5 g/L to about 15 g/L; 5.5 g/L to about 15 g/L; about 6 g/L to about 15 g/L; about 6.5 g/L to about 15 g/L; about 7 g/L to about 15 g/L; about 7.5 g/L to about 15 g/L; about 8 g/L to about 15 g/L; about 8.5 g/L to about 15 g/L; about 9 g/L to about 15 g/L; about 9.5 g/L to about 15 g/L; about 10 g/L to about 15 g/L; about 10.5 g/L to about 15 g/L; about 11 g/L to about 15 g/L; about 11.5 g/L to about 15 g/L; about 12 g/L to about 15 g/L; about 12.5 g/L to about 15 g/L; about 13 g/L to about 15 g/L; about 13.5 g/L to about 15 g/L; about 14 g/L to about 15 g/L; about 14.5 g/L to about 15 g/L; about 3 g/L to about 14.5 g/L; about 3 g/L to about 14 g/L; about 3 g/L to about 13.5 g/L; about 3 g/L to about 13 g/L; about 3 g/L to about 12.5 g/L; about 3 g/L to about 12 g/L; about 3 g/L to about 11.5 g/L; about 3 g/L to about 11 g/L; about 3 g/L to about 10.5 g/L; about 3 g/L to about 10 g/L; about 3 g/L to about 9.5 g/L; about 3 g/L to about 9.0 g/L; about 3 g/L to about 8.5 g/L; about 3 g/L to about 8.0 g/L; about 3 g/L to about 7.5 g/L; about 3 g/L to about 7.0 g/L; about 3 g/L to about 6.5 g/L; about 3 g/L to about 6.0 g/L; about 3 g/L to about 5.5 g/L; about 3 g/L to about 5 g/L; about 3 g/L to about 4.5 g/L; about 3 g/L to about 4.0 g/L; or about 3 g/L to about 3.5 g/L.

In another embodiment the suspending agent is pectin, wherein the pectin is present in a composition of the invention in an amount in a range of from about 2 g/L to about 25 g/L, preferably in an amount in a range from about 3 g/L to about 20 g/L, more preferably in an amount from about 3.5 g/L to about 10.0 g/L. Exemplified ranges include but are not limited to: about 2.5 g/L to about 25 g/L; about 3 g/L to about 25 g/L; about 3.5 g/L to about 25 g/L; about 4 g/L to about 25 g/L; about 4.5 g/L to about 25 g/L; about 5 g/L to about 25 g/L; about 5.5 g/L to about 25 g/L; about 6 g/L to about 25 g/L; about 6.5 g/L to about 25 g/L; about 7 g/L to about 25 g/L; about 7.5 g/L to about 25 g/L; about 8 g/L to about 25 g/L; about 8.5 g/L to about 25 g/L; about 9 g/L to about 25 g/L; about 9.5 g/L to about 25 g/L; about 10 g/L to about 25 g/L; about 10.5 g/L to about 25 g/L; about 11 g/L to about 25 g/L; about 11.5 g/L to about 25 g/L; about 12 g/L to about 25 g/L; about 12.5 g/L to about 25 g/L; about 13 g/L to about 25 g/L; about 13.5 g/L to about 25 g/L; about 14 g/L to about 25 g/L; about 14.5 g/L to about 25 g/L; about 15 g/L to about 25 g/L; about 15.5 g/L to about 25 g/L; about 16 g/L to about 25 g/L; about 16.5 g/L to about 25 g/L; about 17 g/L to about 25 g/L; about 17.5 g/L to about 25 g/L; about 18 g/L to about 25 g/L; about 18.5 g/L to about 25 g/L; about 19 g/L to about 25 g/L; about 19.5 g/L to about 25 g/L; about 20 g/L to about 25 g/L; about 20.5 g/L to about 25 g/L; about 21 g/L to about 25 g/L; about 21.5 g/L to about 25 g/L; about 22 g/L to about 25 g/L; about 22.5 g/L to about 25 g/L; about 23 g/L to about 25 g/L; about 23.5 g/L to about 25 g/L; about 24 g/L to about 25 g/L; about 24.5 g/L to about 25 g/L; 2 g/L to about 24.5 g/L; about 2 g/L to about 24 g/L; about 2 g/L to about 23.5 g/L; about 2 g/L to about 23 g/L; about 2 g/L to about 22.5 g/L; about 2 g/L to about 22 g/L; about 2 g/L to about 21.5 g/L; about 2 g/L to about 21 g/L; about 2 g/L to about 20.5 g/L; about 2 g/L to about 20 g/L; about 2 g/L to about 19.5 g/L; about 2 g/L to about 19 g/L; about 2 g/L to about 18.5 g/L; about 2 g/L to about 18 g/L; about 2 g/L to about 17.5 g/L; about 2 g/L to about 17 g/L; about 2 g/L to about 16.5 g/L; about 2 g/L to about 16 g/L; about 2 g/L to about 15.5 g/L; about 2 g/L to about 15 g/L; about 2 g/L to about 14.5 g/L; about 2 g/L to about 14 g/L; about 2 g/L to about 13.5 g/L; about 2 g/L to about 13 g/L; about 2 g/L to about 12.5 g/L; about 2 g/L to about 12 g/L; about 2 g/L to about 11.5 g/L; about 2 g/L to about 11 g/L; about 2 g/L to about 10.5 g/L; about 2 g/L to about 10 g/L; about 2 g/L to about 9.5 g/L; about 2 g/L to about 9.0 g/L; about 2 g/L to about 8.5 g/L; about 2 g/L to about 8.0 g/L; about 2 g/L to about 7.5 g/L; about 2 g/L to about 7.0 g/L; about 2 g/L to about 6.5 g/L; about 2 g/L to about 6.0 g/L; about 2 g/L to about 5.5 g/L; about 2 g/L to about 5 g/L; about 2 g/L to about 4.5 g/L; about 2 g/L to about 4.0 g/L; about 2 g/L to about 3.5 g/L; about 2 g/L to about 3 g/L; or about 2 g/L to about 2.5 g/L.

In another embodiment, the suspending agent is a mixture of at least two compounds defined herein as a suspending agent where each individual suspending agent is present in an amount as defined herein.

In some embodiments the starch comprising a resistant starch may be soluble in water; here a compound defined herein as a suspending agent is still present.

In yet another embodiment, the suspending agent can be selected from the group comprising, but not limited to:
 brominated vegetable oil,
 calcium acetate,
 calcium stearoyl lactylate,
 dammar gum,
 disodium EDTA,
 glycerol ester of wood rosin
 gum ghatti,
 karaya gum,
 lactated mono- and di-glycerides,
 lactylated fatty acid esters of glycerol and propylene glycol,
 mono- and di-glycerides,
 poloxamer 331 poloxamer 407
polydextroses,
polysorbate 20, 60, 65 and 80,
polyvinylpyrrolidone,
processed eucheuma seaweed,
propylene glycol alginate,
propylene glycol mono- and di-esters,
sodium caseinate,
sodium L(+)-tartrate,
sorbitan monostearate,
stearyl monoglyceridyl citrate,
tara gum,
tragacanth gum,
tripotassium citrate,
trisodium phosphate, and
mixtures of suspending agents as disclosed or as described herein.

Starch Comprising a Resistant Starch

In one embodiment, the compositions of the invention, including for example a beverage, food item or an oral rehydration composition of the invention, comprise a starch comprising a resistant starch.

Resistant starch plays an important role in digestive function. Resistant starch is the total amount of starch and the products of starch degradation that resist digestion in the small intestine of healthy individuals. The resistant starch may be fermented in the large intestine or large bowel by resident or introduced (via, for example, probiotics) microflora.

Different starches contain different ratios of components that are readily broken down in the small intestine and components that are not broken down until they reach the large intestine.

The inventors have found that the amount of glucose released in the small intestine from the starch comprising a resistant starch is important in relation to the optimal functioning of the resulting oral rehydration compositions and solutions of the invention, wherein it is not only the amount of starch that is made available as glucose in the small intestine that is important, but also the rate at which this glucose is released for absorption.

An important application of the compositions of the invention is the targeted regulation of the rate and extent of glucose release in the small intestine combined with the delivery of resistant starch to the colon to optimally stimulate the generation of short chain fatty acids by the microflora to reduce diarrhoea through enhanced small and large intestinal fluid salvage. This can be accomplished by the choice and selection of the starch comprising a resistant starch being used in a composition of the invention, wherein the addition of a suspending agent ensures that the starch comprising a resistant starch is consumed when said composition is, for example, combined with an aqueous composition, preferably drinking water, and is ingested by an individual.

The amount and rate of glucose released from starch can be affected by a number of factors including:
the type of starch;
the size of starch granules;
the hydrothermal treatment of the starch;
whether the starch has been modified, for example by chemically treating the starch, and the type and extent of the modification(s);
starch granules that have been broken up or reduced in size by attrition, impact or fractionation;
the interaction with other dietary and food components; and/or
the health status of a person consuming the resistant starch.

Resistant starches can be grouped into five categories:
a type I resistant starch (RS1);
a type II resistant starch (RS2);
a type III resistant starch (RS3);
a type IV resistant starch (RS4); and
a type V resistant starch (RS5).

The classification for resistant starches is shown in Table 2.

TABLE 2

Classification of resistant starches.

| Type | Occurrence | Example |
| --- | --- | --- |
| RS1 - Physically inaccessible | Intact or partly milled grains and seeds | Intact whole grains |
| RS2 - Resistant granules | Raw potato, green banana, some legumes, high amylose maize | High amylose maize starch |
| RS3 - Retrograded starch | Cooked and cooled starchy foods | Recrystallised maize or tapioca starch |
| RS4 - Chemically modified starches | Starch ethers and esters cross-bonded starches | Sodium trimetaphosphate (STMP)/sodium tripolyphosphate (STPP) cross-linked wheat starch |
| RS5 - Starch-lipid inclusion complexes | Cooked, gelled, extruded starch in the presence of lipids, including polar lipids. | Amylose-lipid complexes with a V-form x-ray crystallography pattern; high amylose barley, such as BARLEYmax ™ (obtainable from CSIRO) |

In one embodiment the starch comprising a resistant starch has a minimum resistant starch content in a range of about 10% w/w to about 90% w/w, preferably in a range from about 20% w/w to about 75% w/w, more preferably in a range from about 30% w/w to about 65%, w/w most preferably in a range from about 40% w/w to about 60% w/w. Exemplified ranges include but are not limited to: about 15% w/w to about 90% w/w; about 20% w/w to about 90% w/w; about 25% w/w to about 90% w/w; about 30% w/w to about 35% w/w; about 40% w/w to about 90% w/w; about 45% w/w to about 90% w/w; about 50% w/w to about 90% w/w; about 55% w/w to about 90% w/w; about 60% w/w to about 90% w/w; about 65% w/w to about 90% w/w; about 70% w/w to about 90% w/w; about 75% w/w to about 90% w/w; about 80% w/w to about 90% w/w; about 85% w/w to about 90% w/w; about 10% w/w to about 85% w/w; about 10% w/w to about 80% w/w; about 10% w/w to about 75% w/w; about 10% w/w to about 70% w/w; about 10% w/w to about 65% w/w; about 10% w/w to about 60% w/w; about 10% w/w to about 55% w/w; about 10% w/w to about 50% w/w; about 10% w/w to about 45% w/w; about 10% w/w to about 40% w/w; about 10% w/w to about 35% w/w; about 10% w/w to about 30% w/w; about 10% w/w to about 25% w/w; about 10% w/w to about 20% w/w; or about 10% w/w to about 15% w/w.

In one embodiment the resistant starch of the invention is replaced or partly replaced with slowly digested starch, wherein "slowly digested" indicates a starch that is digested, once having passed the stomach, over a period of time in a range of from about 15 minutes to about 360 minutes, preferably in a range from about 15 minutes to about 240 minutes, most preferably in a range from about 15 minutes to about 120 minutes. Exemplified ranges include but are not limited to: about 30 minutes to about 360 minutes; about 60 minutes to about 360 minutes; about 90 minutes to about 360 minutes; about 120 minutes to about 360 minutes; about 180 minutes to about 360 minutes; about 240 minutes to about 360 minutes; about 300 minutes to about 360 minutes; about 30 minutes to about 240 minutes; about 30 minutes to about 180 minutes; about 30 minutes to about 120 minutes; or about 30 minutes to about 60 minutes.

"Starch comprising a resistant starch" encompasses all starches comprising resistant starches (flours, grits and other starch containing materials), which are derived from tubers, grains, legumes, fruit and seeds or any other native source, wherein "native source" refers to a naturally occurring source, which is suitable for the oral rehydration compositions, methods and uses as disclosed herein.

In addition, "starch comprising a resistant starch" encompasses all resistant starches which have been derived from plant material which is a "non-native" source, wherein the plant material is not naturally occurring and the plant material is from a plant that is the product of:
  crossbreeding;
  artificially induced mutations; or
  genetic modification wherein the genes or chromosones of a plant have undergone translocation, inversion or transformation.

Non-native plant sources comprise: tubers, grains, legumes, fruit and seeds.

The starches included in the compositions, methods and uses of the invention may be derived from a native or non-native source and used as such or are milled, physically, thermally or enzymatically processed, or modified, for example the starch can be milled to reduce the particle size of the starch to individual starch granules or to break the starch into pieces. The source can be from native, waxy or high amylose varieties of a particular species although it should be noted that high amylose varieties of starch usually have higher amounts of resistant starch.

Herein, high amylose starches are disclosed which are starches comprising resistant starches and include maize starch having an amylose content of at least 50% w/w, for example at least 55, 60, 65, 70, 75 or 80% w/w, particularly at least 80% w/w; rice starch having an amylose content of at least 27% w/w, or a wheat starch having an amylose content of at least 35% w/w. Furthermore, particular granular size ranges of starches having an amylose content of at least 50% w/w, and enhanced resistant starch content can be included in the present invention; these starches include starches derived from maize, barley, and legumes. The present invention is not, however, limited to these forms of resistant starch. For example, other forms of starch comprising a resistant starch can be derived from sources such as bananas and tubers such as potatoes.

In one embodiment the starch comprising a resistant starch is a RS1 starch. RS1 starches can be derived from any native flours (although the amount of resistant starch can be increased through specialist milling and/or thermal or hydrothermal, and/or enzymatic treatment).

In one embodiment the starch comprising a resistant starch is a RS1 starch which can be selected from the group comprising, but not limited to: whole- or partly-milled grains, seeds and legumes, where the starch is physically inaccessible to starch digesting enzymes.

In another embodiment the starch comprising a resistant starch is a RS2 starch which is starch that can be derived from the group comprising, but not limited to:
  grains and flours containing starch that have been derived from a native or non-native plant source (for example from conventional inbred breeding techniques or produced in the production of a genetically modified plant species), in particular with higher or elevated amylose content in the starch, that includes, but is not limited to:
  maize,
  wheat,
  rice,
  triticale,
  banana,
  barley,
  potato,
  legumes, for example peas,
  sago,
  sorghum,
  oats,
  tapioca,
  cassava and
  combinations thereof.

Examples of RS2 starches include, but are not limited to: high amylose maize or corn starches such as: a class V, or class VII (for example Hylon® VII (obtainable from Ingredion), Hi-maize™ 240 (obtainable from Ingredion), Hi-maize™ 260 (obtainable from Ingredion) or Hi-maize™ 1043 (obtainable from Ingredion)), class VIII (for example Hi-maize™ 958 (obtainable from Ingredion) or class X, high amylose maize starch.

In another embodiment the starch comprising a resistant starch is a RS3 starch. A RS3 derived material is formed by the heating, gelatinization and recrystallisation of starch polymers from a native or non-native plant source as described herein. A RS3 material can be selected from the group comprising, but not limited to:
  a high amylose maize starch (class VII), which has been gelatinized, retrograded, subjected to partial enzyme hydrolysis before recovery and drying (for example Novelose® 330, obtainable from Ingredion).

In another embodiment the starch comprising a resistant starch is a RS4 starch which is a starch sourced from a native or non-native source as described herein which has been chemically treated.

Chemical modifications utilised to produce a RS4 starch can include, but are not limited to: thermal or hydrothermal treatment, enzymatic modification, oxidation or bleaching (for example using hypochlorite containing compounds), treatment with propylene oxide to yield hydroxypropyl starch materials, cross-bonding or crosslinking, etherification, esterification (or acylation) (for example acetylation using a compound such as acetic acid, vinyl acetate, acetic anhydride, or another acetylation agent known to those skilled in the art, to produce acetylated starch materials, or acylation using, for example propionic acid, propionic anhydride, butyric acid, butyric anhydride, or another acylation agent known to those skilled in the art), acidification (for example with an inorganic or organic acid) or dextrinisation, treatment with an alkaline compound (for example sodium hydroxide or potassium hydroxide), phosphorylation (for example by treating a starch material with phosphoric acid and/or a phosphorylating agent to produce, for example a mono-starch phosphates, di-starch phosphates and phosphorylated di-starch phosphates), treatment with glycerol to produce a di-starch glycerol material, or combinations thereof (for example: treatment with a phosphorylating agent and an acetylating agent (such as acetic acid) to produce an acetylated di-starch phosphate; treatment with acetic acid and adipinic acid anhydride to provide acetylated di-starch adipate materials; treatment with propylene oxide, epichlorhydrine and glycerol to produce hydroxypropyl di-starch glycerol; and treatment with propylene oxide and phosphoric acid to produce hydroxypropyl di-starch phosphate), can be used as suitable chemical treatments. Similarly, other modifications can be induced physically, enzymatically or by other means which are known to those skilled in the art.

For example, the RS4 starch can be a starch that has been chemically modified using known treatments such as, for example: thermal or hydrothermal treatment, enzymatic modification, oxidation or bleaching (for example using hypochlorite containing compounds), treatment with propylene oxide to yield hydroxypropyl starch materials, crossbonding or crosslinking, etherification, esterification (or acylation) (for example acetylation using a compound such as acetic acid, vinyl acetate, acetic anhydride, or another acetylation agent known to those skilled in the art, to produce acetylated starch materials, or acylation using, for example propionic acid, propionic anhydride, butyric acid, butyric anhydride, or another acylation agent known to those skilled in the art), acidification (for example with an inorganic or organic acid) or dextrinisation, treatment with an alkaline compound (for example sodium hydroxide or potassium hydroxide), phosphorylation (for example by treating a starch material with phosphoric acid and/or a phosphorylating agent to produce, for example a mono-starch phosphates, di-starch phosphates and phosphorylated di-starch phosphates), treatment with glycerol to produce a di-starch glycerol material, or combinations thereof (for example: treatment with a phosphorylating agent and an acetylating agent (such as acetic acid) to produce an acetylated di-starch phosphate; treatment with acetic acid and adipinic acid anhydride to provide acetylated di-starch adipate materials; treatment with propylene oxide, epichlorhydrine and glycerol to produce hydroxypropyl di-starch glycerol; and treatment with propylene oxide and phosphoric acid to produce hydroxypropyl di-starch phosphate), where the starch is sourced from native, non-native waxy or high amylose varieties of a particular species, for example:

grains and flours containing starch that have been derived from a native or non-native plant source (for example from conventional inbred breeding techniques or produced in the production of a genetically modified plant species), in particular with higher or elevated amylose content in the starch, that includes, but is not limited to:
maize,
wheat,
rice,
triticale,
banana,
barley,
potato,
legumes, for example peas,
sago,
sorghum,
oats,
tapioca,
cassava and
combinations thereof.

Other examples of RS4 compounds that can be used in the present invention include starches which have been acylated, for example to produce:
acetylated starches, for example:
an acetylated tapioca starch;
an acetylated rice starch;
a retrograded gelatinised class VII high amylose maize starch;
a starch comprising a resistant starch, that is acetylated to a substitution value of up to and including 2.5%, including starches comprising resistant starches, that has been acetylated to a substitution value of up to about 0.5, about 1, about 1.5 and about 2% (for example Starplus™ A (obtainable from CSIRO) with an acetylation value of 2.5%); or
a starch comprising a resistant starch, that is acetylated with a substitution value greater than 2.5%, including greater than or equal to about 3.0%, about 3.5%, about 4.0%, about 4.5%, about 5.0%, about 5.5%, about 6.0%, about 6.5%, about 7.0% or about 7.5% (for example Crisp Film® (obtainable from Ingredion) or Starplus™ A (obtainable from CSIRO) with an acetylation value of 6.0%);
acylated starches, for example:
propionylated starches, for example a starch comprising a resistant starch, that is propionylated (for example Starplus™ P obtainable from CSIRO), with a substitution value greater than or equal to 2.5%, for example greater than or equal to about 2.5%, about 3.0%, about 3.5%, about 4.0%, about 4.5%, about 5.0%, about 5.5%, about 6.0%, about 6.5%, about 7.0%, or about 7.5%; or
butyrylated starches, including a starch comprising a resistant starch, that is butyrylated (for example Starplus™ B obtainable from CSIRO), to a substitution value greater than or equal to 2.5%, for example greater than or equal to about 2.5%, about 3.0%, about 3.5%, about 4.0%, about 4.5%, about 5.0%, about 5.5%, about 6.0%, about 6.5%, about 7.0%, or about 7.5%.

An RS5 is identified where resistance to normal starch digestion is inhibited by the starch existing as a clathrate or inclusion complex with a lipid. Analytically x-ray crystallography shows high amylose starch in the so called B-type form whereas RS5 is in the V-type form. The V-type form can be produced by cooking any starch in the presence of suitable lipid(s) and allowing their interaction to form inclusion complexes.

In one embodiment, the compositions of the invention, including for example a beverage, food item or an oral rehydration composition of the invention, comprise at least one of either a: RS1, RS2, RS3, RS4 or RS5 resistant starch.

In yet another embodiment, the compositions of the invention, including for example a beverage, food item or an oral rehydration composition of the invention, comprise at least one of either a: RS1, RS2, RS3, RS4, or RS5 resistant starch, in an amount as disclosed herein.

In yet another embodiment, the compositions of the invention, including for example a beverage, food item or an oral rehydration composition of the invention, comprise a mixture of two or more of a: RS1, RS2, RS3, RS4 or RS5 resistant starch.

In yet another embodiment, the compositions of the invention, including for example a beverage, food item or an oral rehydration composition of the invention, comprise a mixture of two or more of a: RS1, RS2, RS3, RS4 or RS5 resistant starch, wherein each of the RS1, RS2, RS3, RS4 or RS5 materials, are present in an amount as disclosed herein.

Herein, the starch comprising a resistant starch is disclosed in quantities in ranges of "g/L". These values disclose the quantity of the starch comprising a resistant starch that would be present in an aqueous composition produced by combining an oral rehydration composition of the invention with 1 L of water.

In one embodiment the starch comprising a resistant starch is present in a composition of the invention, for example a beverage, food item or oral rehydration composition of the invention, in an amount in a range of from about 10 g/L to about 80 g/L, preferably in an amount in a range from about 35 g/L to about 60 g/L, more preferably in an amount from about 45 g/L to about 55 g/L. Exemplified ranges include but are not limited to: about 15 g/L to about 80 g/L; about 20 g/L to about 80 g/L; about 25 g/L to about 80 g/L; about 30 g/L to about 80 g/L; about 35 g/L to about 80 g/L; about 40 g/L to about 80 g/L; about 45 g/L to about 80 g/L; about 50 g/L to about 80 g/L; about 55 g/L to about 80 g/L; about 60 g/L to about 80 g/L; about 65 g/L to about 80 g/L; about 70 g/L to about 80 g/L; about 75 g/L to about 80 g/L; about 10 g/L to about 75 g/L; about 10 g/L to about 70 g/L; about 10 g/L to about 65 g/L; about 10 g/L to about 60 g/L; about 10 g/L to about 55 g/L; about 10 g/L to about 50 g/L; about 10 g/L to about 45 g/L; about 10 g/L to about 40 g/L; about 10 g/L to about 35 g/L; about 10 g/L to about 30 g/L; about 10 g/L to about 25 g/L; or about 10 g/L to about 15 g/L.

In one embodiment the starch comprising a resistant starch is a RS1 starch, wherein the RS1 starch is present in a composition of the invention, for example a beverage, food item or oral rehydration composition of the invention, in an amount in a range of from about 10 g/L to about 80 g/L, preferably in an amount in a range from about 35 g/L to about 60 g/L, more preferably in an amount from about 45 g/L to about 55 g/L. Exemplified ranges include but are not limited to: about 15 g/L to about 80 g/L; about 20 g/L to about 80 g/L; about 25 g/L to about 80 g/L; about 30 g/L to about 80 g/L; about 35 g/L to about 80 g/L; about 40 g/L to about 80 g/L; about 45 g/L to about 80 g/L; about 50 g/L to about 80 g/L; about 55 g/L to about 80 g/L; about 60 g/L to about 80 g/L; about 65 g/L to about 80 g/L; about 70 g/L to about 80 g/L; about 75 g/L to about 80 g/L; about 10 g/L to about 75 g/L; about 10 g/L to about 70 g/L; about 10 g/L to about 65 g/L; about 10 g/L to about 60 g/L; about 10 g/L to about 55 g/L; about 10 g/L to about 50 g/L; about 10 g/L to about 45 g/L; about 10 g/L to about 40 g/L; about 10 g/L to about 35 g/L; about 10 g/L to about 30 g/L; about 10 g/L to about 25 g/L; or about 10 g/L to about 15 g/L.

In another embodiment the starch comprising a resistant starch is a RS1 starch, wherein the RS1 starch is present in a composition of the invention, for example a beverage, food item or oral rehydration composition of the invention, in an amount of about 40 g/L.

In another embodiment the starch comprising a resistant starch is a RS1 starch, wherein the RS1 starch is present in a composition of the invention, for example a beverage, food item or oral rehydration composition of the invention, in an amount of about 50 g/L.

In one embodiment the starch comprising a resistant starch is a RS2 starch, wherein the RS2 starch is present in a composition of the invention, for example a beverage, food item or oral rehydration composition of the invention, in an amount in a range of from about 10 g/L to about 80 g/L, preferably in an amount in a range from about 35 g/L to about 60 g/L, more preferably in an amount in a range from about 45 g/L to about 55 g/L. Exemplified ranges include but are not limited to: about 15 g/L to about 80 g/L; about 20 g/L to about 80 g/L; about 25 g/L to about 80 g/L; about 30 g/L to about 80 g/L; about 35 g/L to about 80 g/L; about 40 g/L to about 80 g/L; about 45 g/L to about 80 g/L; about 50 g/L to about 80 g/L; about 55 g/L to about 80 g/L; about 60 g/L to about 80 g/L; about 65 g/L to about 80 g/L; about 70 g/L to about 80 g/L; about 75 g/L to about 80 g/L; about 10 g/L to about 75 g/L; about 10 g/L to about 70 g/L; about 10 g/L to about 65 g/L; about 10 g/L to about 60 g/L; about 10 g/L to about 55 g/L; about 10 g/L to about 50 g/L; about 10 g/L to about 45 g/L; about 10 g/L to about 40 g/L; about 10 g/L to about 35 g/L; about 10 g/L to about 30 g/L; about 10 g/L to about 25 g/L; or about 10 g/L to about 15 g/L.

In another embodiment the starch comprising a resistant starch is a RS2 starch, wherein the RS2 starch is present in a composition of the invention, for example a beverage, food item or oral rehydration composition of the invention, in an amount of about 40 g/L.

In another embodiment the starch comprising a resistant starch is a RS2 starch, wherein the RS2 starch is present in a composition of the invention, for example a beverage, food item or oral rehydration composition of the invention, in an amount of about 50 g/L.

In one embodiment the starch comprising a resistant starch is a RS3 starch, wherein the RS3 starch is present in a composition of the invention, for example a beverage, food item or oral rehydration composition of the invention, in an amount in a range of from about 10 g/L to about 80 g/L, preferably in an amount in a range from about 35 g/L to about 60 g/L, more preferably in an amount in a range from about 45 g/L to about 55 g/L. Exemplified ranges include but are not limited to: about 15 g/L to about 80 g/L; about 20 g/L to about 80 g/L; about 25 g/L to about 80 g/L; about 30 g/L to about 80 g/L; about 35 g/L to about 80 g/L; about 40 g/L to about 80 g/L; about 45 g/L to about 80 g/L; about 50 g/L to about 80 g/L; about 55 g/L to about 80 g/L; about 60 g/L to about 80 g/L; about 65 g/L to about 80 g/L; about 70 g/L to about 80 g/L; about 75 g/L to about 80 g/L; about 10 g/L to about 75 g/L; about 10 g/L to about 70 g/L; about 10 g/L to about 65 g/L; about 10 g/L to about 60 g/L; about 10 g/L to about 55 g/L; about 10 g/L to about 50 g/L; about 10 g/L to about 45 g/L; about 10 g/L to about 40 g/L; about 10 g/L to about 35 g/L; about 10 g/L to about 30 g/L; about 10 g/L to about 25 g/L; or about 10 g/L to about 15 g/L.

In another embodiment the starch comprising a resistant starch is a RS3 starch, wherein the RS3 starch is present in a composition of the invention, for example a beverage, food item or oral rehydration composition of the invention, in an amount of about 40 g/L.

In another embodiment the starch comprising a resistant starch is a RS3 starch, wherein the RS3 starch is present in a composition of the invention, for example a beverage, food item or oral rehydration composition of the invention, in an amount of about 50 g/L.

In one embodiment the starch comprising a resistant starch is a RS4 starch, wherein the RS4 starch is present in a composition of the invention, for example a beverage, food item or oral rehydration composition of the invention, in an amount in a range of from about 10 g/L to about 80 g/L, preferably in an amount in a range from about 35 g/L to about 60 g/L, more preferably in an amount in a range from about 45 g/L to about 55 g/L. Exemplified ranges include but are not limited to: about 15 g/L to about 80 g/L; about 20 g/L to about 80 g/L; about 25 g/L to about 80 g/L; about 30 g/L to about 80 g/L; about 35 g/L to about 80 g/L; about 40 g/L to about 80 g/L; about 45 g/L to about 80 g/L; about 50 g/L to about 80 g/L; about 55 g/L to about 80 g/L; about 60 g/L to about 80 g/L; about 65 g/L to about 80 g/L; about 70 g/L to about 80 g/L; about 75 g/L to about 80 g/L; about 10 g/L to about 75 g/L; about 10 g/L to about 70 g/L; about 10 g/L to about 65 g/L; about 10 g/L to about 60 g/L; about 10 g/L to about 55 g/L; about 10 g/L to about 50 g/L; about 10 g/L to about 45 g/L; about 10 g/L to about 40 g/L; about 10 g/L to about 35 g/L; about 10 g/L to about 30 g/L; about 10 g/L to about 25 g/L; or about 10 g/L to about 15 g/L.

In another embodiment the starch comprising a resistant starch is a RS4 starch, wherein the RS4 starch is present in a composition of the invention, for example a beverage, food item or oral rehydration composition of the invention, in an amount of about 40 g/L.

In another embodiment the starch comprising a resistant starch is a RS4 starch, wherein the RS4 starch is present in a composition of the invention, for example a beverage, food item or oral rehydration composition of the invention, in an amount of about 50 g/L.

In one embodiment the starch comprising a resistant starch is a RS5 starch, wherein the RS5 starch is present in a composition of the invention, for example a beverage, food item or oral rehydration composition of the invention, in an amount in a range of from about 10 g/L to about 80 g/L, preferably in an amount in a range from about 35 g/L to about 60 g/L, more preferably in an amount in a range from about 45 g/L to about 55 g/L. Exemplified ranges include but are not limited to: about 15 g/L to about 80 g/L; about 20 g/L to about 80 g/L; about 25 g/L to about 80 g/L; about 30 g/L to about 80 g/L; about 35 g/L to about 80 g/L; about 40 g/L to about 80 g/L; about 45 g/L to about 80 g/L; about 50 g/L to about 80 g/L; about 55 g/L to about 80 g/L; about 60 g/L to about 80 g/L; about 65 g/L to about 80 g/L; about 70 g/L to about 80 g/L; about 75 g/L to about 80 g/L; about 10 g/L to about 75 g/L; about 10 g/L to about 70 g/L; about 10 g/L to about 65 g/L; about 10 g/L to about 60 g/L; about 10 g/L to about 55 g/L; about 10 g/L to about 50 g/L; about 10 g/L to about 45 g/L; about 10 g/L to about 40 g/L; about 10 g/L to about 35 g/L; about 10 g/L to about 30 g/L; about 10 g/L to about 25 g/L; or about 10 g/L to about 15 g/L.

In another embodiment the starch comprising a resistant starch is a RS5 starch, wherein the RS5 starch is present in a composition of the invention, for example a beverage, food item or oral rehydration composition of the invention, in an amount of about 40 g/L.

In another embodiment the starch comprising a resistant starch is a RS5 starch, wherein the RS5 starch is present in a composition of the invention, for example a beverage, food item or oral rehydration composition of the invention, in an amount of about 50 g/L.

Other Starches, Starch Containing Materials or Dietary Fibre

Other starches, starch containing materials or dietary fibre, and combinations thereof, could also be utilised in compositions of the invention, for example a beverage, food item or oral rehydration composition of the invention, in addition to or in place of the starch comprising a resistant starch.

In one embodiment other starches and starch containing materials include, but are not limited to: plant components, such as, grain, tuber, seeds, and the like, which may be physically, enzymatically or chemically modified, such as through the processes of dextrinisation or dry roasting in the presence or absence of a catalyst such as hydrochloric acid, nitric acid or sulfuric acid.

In another embodiment dietary fibre includes, but is not limited to: *psyllium*; inulin; oligosaccharides, such as fructo-, galacto-, malto-, isomalto-, gentio-, agaro-, neoagaro-, α-gluco-, β-gluco-, cyclo-, inulo-, glycosyl sucrose, latulose, lactosucrose, or xylosucrose; bran, pericarp, endosperm, or cell wall material from cereals such as wheat, triticale, sorghum, rice, sago, potato, tapioca, cassava, oats, barley, and corn, or pulses, such as peas and lupins, and the like, which may be further processed or modified, such as by bleaching, and the like.

Any starch or material containing starch as a component, such as flour, semolina, grits, polenta, and the like, employed in combination with or in place of the starch that comprises resistant starch in a composition of the invention, for example a beverage, food item or oral rehydration composition of the invention, is preferably in a solid form, more preferably as an anhydrous solid, most preferably as a dry powder.

Herein, the other starches, starch containing materials or dietary fibre are disclosed in quantities in ranges of "g/L". These values disclose the quantity of the other starches and starch containing materials or dietary fibre that would be present in an aqueous composition produced by combining an oral rehydration composition of the invention with 1 L of water.

In one embodiment the other starches, starch containing materials, or dietary fibre are present in a composition of the invention, for example a beverage or oral rehydration composition of the invention, in place of the starch comprising a resistant starch, wherein the other starches and starch containing materials, or dietary fibre are present in an amount in a range of from about 3 g/L to about 80 g/L, preferably in an amount in a range from about 35 g/L to about 60 g/L, more preferably in an amount in a range from about 45 g/L to about 55 g/L. Exemplified ranges include but are not limited to: about 5 g/L to about 80 g/L; about 10 g/L to about 80 g/L; about 15 g/L to about 80 g/L; about 20 g/L to about 80 g/L; about 25 g/L to about 80 g/L; about 30 g/L to about 80 g/L; about 35 g/L to about 80 g/L; about 40 g/L to about 80 g/L; about 45 g/L to about 80 g/L; about 50 g/L to about 80 g/L; about 55 g/L to about 80 g/L; about 60 g/L to about 80 g/L; about 65 g/L to about 80 g/L; about 70 g/L to about 80 g/L; about 75 g/L to about 80 g/L; about 3 g/L to about 75 g/L; about 3 g/L to about 70 g/L; about 3 g/L to about 65 g/L; about 3 g/L to about 60 g/L; about 3 g/L to about 55 g/L; about 3 g/L to about 50 g/L; about 3 g/L to about 45 g/L; about 3 g/L to about 40 g/L; about 3 g/L to about 35 g/L; about 3 g/L to about 30 g/L; about 3 g/L to about 25 g/L; about 3 g/L to about 20 g/L; about 3 g/L to about 15 g/L; about 3 g/L to about 10 g/L; or about 3 g/L to about 5 g/L.

In one embodiment the other starches and starch containing materials, or dietary fibre are present in a composition of the invention, for example a beverage or oral rehydration composition of the invention, in combination with the starch comprising a resistant starch, wherein the other starches and starch containing materials, or dietary fibre are present in an amount in a range of from about 3 g/L to about 80 g/L, preferably in an amount in a range from about 35 g/L to about 60 g/L, more preferably in an amount in a range from about 45 g/L to about 55 g/L. Exemplified ranges include but are not limited to: about 5 g/L to about 80 g/L; about 10 g/L to about 80 g/L; about 15 g/L to about 80 g/L; about 20 g/L to about 80 g/L; about 25 g/L to about 80 g/L; about 30 g/L to about 80 g/L; about 35 g/L to about 80 g/L; about 40 g/L to about 80 g/L; about 45 g/L to about 80 g/L; about 50 g/L to about 80 g/L; about 55 g/L to about 80 g/L; about 60 g/L to about 80 g/L; about 65 g/L to about 80 g/L; about 70 g/L to about 80 g/L; about 75 g/L to about 80 g/L; about 3 g/L to about 75 g/L; about 3 g/L to about 70 g/L; about 3 g/L to about 65 g/L; about 3 g/L to about 60 g/L; about 3 g/L to about 55 g/L; about 3 g/L to about 50 g/L; about 3 g/L to about 45 g/L; about 3 g/L to about 40 g/L; about 3 g/L to about 35 g/L; about 3 g/L to about 30 g/L; about 3 g/L to about 25 g/L; about 3 g/L to about 20 g/L; about 3 g/L to about 15 g/L; about 3 g/L to about 10 g/L; or about 3 g/L to about 5 g/L.

All details provided herein about how the starch that comprises a resistant starch is provided in a composition of the invention, for example a beverage, food item or oral rehydration composition of the invention, are equally applicable to any starch beyond the starch comprising a resistant starch that is employed either in combination with the starch comprising a resistant starch in a composition of the invention, for example a beverage, food item or oral rehydration composition of the invention, or in place of the starch comprising a resistant starch in a composition of the invention, for example a beverage or oral rehydration composition of the invention.

Salt Composition

The oral rehydration compositions of the invention comprise a salt composition.

In one embodiment the salt composition of the invention comprise compounds selected from sodium and potassium salts, including, but not limited to: bicarbonates, citrates and chloride salts, and combinations thereof.

Specific examples of suitable rehydration salts that can be used in the oral rehydration compositions of the invention include, but are not limited to:
  sodium chloride,
  potassium chloride,
  sodium citrate (including monosodium citrate, disodium citrate and trisodium citrate),
  sodium bicarbonate, and
  combinations thereof.

The sodium incorporated in oral rehydration compositions of the invention is absorbed along the length of both the small and large bowel. The sodium in a composition of the invention, for example a beverage, food item or oral rehydration composition of the invention, may come from a single source, for example from sodium chloride, or from a combination of sources, for example from sodium chloride and trisodium citrate (dihydrate).

The inventors have identified that the incorporation of starch comprising a resistant starch means that the release of glucose in the jejunum and the ileum, and the release of SCFAs in the colon matches the regional need, or capability, for sodium absorption.

In one embodiment the salt composition of the invention comprises at least one source of sodium.

In one embodiment the salt composition comprises at least one source of potassium.

In one embodiment the salt composition comprises at least one source of sodium and at least one source of potassium.

In one embodiment the salt composition of the invention comprises sodium chloride.

In one embodiment the salt composition of the invention comprises potassium chloride.

In one embodiment the salt composition of the invention comprises trisodium citrate (dihydrate).

In one embodiment the salt composition of the invention comprises sodium bicarbonate.

Herein, rehydration salts are disclosed in quantities in ranges of "mg/L" or "g/L". These values disclose the quantity of the rehydration salts that would be present in an aqueous composition produced by combining an oral rehydration composition of the invention with 1 L of water.

In one embodiment the salt composition of the invention comprises sodium chloride, wherein the sodium chloride is present in an amount in a range of from about 0.8 g/L to about 5.2 g/L, preferably in an amount in a range from about 2 g/L to about 3 g/L, more preferably in an amount from about 2.4 g/L to about 2.8 g/L. Exemplified ranges include but are not limited to: about 0.8 g/L to about 5.2 g/L; about 1.2 g/L to about 5.2 g/L; about 1.6 g/L to about 5.2 g/L; about 2.0 g/L to about 5.2 g/L; about 2.4 g/L to about 5.2 g/L; about 2.8 g/L to about 5.2 g/L; about 3.2 g/L to about 5.2 g/L; about 3.6 g/L to about 5.2 g/L; about 4.0 g/L to about 5.2 g/L; about 4.4 g/L to about 5.2 g/L; about 4.8 g/L to about 5.2 g/L; about 0.8 g/L to about 4.8 g/L; about 0.8 g/L to about 4.4 g/L; about 0.8 g/L to about 4.0 g/L; about 0.8 g/L to about 3.6 g/L; about 0.8 g/L to about 3.2 g/L; about 0.8 g/L to about 2.8 g/L; about 0.8 g/L to about 2.4 g/L; about 0.8 g/L to about 2.0 g/L; about 0.8 g/L to about 1.6 g/L; or about 0.8 g/L to about 1.2 g/L.

In another embodiment the salt composition of the invention comprises potassium chloride, wherein the potassium chloride is present in an amount in a range of from about 0.2 g/L to about 2 g/L, preferably in an amount in a range from about 0.8 g/L to about 1.9 g/L, more preferably in an amount from about 1.4 g/L to about 1.6 g/L. Exemplified ranges include but are not limited to: about 0.2 g/L to about 2 g/L; about 0.4 g/L to about 2 g/L; about 0.6 g/L to about 2 g/L; about 0.8 g/L to about 2 g/L; about 1.0 g/L to about 2 g/L; about 1.2 g/L to about 2 g/L; about 1.4 g/L to about 2 g/L; about 1.6 g/L to about 2 g/L; about 1.8 g/L to about 2 g/L; about 0.2 g/L to about 1.8 g/L; about 0.2 g/L to about 1.6 g/L; about 0.2 g/L to about 1.4 g/L; about 0.2 g/L to about 1.2 g/L; about 0.2 g/L to about 1.0 g/L; about 0.2 g/L to about 0.8 g/L; about 0.2 g/L to about 0.6 g/L; or about 0.2 g/L to about 0.4 g/L.

In another embodiment the salt composition of the invention comprises trisodium citrate (dihydrate), wherein the trisodium citrate (dihydrate) is present in an amount in a range of from about 0 g/L to about 3.4 g/L, preferably in an amount in a range from about 1.0 g/L to about 3.2 g/L, more preferably in an amount from about 2.7 g/L to about 3.1 g/L. Exemplified ranges include but are not limited to: about 0.4 g/L to about 3.4 g/L; about 0.8 g/L to about 3.4 g/L; about 1.2 g/L to about 3.4 g/L; about 1.6 g/L to about 3.4 g/L; about 2.0 g/L to about 3.4 g/L; about 2.4 g/L to about 3.4 g/L; about 2.8 g/L to about 3.4 g/L; about 3.2 g/L to about 3.4 g/L; about 0 g/L to about 3.0 g/L; about 0 g/L to about 2.6 g/L; about 0 g/L to about 2.2 g/L; about 0 g/L to about 1.8 g/L; about 0 g/L to about 1.4 g/L; about 0 g/L to about 1.0 g/L; about 0 g/L to about 1.0 g/L; about 0 g/L to about 0.6 g/L; or about 0 g/L to about 0.2 g/L.

In yet another embodiment the salt composition of the invention comprises sodium bicarbonate, wherein the sodium bicarbonate is present in an amount in a range of from about 0 g/L to about 3 g/L, preferably in an amount in a range from about 2.2 g/L to about 2.8 g/L, more preferably in an amount from about 2.4 g/L to about 2.6 g/L. Exemplified ranges include but are not limited to: about 0 g/L to about 3 g/L; about 0.4 g/L to about 3 g/L; about 0.8 g/L to about 3 g/L; about 1.2 g/L to about 3 g/L; about 1.6 g/L to about 3 g/L; about 2.0 g/L to about 3 g/L; about 2.4 g/L to about 3 g/L; about 2.8 g/L to about 3 g/L; about 0 g/L to about 2.6 g/L; about 0 g/L to about 2.2 g/L; about 0 g/L to about 1.8 g/L; about 0 g/L to about 1.4 g/L; about 0 g/L to about 1.0 g/L; about 0 g/L to about 0.6 g/L; or about 0 g/L to about 0.2 g/L.

In yet another embodiment, the salt composition of the invention comprises one compound or one or more compounds selected from: sodium chloride, potassium chloride, trisodium citrate (dihydrate) and sodium bicarbonate in amounts as disclosed herein.

In another embodiment an oral rehydration composition of the invention comprises sodium in an amount in a range from about 450 mg/L to about 800 mg/L. Exemplified ranges include but are not limited to: about 500 mg/L to about 800 mg/L; about 550 mg/L to about 800 mg/L; about 600 mg/L to about 800 mg/L; about 650 mg/L to about 800 mg/L; about 700 mg/L to about 800 mg/L; about 750 mg/L to about 800 mg/L; about 450 mg/L to about 750 mg/L; about 450 mg/L to about 700 mg/L; about 450 mg/L to about 650 mg/L; about 450 mg/L to about 600 mg/L; about 450 mg/L to about 550 mg/L; or about 450 mg/L to about 500 mg/L.

In yet another embodiment an oral rehydration composition of the invention comprises potassium in an amount in a range from about 100 mg/L to about 400 mg/L. Exemplified ranges include but are not limited to: about 150 mg/L to about 400 mg/L; about 200 mg/L to about 400 mg/L; about 250 mg/L to about 400 mg/L; about 300 mg/L to about 400 mg/L; about 350 mg/L to about 400 mg/L; about 100 mg/L to about 350 mg/L; about 100 mg/L to about 300 mg/L; about 100 mg/L to about 250 mg/L; about 100 mg/L to about 200 mg/L; or about 100 mg/L to about 150 mg/L.

Osmolarity

In one embodiment a composition of the invention, for example a beverage or oral rehydration composition of the invention, has an osmolarity in a range of about 100 mOsmol/L to about 350 mOsmol/L, preferably an osmolarity in a range of about 160 mOsmol/L to about 340 mOsmol/L, most preferably an osmolarity in a range of about 170 mOsmol/L to about 245 mOsmol/L. Exemplified ranges include but are not limited to: about 125 mOsmol/L to about 350 mOsmol/L; about 150 mOsmol/L to about 350 mOsmol/L; about 175 mOsmol/L to about 350 mOsmol/L; about 200 mOsmol/L to about 350 mOsmol/L; about 225 mOsmol/L to about 350 mOsmol/L; about 250 mOsmol/L to about 350 mOsmol/L; about 275 mOsmol/L to about 350 mOsmol/L; about 300 mOsmol/L to about 350 mOsmol/L; about 325 mOsmol/L to about 350 mOsmol/L; about 100 mOsmol/L to about 325 mOsmol/L; about 100 mOsmol/L to about 300 mOsmol/L; about 100 mOsmol/L to about 275 mOsmol/L; about 100 mOsmol/L to about 250 mOsmol/L; about 100 mOsmol/L to about 225 mOsmol/L; about 100 mOsmol/L to about 200 mOsmol/L; about 100 mOsmol/L to about 175 mOsmol/L; about 100 mOsmol/L to about 150 mOsmol/L; or about 100 mOsmol/L to about 150 mOsmol/L.

Optional Additional Additives:

A composition of the invention, for example a beverage or an oral rehydration composition of the invention, may optionally further comprise additional pharmaceutically acceptable auxiliaries including, but not limited to:
  colours,
  flavours (for example lemon, raspberry apple, blackcurrant, tropical, pineapple or orange flavourings), the flavourings may be provided by a commercial cordial),
  sweeteners (including, but not limited to: sweeteners from both natural and artificial sources, sugars, sugar alcohols (polyols) and proteins, for example: natural sweeteners (for example mogrosides, glucose, fructose, sucrose and LoGicane™); amino acids (for example alanine, glycine, serine); artificial high intensity sweeteners (for example sucralose, alitame, cyclamate, aspartame, neotame, potassium acesulfame, and saccharin); natural high intensity sweeteners (for example, *Stevia rebaudiana*, Luo Han Guo, and glycyrrhizin from liquorice root); sweet-tasting proteins (for example, thaumatin from *Thaumatococcus daniellii*, monellin from *Dioscoreophyllum cumminsii*, brazzein from *Pentadiplandra brazzeana*, mabinlin and curculin); sugar alcohols—polyols or hydrogenated sugars—(for example sorbitol, xylitol, lactitol, mannitol, maltitol, isomalt and erythritol); and starch derived sweeteners (for example maltodextrins, glucose syrup, malto-oligosaccharides, tagatose and polydextrose). The sweetener may be chosen in order to contribute more than sweetness to an oral rehydration composition of the invention, for example body or mouth feel, reduced calories, or reduced osmotic effect. These exemplified sweeteners might be used alone or in combination to give the desired organoleptic appeal and physiological effect,
  flow agents, including (for example silica),
  zinc, wherein the zinc is in the form of water soluble salts including, but not limited to: zinc acetate, zinc picolinate or zinc gluconate,
  magnesium, wherein the magnesium is in the form of water soluble salts including, but not limited to: magnesium chloride,
  copper, wherein copper is in the form of water soluble salts including, but not limited to: copper sulphate,
  probiotics,
  prebiotics
  glucose,
  and combinations thereof.

Herein, the optional additional additives are disclosed in quantities in ranges of "mg/L" or "g/L". These values disclose the quantity of the optional additional additives that would be present in an aqueous composition produced by, for example, combining an oral rehydration composition of the invention with 1 L of water.

In one embodiment, a composition of the invention, for example a beverage or oral rehydration composition of the invention, further comprises silica, wherein the silica is present in an amount in a range from about 200 mg/L to about 800 mg/L, preferably in an amount in a range from about 300 mg/L to about 700 mg/L, most preferably in an amount in a range from about 400 mg/L to about 600 mg/L. Exemplified ranges include, but are not limited to: about 250 mg/L to about 800 mg/L; about 300 mg/L to about 800 mg/L; about 350 mg/L to about 800 mg/L; about 400 mg/L to about 800 mg/L; about 450 mg/L to about 800 mg/L; about 500 mg/L to about 800 mg/L; about 550 mg/L to about 800 mg/L; about 600 mg/L to about 800 mg/L; about 650 mg/L to about 800 mg/L; about 700 mg/L to about 800 mg/L; about 750 mg/L to about 800 mg/L; about 200 mg/L to about 750 mg/L; about 200 mg/L to about 700 mg/L; about 200 mg/L to about 650 mg/L; about 200 mg/L to about 600 mg/L; about 200 mg/L to about 550 mg/L; about 200 mg/L to about 500 mg/L; about 200 mg/L to about 450 mg/L; about 200 mg/L to about 400 mg/L; about 200 mg/L to about 350 mg/L; about 200 mg/L to about 300 mg/L; or about 200 mg/L to about 250 mg/L.

In another embodiment, a composition of the invention, for example a beverage or oral rehydration composition of the invention, further comprises zinc acetate, wherein the zinc acetate is present in an amount to provide elemental zinc in a range from about 1 mg/L to about 10 mg/L, preferably in an amount in a range from about 4 mg/L to about 7 mg/L, most preferably in an amount in a range from about 5 mg/L to about 6 mg/L. Exemplified ranges include, but are not limited to: about 2 mg/L to about 10 mg/L; about 3 mg/L to about 10 mg/L; about 4 mg/L to about 10 mg/L; about 5 mg/L to about 10 mg/L; about 6 mg/about 10 mg/L; about 7 mg/L to about 10 mg/L; about 8 mg/L to about 10 mg/L; about 9 mg/L to about 10 mg/L; about 1 mg/L to about 9 mg/L; about 1 mg/L to about 8 mg/L; about 1 mg/L to about 7 mg/L; about 1 mg/L to about 6 mg/L; about 1 mg/L to about 5 mg/L; about 1 mg/L to about 4 mg/L; about 1 mg/L to about 3 mg/L; or about 1 mg/L to about 2 mg/L.

In another embodiment, a composition of the invention, for example a beverage or oral rehydration composition of the invention, further comprises zinc gluconate, wherein the zinc gluconate is present in an amount to provide elemental zinc in a range from about 1 mg/L to about 10 mg/L, preferably in an amount in a range from about 4 mg/L to about 7 mg/L, most preferably in an amount in a range from about 5 mg/L to about 6 mg/L. Exemplified ranges include, but are not limited to: about 2 mg/L to about 10 mg/L; about 3 mg/L to about 10 mg/L; about 4 mg/L to about 10 mg/L; about 5 mg/L to about 10 mg/L; about 6 mg/about 10 mg/L; about 7 mg/L to about 10 mg/L; about 8 mg/L to about 10 mg/L; about 9 mg/L to about 10 mg/L; about 1 mg/L to about 9 mg/L; about 1 mg/L to about 8 mg/L; about 1 mg/L to about 7 mg/L; about 1 mg/L to about 6 mg/L; about 1 mg/L to about 5 mg/L; about 1 mg/L to about 4 mg/L; about 1 mg/L to about 3 mg/L; or about 1 mg/L to about 2 mg/L.

In another embodiment, a composition of the invention, for example a beverage or oral rehydration composition of the invention, further comprises zinc picolinate, wherein the zinc picolinate is present in an amount to provide elemental zinc in a range from about 1 mg/L to about 10 mg/L, preferably in an amount in a range from about 4 mg/L to about 7 mg/L, most preferably in an amount in a range from about 5 mg/L to about 6 mg/L. Exemplified ranges include, but are not limited to: about 2 mg/L to about 10 mg/L; about 3 mg/L to about 10 mg/L; about 4 mg/L to about 10 mg/L; about 5 mg/L to about 10 mg/L; about 6 mg/about 10 mg/L; about 7 mg/L to about 10 mg/L; about 8 mg/L to about 10 mg/L; about 9 mg/L to about 10 mg/L; about 1 mg/L to about 9 mg/L; about 1 mg/L to about 8 mg/L; about 1 mg/L to about 7 mg/L; about 1 mg/L to about 6 mg/L; about 1 mg/L to about 5 mg/L; about 1 mg/L to about 4 mg/L; about 1 mg/L to about 3 mg/L; or about 1 mg/L to about 2 mg/L.

In yet another embodiment, a composition of the invention, for example a beverage or oral rehydration composition of the invention, further comprises magnesium chloride, wherein the magnesium chloride is present in an amount to provide elemental magnesium in a range from about 3 mg/L to about 7.8 mg/L, preferably in an amount in a range from about 4 mg/L to about 7 mg/L, most preferably in an amount in a range from about 5 mg/L to about 6 mg/L. Exemplified ranges include, but are not limited to: about 3.5 mg/L to about 7.8 mg/L; about 4.0 mg/L to about 7.8 mg/L; about 4.5 mg/L to about 7.8 mg/L; about 5.0 mg/L to about 7.8 mg/L; about 5.5 mg/L to about 7.8 mg/L; about 6.0 mg/L to about 7.8 mg/L; about 6.5 mg/L to about 7.8 mg/L; about 7.0 mg/L to about 7.8 mg/L; about 3 mg/L to about 7.5 mg/L; about 3 mg/L to about 7.0 mg/L; about 3 mg/L to about 6.5 mg/L; about 3 mg/L to about 6.0 mg/L; about 3 mg/L to about 5.5 mg/L; about 3 mg/L to about 5.0 mg/L; about 3 mg/L to about 4.5 mg/L; about 3 mg/L to about 4.0 mg/L; or about 3 mg/L to about 3.5 mg/L.

In a further embodiment, a composition of the invention, for example a beverage or oral rehydration composition of the invention, further comprises copper sulphate, wherein the copper sulphate is present in an amount to provide elemental copper in a range from about 1 mg/L to about 4 mg/L, preferably in an amount in a range from about 2 mg/L to about 3 mg/L, most preferably in an amount in a range from about 2.2 mg/L to about 2.8 mg/L. Exemplified ranges include, but are not limited to: about 1.5 mg/L to about 4 mg/L; about 2.0 mg/L to about 4 mg/L; about 2.5 mg/L to about 4 mg/L; about 3.0 mg/L to about 4 mg/L; about 3.5 mg/L to about 4 mg/L; about 1 mg/L to about 3.5 mg/L; about 1 mg/L to about 3.0 mg/L; about 1 mg/L to about 2.5 mg/L; about 1 mg/L to about 2.0 mg/L; or about 1 mg/L to about 1.5 mg/L.

In another further embodiment, a composition of the invention, for example a beverage or oral rehydration composition of the invention, can, if required, further comprise glucose, wherein the glucose is present in an amount in a range from about 1 g/L to about 25 g/L, preferably in an amount in a range from about 2 g/L to about 13 g/L, most preferably in an amount in a range from about 2 g/L to about 8 g/L. Exemplified ranges include, but are not limited to: about 2.5 g/L to about 25 g/L; about 5 g/L to about 25 g/L; about 7.5 g/L to about 25 g/L; about 10 g/L to about 25 g/L; about 12.5 g/L to about 25 g/L; about 15 g/L to about 25 g/L; about 17.5 g/L to about 25 g/L; about 20 g/L to about 25 g/L; about 22.5 g/L to about 25 g/L; about 1 g/L to about 22.5 g/L; about 1 g/L to about 20 g/L; about 1 g/L to about 17.5 g/L; about 1 g/L to about 15 g/L; about 1 g/L to about 12.5 g/L; about 1 g/L to about 10 g/L; about 1 g/L to about 7.5 g/L; or about 1 g/L to about 5 g/L.

In another further embodiment, a composition of the invention, for example a beverage or oral rehydration composition of the invention, can, if required, further comprise anhydrous glucose, wherein the anhydrous glucose is present in an amount in a range from about 1 g/L to about 25 g/L, preferably in an amount in a range from about 2 g/L to about 13 g/L, most preferably in an amount in a range from about 2 g/L to about 8 g/L. Exemplified ranges include, but are not limited to: about 2.5 g/L to about 25 g/L; about 5 g/L to about 25 g/L; about 7.5 g/L to about 25 g/L; about 10 g/L to about 25 g/L; about 12.5 g/L to about 25 g/L; about 15 g/L to about 25 g/L; about 17.5 g/L to about 25 g/L; about 20 g/L to about 25 g/L; about 22.5 g/L to about 25 g/L; about 1 g/L to about 22.5 g/L; about 1 g/L to about 20 g/L; about 1 g/L to about 17.5 g/L; about 1 g/L to about 15 g/L; about 1 g/L to about 12.5 g/L; about 1 g/L to about 10 g/L; about 1 g/L to about 7.5 g/L; or about 1 g/L to about 5 g/L.

In another further embodiment, a composition of the invention, for example a beverage or oral rehydration composition of the invention, can, if required, further comprise glucose monohydrate, wherein the glucose monohydrate is present in an amount in a range from about 1 g/L to about 25 g/L, preferably in an amount in a range from about 2 g/L to about 13 g/L, most preferably in an amount in a range from about 2 g/L to about 8 g/L. Exemplified ranges include, but are not limited to: about 2.5 g/L to about 25 g/L; about 5 g/L to about 25 g/L; about 7.5 g/L to about 25 g/L; about 10 g/L to about 25 g/L; about 12.5 g/L to about 25 g/L; about 15 g/L to about 25 g/L; about 17.5 g/L to about 25 g/L; about 20 g/L to about 25 g/L; about 22.5 g/L to about 25 g/L; about 1 g/L to about 22.5 g/L; about 1 g/L to about 20 g/L; about 1 g/L to about 17.5 g/L; about 1 g/L to about 15 g/L; about 1 g/L to about 12.5 g/L; about 1 g/L to about 10 g/L; about 1 g/L to about 7.5 g/L; or about 1 g/L to about 5 g/L.

In yet a further embodiment a composition of the invention, for example a beverage or oral rehydration composition of the invention, can comprise glucose (for example anhydrous glucose or glucose monohydrate) in an amount of about 5 g/L.

Treatment of Dehydration

The oral rehydration compositions of the invention can be used in the treatment of dehydration.

Herein an individual may be suffering from dehydration which is substantially or wholly due to diarrhoea. Alternatively an individual's dehydration may be caused in part by diarrhoea in combination with other factors such as: environmental temperatures, other medical conditions or illnesses, or through physical exertion.

Herein, an individual may be suffering from dehydration which is substantially or wholly due to the individual taking in a physical activity such as a sport.

In one embodiment an oral rehydration composition of the invention is combined in water, preferably drinking water, to yield an aqueous composition that is used to treat an individual suffering from dehydration.

In another embodiment an oral rehydration composition of the invention is combined in water, preferably drinking water, to yield an aqueous composition that is used to treat an individual suffering from dehydration caused by diarrhoea, or caused by diarrhoea in combination with other factors such as: environmental temperatures, other medical conditions or illnesses, or through physical exertion.

In another embodiment an oral rehydration composition of the invention is combined in water, preferably drinking water, to yield an aqueous composition that is used to treat an individual suffering from dehydration caused by the individual taking part in a physical activity, or caused by the individual taking part in a physical activity in combination with other factors such as: environmental temperatures, or other medical conditions or illnesses.

In a further embodiment, an effective amount of an aqueous composition comprising an oral rehydration composition of the invention required to treat an individual suffering from dehydration will be known to a person skilled in the art. The effective amount will be dependent on the severity of dehydration in the individual, the cause of dehydration, whether the individual is being treated to correct or prevent dehydration, and the size and/or age of the individual.

In yet a further embodiment, an effective amount of an aqueous composition comprising an oral rehydration composition of the invention required to treat an individual suffering from dehydration caused by diarrhoea, will be known to a person skilled in the art. The effective amount will be dependent on the severity of dehydration in the individual, the cause of the diarrhoea, whether the individual is being treated to correct or prevent dehydration, and the size and/or age of the individual.

In yet a further embodiment, an effective amount of an aqueous composition comprising an oral rehydration composition of the invention required to treat an individual suffering from dehydration caused by the individual partaking in a physical activity, will be known to a person skilled in the art. The effective amount will be dependent on the severity of dehydration in the individual, whether the individual is being treated to correct or prevent dehydration, and the size and/or age of the individual.

In another embodiment an effective amount of an aqueous composition comprising an oral rehydration composition of the invention required to correct dehydration in a child with diarrhoea is about 75 mL/kg given in four hours to the child, for example when the child comes to a health care facility.

In another embodiment, when an aqueous composition comprising an oral rehydration composition of the invention is for the treatment of dehydration caused by diarrhoea in a patient, the patient is given as much of the aqueous composition as required until the diarrhoea stops, based on the severity of the dehydration and the age of the patient.

In yet another embodiment, when an aqueous composition comprising an oral rehydration composition of the invention is for the treatment of dehydration caused by diarrhoea in a patient and the patient is a child under 2 years of age, after each loose stool the patient is given the aqueous composition in an amount in a range of about 42.5 mL to about 115 mL, preferably an amount in a range of about 45 mL to about 110 mL, most preferably in an amount in a range of about 50 mL to about 100 mL. Exemplified ranges include, but are not limited to: about 45 mL to about 115 mL; about 55 mL to about 115 mL; about 65 mL to about 115 mL; about 75 mL to about 115 mL; about 85 mL to about 115 mL; about 95 mL to about 115 mL; about 105 mL to about 115 mL; about 42.5 mL to about 105 mL; about 42.5 mL to about 95 mL; about 42.5 mL to about 85 mL; about 42.5 mL to about 75 mL; about 42.5 mL to about 65 mL; or about 42.5 mL to about 55 mL.

In yet another embodiment, when an aqueous composition comprising an oral rehydration composition of the invention is for the treatment of dehydration caused by diarrhoea in a patient and the patient is a child aged 2 up to 10 years, after each loose stool the patient is given the aqueous composition in an amount in a range of about 85 mL to about 230 mL, preferably an amount in a range of about 90 mL to about 220 mL, most preferably in an amount in a range of about 100 mL to about 200 mL. Exemplified ranges include, but are not limited to: about 90 mL to about 230 mL; about 100 mL to about 230 mL; about 110 mL to about 230 mL; about 120 mL to about 230 mL; about 130 mL to about 230 mL; about 140 mL to about 230 mL; about 150 mL to about 230 mL; about 160 mL to about 230 mL; about 170 mL to about 230 mL; about 180 mL to about 230 mL; about 190 mL to about 230 mL; about 200 mL to about 230 mL; about 210 mL to about 230 mL; about 220 mL to about 230 mL; about 85 mL to about 230 mL; about 85 mL to about 230 mL; about 85 mL to about 230 mL; about 85 mL to about 230 mL; about 85 mL to about 220 mL; about 85 mL to about 210 mL; about 85 mL to about 200 mL; about 85 mL to about 190 mL; about 85 mL to about 180 mL; about 85 mL to about 170 mL; about 85 mL to about 160 mL; about 85 mL to about 150 mL; about 85 mL to about 140 mL; about 85 mL to about 130 mL; about 85 mL to about 120 mL; about 85 mL to about 110 mL; about 85 mL to about 100 mL; or about 85 mL to about 90 mL.

In yet another embodiment, when an aqueous composition comprising an oral rehydration composition of the invention is for the treatment of dehydration caused by diarrhoea in a patient and the patient is a child more than 10 years old or an adult, after each loose stool the patient is given the aqueous composition in an amount in a range of about 8.5 mL/kg body weight to about 11.5 mL/kg body weight, preferably an amount in a range of about 9 mL/kg body weight to about 11 mL/kg body weight, most preferably in an amount of about 10 mL/kg body weight. Exemplified ranges include, but are not limited to: about 9 mL/kg body weight to about 11.5 mL/kg body weight; about 9.5 mL/kg body weight to about 11.5 mL/kg body weight; about 10 mL/kg body weight to about 11.5 mL/kg body weight; about 10.5 mL/kg body weight to about 11.5 mL/kg body weight; about 11 mL/kg body weight to about 11.5 mL/kg body weight; about 8.5 mL/kg body weight to about 11 mL/kg body weight; about 8.5 mL/kg body weight to about 10.5 mL/kg body weight; about 8.5 mL/kg body weight to about 10 mL/kg body weight; about 8.5 mL/kg body weight to about 9.5 mL/kg body weight; or about 8.5 mL/kg body weight to about 9 mL/kg body weight.

In yet another embodiment, when an aqueous composition comprising an oral rehydration composition of the invention is for the treatment of dehydration caused by diarrhoea in a patient and the patient is a child more than 10 years old or an adult, after each loose stool the patient is given as much of the aqueous composition as is required to treat the dehydration, based upon the severity of the dehydration.

In some embodiments the dehydration is caused by diarrhoea resulting from a disease or infection. Examples of infections include, but are not limited to, gastrointestinal infections caused by:

bacterial pathogens including *E. coli, Shigella, V. cholerae* (leading to cholera), *Campylobacter, Aeromonas, Clostridium difficile* and *Salmonella;* viral pathogens including rotavirus and norovirus (formerly known as Norwalk virus); and protozoan pathogens including *Giardia intestinalis, Cryptosporidium, Isospora belli, Encephalitozoon intestinalis* and *Entamoeba histolytica.*

In a further embodiment, an oral rehydration composition of the invention is used to treat dehydration caused by situations other than disease including, for example, physical exertion through sport, or dehydration caused by exposure to a hot environment. Here the effective amount of oral rehydration composition of the invention consumed will be dependent on the severity of the dehydration in the individual.

In yet a further embodiment, oral rehydration compositions of the invention can be used in the treatment of dehydration in an animal. The components of the oral rehydration, as defined herein (in one embodiment, the components include: a salt composition, a starch comprising a resistant starch, a suspending agent and optionally one or more of an optional additional additive as hereinbefore defined), will be appropriately chosen by a person skilled in the art based on species and the size of the animal.

In a further embodiment, the effective amount of an aqueous composition comprising an oral rehydration composition of the invention required to treat an animal suffering from dehydration will be known to a person skilled in the art. The effective amount will be dependent on the severity of dehydration in the animal, the cause of dehydration, the species of the animal and the size and/or age of the animal.

In yet a further embodiment, oral rehydration compositions of the invention can be used with an animal that engages in a physical activity, such as a sport (for example dog or horse racing). The components of the oral rehydration, as defined herein (in one embodiment, the components include: a salt composition, a starch comprising a resistant starch, a suspending agent and optionally one or more of an optional additional additive as hereinbefore defined), will be appropriately chosen by a person skilled in the art based on species and the size of the animal. The oral rehydration composition allowing the animal to be rehydrated following the physical activity or during the physical activity.

In yet a further embodiment, oral rehydration compositions of the invention can be used with an animal to provide a treatment for dehydration caused by diarrhoea, wherein the diarrhoea is caused by, for example, diseases, including, but not limited to: bacterial and viral induced diarrhoea and also diarrhoea which is a result of weaning the animal. The components of the oral rehydration, as defined herein (in one embodiment, the components include: a salt composition, a starch comprising a resistant starch, a suspending agent and optionally one or more of an optional additional additive as hereinbefore defined), will be appropriately chosen by a person skilled in the art based on species and the size of the animal.

In a further embodiment, the effective amount of an aqueous composition comprising an oral rehydration composition of the invention required to treat an animal suffering from dehydration following a physical activity, such as a sport, or to maintain hydration during a physical activity, in an animal will be known to a person skilled in the art. The effective amount will be dependent on the severity of dehydration in the animal, the cause of dehydration, the species of the animal and the size and/or age of the animal.

Herein, the term "animal" includes, but is not limited to:
mammals, including but not limited to:
dogs (including greyhounds), cats, rabbits, horses;
laboratory animals (including, but not limited to: rats, mice and primates);
livestock and farmed animals (including, but not limited to: cattle, buffalo, llamas, pigs, sheep, alpaca and deer);
reptiles; and
birds.

Beverages, Food Items and Additional Drinks Comprising a Resistant Starch

Herein a beverage that comprises a resistant starch can be consumed by an individual prior to the individual taking part in a physical activity such as a sport. Alternatively the beverage may be consumed during or after the physical activity. The beverage may be provided in order to rehydrate an individual or to maintain hydration.

Herein a food item that comprises a resistant starch can be consumed by an individual prior to the individual taking part in a physical activity such as a sport. Alternatively the food item may be consumed during or after the physical activity. The food item may be provided in order to aid in the rehydration of an individual or to help in maintaining hydration in the individual.

In one embodiment the beverage may be an oral rehydration composition as defined herein.

In one preferred embodiment, the beverage comprises a resistant starch.

In one preferred embodiment, the food item comprises a resistant starch.

In one embodiment, a beverage of the invention, comprises at least one of either a: RS1, RS2, RS3, RS4 or RS5 resistant starch, where the RS1, RS2, RS3, RS4 and RS5 materials are as defined herein.

In yet another embodiment, a beverage of the invention comprises at least one of either a: RS1, RS2, RS3, RS4, or RS5 resistant starch, in an amount as disclosed herein, where the RS1, RS2, RS3, RS4 and RS5 materials are as defined herein.

In yet another embodiment, a beverage of the invention comprises a mixture of two or more of a: RS1, RS2, RS3, RS4 or RS5 resistant starch, where the RS1, RS2, RS3, RS4 and RS5 materials are as defined herein.

In yet another embodiment, a beverage of the invention comprises a mixture of two or more of a: RS1, RS2, RS3, RS4 or RS5 resistant starch, wherein each of the RS1, RS2, RS3, RS4 or RS5 materials, are present in an amount as disclosed herein and where the RS1, RS2, RS3, RS4 and RS5 materials are as defined herein.

In one embodiment, a food item of the invention, comprises at least one of either a: RS1, RS2, RS3, RS4 or RS5 resistant starch, where the RS1, RS2, RS3, RS4 and RS5 materials are as defined herein.

In yet another embodiment, a food item of the invention comprises at least one of either a: RS1, RS2, RS3, RS4, or RS5 resistant starch, in an amount as disclosed herein, where the RS1, RS2, RS3, RS4 and RS5 materials are as defined herein.

In yet another embodiment, a food item of the invention comprises a mixture of two or more of a: RS1, RS2, RS3, RS4 or RS5 resistant starch, where the RS1, RS2, RS3, RS4 and RS5 materials are as defined herein.

In yet another embodiment, a food item of the invention comprises a mixture of two or more of a: RS1, RS2, RS3, RS4 or RS5 resistant starch, wherein each of the RS1, RS2, RS3, RS4 or RS5 materials, are present in an amount as disclosed herein and where the RS1, RS2, RS3, RS4 and RS5 materials are as defined herein.

In one embodiment a beverage, food item or an additional drink of the invention comprises a salt composition as defined herein.

In one embodiment a beverage, food item or an additional drink of the invention comprise compounds selected from sodium and potassium salts, including, but not limited to: bicarbonates, citrates and chloride salts, and combinations thereof. Specific examples of salts that can be used include, but are not limited to:
- sodium chloride,
- potassium chloride,
- sodium citrate (including monosodium citrate, disodium citrate and trisodium citrate),
- sodium bicarbonate, and
- combinations thereof.

In one embodiment a beverage or an additional drink of the invention comprises a suspending agent as defined herein.

In another embodiment, a beverage or an additional drink of the invention comprises a suspending agent selected from the group comprising, but not limited to:
- xanthan gum (including, for example, Grindsted® Xanthan Clear Easy A21191),
- guar gum,
- gelatine (derived from animal, fish, etc.),
- carrageenan (iota, lambda, kappa) (derived from seaweed),
- agar,
- alginate,
- locust bean gum,
- gum arabic,
- cellulose (including, for example, methyl-, carboxy methyl- and hydroxylpropyl methyl-cellulose),
- gellan,
- pectin, and
- combinations thereof.

The beverage may be water, a fruit juice based drink or a milk based drink. Examples of beverages include, but are not limited to:
- a diluted cordial drink;
- a milk based drink (including, for example: milk from a dairy source, soy/almond/rice/oat or coconut milk (non-dairy milks or plant derived milks), powdered milk that can be mixed with water, or long-life milk);
- a smoothie, (including, for example: a combination of: fruit and milk, fruit and water, yoghurt and fruit, or ice-cream and fruit);
- a protein shake (including, for example: a protein shake that uses a milk or water as a base for example a protein powder that is mixed with water or milk); and
- breakfast beverages.

In one embodiment the beverage is consumed by an individual prior to the individual taking part in a physical activity. In this embodiment the individual "pre-loads" with the resistant starch which is incorporated into the beverage. The presence of the resistant starch leads to the production of SCFAs. These SCFAs then aid in water and salt absorption in the large intestine. This allows a beverage, an oral rehydration solution, or similar solution, consumed at a later time, to be absorbed more effectively and enhance rehydration or maintain hydration in the individual. This means individuals taking part in sport are then able to maintain or restore their hydration levels during and following a physical activity.

In one embodiment the beverage is consumed by an individual at least 1, 2, 3, 4, 5, 6, 7, 8, 9, 10, 11, 12, 13, 14, 15 or 16 hours prior to the individual taking part in a physical activity.

An additional drink and/or an additional food item may be consumed in conjunction with the beverage, or before or after consumption of the beverage. For example the additional drink and/or an additional food may be consumed about 1, 2, 3, 4, 5, 6, 7 or 8, 9, 10, 11, 12, 13, 14, 15 or 16 hours after an individual has consumed a beverage of the invention, for example the additional drink and/or an additional food may be consumed during a physical activity or after the physical activity has concluded.

In one embodiment the food item is consumed by an individual prior to the individual taking part in a physical activity. In this embodiment the individual "pre-loads" with the resistant starch which is incorporated into the food item. As previously stated, the presence of the resistant starch leads to the production of SCFAs which in turn aid in water and salt absorption in the large intestine. This allows a beverage, an oral rehydration solution or a similar solution, or an additional drink, consumed at a later time (after consumption of the food item), to be absorbed more effectively and enhance rehydration or maintain hydration in the individual. This means individuals taking part in sport are then able to maintain or restore their hydration levels during and following a physical activity.

In one embodiment the food item is consumed by an individual at least 1, 2, 3, 4, 5, 6, 7, 8, 9, 10, 11, 12, 13, 14, 15 or 16 hours prior to the individual taking part in a physical activity.

Herein "food item" and "food items" encompasses solid and substantially solid items composed of a foodstuff that is eaten or taken into an organic body, for example a human or an animal, for nourishment. The "food item" or "food items" may comprise a starch comprising a resistant starch as defined herein. The food item may be in the form of, but not limited to: a bar, a biscuit, bread, cake, muffin, cookie, cereal, pasta, noodles, pancakes, waffles, pizza, yoghurt or an ice cream. Alternatively the food item may be in the form of a flour or a flour substitute, which could be used in the production of food items including, but not limited to: bars, breads, biscuits, cakes, muffins, cookies, cereals, pastas, noodles, pancakes, waffles, pizza bases, yoghurts or ice creams. In addition, the food item may be in the form of a tablet. For example an individual could consume one or more tablets 1, 2, 3, 4, 5, 6, 7, 8, 9, 10, 11, or 12 hours prior to taking part in a physical activity in order to rehydrate the individual or maintain hydration in the individual.

Herein "additional drink" and "additional drinks" encompasses liquids that are swallowed or taken into an organic body, for example a human or an animal.

In one embodiment the additional drink may be: water, a fruit juice based drink, or a milk based drink. Examples of additional drinks include, but are not limited to:
- a diluted cordial drink;
- a milk based drink (including, for example: milk from a dairy source, soy/almond/rice/oat or coconut milk (non-dairy milks or plant derived milks), powdered milk that can be mixed with water, or long-life milk);

a smoothie, (including, for example: a combination of: fruit and milk, fruit and water, yoghurt and fruit, or ice-cream and fruit);

a protein shake (including, for example: a protein shake that uses a milk or water as a base for example a protein powder that is mixed with water or milk); and breakfast beverages.

In one embodiment the additional drink or additional drinks may comprise a starch comprising a resistant starch as defined herein.

In an alternative embodiment the additional drink or additional drinks does not comprise a starch comprising a resistant starch as defined herein.

In one embodiment an additional drink is drunk after consumption of the beverage, for example at least 1, 2, 3, 4, 5, 6, 7, 8, 9, 10, 11, 12, 13, 14, 15 or 16 hours after an individual has consumed the beverage.

In one embodiment an additional drink or a beverage is drunk after consumption of the food item, for example at least 1, 2, 3, 4, 5, 6, 7, 8, 9, 10, 11, 12, 13, 14, 15 or 16 hours after an individual has consumed the food item.

In one embodiment the additional drink is an oral rehydration composition as defined herein.

In one embodiment the additional drink is a beverage as defined herein.

In one embodiment the additional food is consumed after consumption of the beverage, for example at least 1, 2, 3, 4, 5, 6, 7, 8, 9, 10, 11, 12, 13, 14, 15 or 16 hours after an individual has consumed the beverage.

In one embodiment to prevent an individual overhydrating their body, in one embodiment the beverage is consumed by an individual in combination with a food item or an additional drink, wherein the food item and the additional drink can comprise a starch that comprises resistant starch, as defined herein.

In another embodiment the additional food item comprises about 1 to about 300 g of starch comprising a resistant starch, preferably about 20 to about 100 g of starch comprising a resistant starch, more preferably about 25 to about 75 g of starch comprising a resistant starch. Exemplified ranges include but are not limited to: about 20 g to about 300 g of starch comprising a resistant starch; about 30 g to about 300 g of starch comprising a resistant starch; about 40 g to about 300 g of starch comprising a resistant starch; about 50 g to about 300 g of starch comprising a resistant starch; about 60 g to about 300 g of starch comprising a resistant starch; about 70 g to about 300 g of starch comprising a resistant starch; about 80 g to about 300 g of starch comprising a resistant starch; about 90 g to about 300 g of starch comprising a resistant starch; about 100 g to about 300 g of starch comprising a resistant starch; about 110 g to about 300 g of starch comprising a resistant starch; about 120 g to about 300 g of starch comprising a resistant starch; about 130 g to about 300 g of starch comprising a resistant starch; about 140 g to about 300 g of starch comprising a resistant starch; about 150 g to about 300 g of starch comprising a resistant starch; about 160 g to about 300 g of starch comprising a resistant starch; about 170 g to about 300 g of starch comprising a resistant starch; about 180 g to about 300 g of starch comprising a resistant starch; about 190 g to about 300 g of starch comprising a resistant starch; about 200 g to about 300 g of starch comprising a resistant starch; about 210 g to about 300 g of starch comprising a resistant starch; about 220 g to about 300 g of starch comprising a resistant starch; about 230 g to about 300 g of starch comprising a resistant starch; about 240 g to about 300 g of starch comprising a resistant starch; about 250 g to about 300 g of starch comprising a resistant starch; about 260 g to about 300 g of starch comprising a resistant starch; about 270 g to about 300 g of starch comprising a resistant starch; about 280 g to about 300 g of starch comprising a resistant starch; about 290 g to about 300 g of starch comprising a resistant starch; about 1 g to about 290 g of starch comprising a resistant starch; about 1 g to about 280 g of starch comprising a resistant starch; about 1 g to about 270 g of starch comprising a resistant starch; about 1 g to about 260 g of starch comprising a resistant starch; about 1 g to about 250 g of starch comprising a resistant starch; about 1 g to about 240 g of starch comprising a resistant starch; about 1 g to about 230 g of starch comprising a resistant starch; about 1 g to about 220 g of starch comprising a resistant starch; about 1 g to about 210 g of starch comprising a resistant starch; about 1 g to about 200 g of starch comprising a resistant starch; about 1 g to about 190 g of starch comprising a resistant starch; about 1 g to about 180 g of starch comprising a resistant starch; about 1 g to about 170 g of starch comprising a resistant starch; about 1 g to about 160 g of starch comprising a resistant starch; about 1 g to about 150 g of starch comprising a resistant starch; about 1 g to about 140 g of starch comprising a resistant starch; about 1 g to about 130 g of starch comprising a resistant starch; about 1 g to about 120 g of starch comprising a resistant starch; about 1 g to about 110 g of starch comprising a resistant starch; or about 1 g to about 100 g of starch comprising a resistant starch; about 1 g to about 90 g of starch comprising a resistant starch; about 1 g to about 80 g of starch comprising a resistant starch; about 1 g to about 70 g of starch comprising a resistant starch; about 1 g to about 60 g of starch comprising a resistant starch; about 1 g to about 50 g of starch comprising a resistant starch; about 1 g to about 40 g of starch comprising a resistant starch; about 1 g to about 30 g of starch comprising a resistant starch; about 1 g to about 20 g of starch comprising a resistant starch, or about 0.1 g, about 0.2 g, about 0.3 g, about 0.4 g, about 0.5 g, about 0.6 g, about 0.7 g, about 0.8 g, about 0.9 g, about 1 g, about 2 g, about 3 g, about 4 g, about 5 g, about 6 g, about 7 g, about 8 g, about 9 g or about 10 g of starch comprising a resistant starch.

In another embodiment the additional drink comprises about 50 to about 300 g of starch comprising a resistant starch, preferably about 100 to about 250 g of starch comprising a resistant starch, more preferably about 100 to about 200 g of starch comprising a resistant starch. Exemplified ranges include but are not limited to: about 100 to about 300 g of starch comprising a resistant starch; about 150 to about 300 g of starch comprising a resistant starch; about 200 to about 300 g of starch comprising a resistant starch; about 250 to about 300 g of starch comprising a resistant starch; about 50 to about 250 g of starch comprising a resistant starch; about 50 to about 200 g of starch comprising a resistant starch; about 50 to about 150 g of starch comprising a resistant starch; or about 50 to about 100 g of starch comprising a resistant starch.

In one embodiment a beverage the invention may optionally further comprise additional auxiliaries including, but not limited to:

colours, flavours (for example lemon, raspberry apple, blackcurrant, tropical, pineapple or orange flavourings, the flavourings may be provided by a commercial cordial), and sweeteners (including, but not limited to: sweeteners from both natural and artificial sources, sugars, sugar alcohols (polyols) and proteins, for example: natural sweeteners (for example mogrosides, glucose, fructose, sucrose and LoGicane™); amino acids (for example alanine, glycine, serine); artificial high intensity sweeteners (for example sucralose, alitame, cyclamate, aspartame, neotame, potassium acesulfame, and saccharin); natural high intensity sweeteners (for example, *Stevia rebaudiana*, Luo Han Guo, and glycyrrhizin from liquorice root); sweet-tasting proteins (for example, thaumatin from *Thaumatococcus daniellii*, monellin from *Dioscoreophyllum cumminsii*, brazzein from *Pentadiplandra brazzeana*, mabinlin and curculin); sugar alcohols—polyols or hydrogenated sugars— (for example sorbitol, xylitol, lactitol, mannitol, maltitol, isomalt and erythritol); and starch derived sweeteners (for example maltodextrins, glucose syrup, malto-oligosaccharides, tagatose and polydextrose). The sweetener may be chosen in order to contribute more than sweetness to a beverage or additional drink of the invention, for example body or mouth feel, reduced calories, or reduced osmotic effect. These exemplified sweeteners might be used alone or in combination to give the desired organoleptic appeal and physiological effect.

In one embodiment an additional drink of the invention may optionally further comprise additional auxiliaries including, but not limited to:
colours,
flavours (for example lemon, raspberry apple, blackcurrant, tropical, pineapple or orange flavourings, the flavourings may be provided by a commercial cordial), and
sweeteners (including, but not limited to: sweeteners from both natural and artificial sources, sugars, sugar alcohols (polyols) and proteins, for example: natural sweeteners (for example mogrosides, glucose, fructose, sucrose and LoGicane™); amino acids (for example alanine, glycine, serine); artificial high intensity sweeteners (for example sucralose, alitame, cyclamate, aspartame, neotame, potassium acesulfame, and saccharin); natural high intensity sweeteners (for example, *Stevia rebaudiana*, Luo Han Guo, and glycyrrhizin from liquorice root); sweet-tasting proteins (for example, thaumatin from *Thaumatococcus daniellii*, monellin from *Dioscoreophyllum cumminsii*, brazzein from *Pentadiplandra brazzeana*, mabinlin and curculin); sugar alcohols—polyols or hydrogenated sugars— (for example sorbitol, xylitol, lactitol, mannitol, maltitol, isomalt and erythritol); and starch derived sweeteners (for example maltodextrins, glucose syrup, malto-oligosaccharides, tagatose and polydextrose). The sweetener may be chosen in order to contribute more than sweetness to a beverage or additional drink of the invention, for example body or mouth feel, reduced calories, or reduced osmotic effect. These exemplified sweeteners might be used alone or in combination to give the desired organoleptic appeal and physiological effect.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Throughout this specification, the term "consisting essentially of" is intended to exclude elements which would materially affect the properties of the claimed composition.

EXAMPLE EMBODIMENTS OF THE INVENTION

A. An oral rehydration composition comprising:
a salt composition;
at least one substance selected from the group consisting of:
   a starch comprising a resistant starch;
   a dietary fibre;
   other starches or starch containing materials; and
   combinations thereof;
a suspending agent in an amount effective to suspend the at least one substance in water; and
optionally one or more of:
   glucose;
   water soluble salts of zinc, magnesium or copper;
   sodium bicarbonate; and
   combinations thereof.

B. The oral rehydration composition according to example embodiment A, wherein the starch comprising a resistant starch is selected from the group consisting of: an RS1, RS2, RS3, RS4 or RS5 starch, or combinations thereof.

C. The oral rehydration composition according to example embodiment A, wherein the dietary fibre is selected from the group consisting of: *psyllium*; inulin; oligosaccharides, such as fructo-, galacto-, malto-, isomalto-, gentio-, agaro, neoagaro-, α-gluco-, β-gluco-, cyclo-, inulo-, glycosyl sucrose, latulose, lactosucrose, or xylosucrose; bran, pericarp, endosperm, or cell wall material from cereals such as wheat, triticale, sorghum, mile, rice, sago, potato, tapioca, cassava, oats, barley, and corn, or pulses, such as peas and lupins, and the like, which may be further processed or modified, such as by bleaching, and combinations thereof.

D. The oral rehydration composition according to example embodiment A, wherein the other starches or starch containing materials is selected from the group consisting of: plant components, such as, grain, tuber, seeds, and the like, which may be physically, enzymatically or chemically modified, such as through the processes of dextrinisation or dry roasting in the presence or absence of a catalyst such as hydrochloric, nitric, sulfuric acid, and combinations thereof.

E. The oral rehydration composition according to example embodiment A or example embodiment B, wherein the starch comprising a resistant starch is selected from the group consisting of:
   a class V high amylose maize starch;
   a class VI high amylose maize starch;
   a class VII high amylose maize starch
   a class VIII high amylose maize starch;
   a class IX high amylose maize starch;
   a class X high amylose maize starch;
   a type IV resistant starch;
   a type V resistant starch; and
   combinations thereof.

F. An oral rehydration composition comprising:
a salt composition;
at least one substance selected from the group consisting of:
   a class V high amylose maize starch;
   a class VI high amylose maize starch;
   a class VII high amylose maize starch
   a class VIII high amylose maize starch;
   a class IX high amylose maize starch;
   a class X high amylose maize starch;
   a type IV resistant starch;
   a type V resistant starch; and
   combinations thereof;

a suspending agent in an amount effective to suspend the at least one substance in water; and
optionally one or more of:
glucose;
water soluble salts of zinc, magnesium or copper;
sodium bicarbonate; or
combinations thereof.

G. An oral rehydration composition consisting essentially of:
a salt composition;
a starch comprising a resistant starch;
a suspending agent in an amount effective to suspend the starch comprising a resistant starch in water; and
optionally one or more of:
water soluble salts of zinc, magnesium or copper;
sodium bicarbonate; and
combinations thereof.

H. The oral rehydration composition of example embodiment E, wherein the starch comprising a resistant starch is selected from the group consisting of:
a class V high amylose maize starch;
a class VI high amylose maize starch;
a class VII high amylose maize starch
a class VIII high amylose maize starch;
a class IX high amylose maize starch;
a class X high amylose maize starch;
a type IV resistant starch;
a type V resistant starch; and
combinations thereof.

I. The oral rehydration composition according to any one of example embodiments E, F or H, wherein the type IV resistant starch is a resistant starch material that has been exposed to a chemical process selected from the group consisting of:
a thermal or hydrothermal treatment;
an enzymatic modification;
an oxidation or bleaching process;
a cross-bonding or crosslinking process;
treatment with propylene oxide;
treatment with glycerol;
an etherification process;
an esterification (or acylation) process;
an acidification process;
an alkalisation process;
a dextrinisation process;
a phosphorylation process; and
combinations thereof,
to produce the type IV resistant starch.

J. The oral rehydration composition according to any one of example embodiments E, F, H or I, wherein the type IV resistant starch is selected from the group consisting of:
a retrograded gelatinised class VII high amylose maize starch;
a starch comprising a resistant starch that is acetylated;
a starch comprising a resistant starch that is acylated;
a bleached starch material;
an oxidised starch material;
an acid treated starch material;
an alkaline treated starch material
a phosphorylated starch material;
acetylated tapioca starch;
acetylated rice starch; and
combinations thereof.

K. The oral rehydration composition according to any one of example embodiments E, F or H, wherein the starch comprising a resistant starch is a type V resistant starch.

L. The oral rehydration composition according to any one of example embodiments A to K, wherein the salt composition comprises one or more than one of:
sodium chloride;
potassium chloride; and
trisodium citrate (dihydrate).

M. The oral rehydration composition according to any one of example embodiments A to L, wherein:
the salt composition comprises sodium chloride, wherein the sodium chloride is present in an amount in a range of from about 0.8 g/L to about 5.2 g/L, or in an amount in a range from about 2 g/L to about 3 g/L, or in an amount from about 2.4 g/L to about 2.8 g/L, when the oral rehydration composition is added to water; and/or
the salt composition comprises potassium chloride, wherein the potassium chloride is present in an amount in a range of from about 0.2 g/L to about 2 g/L, or in an amount in a range from about 0.8 g/L to about 1.9 g/L, or in an amount from about 1.4 g/L to about 1.6 g/L, when the oral rehydration composition is added to water; and/or
the salt composition comprises trisodium citrate (dihydrate), wherein the trisodium citrate (dihydrate) is present in an amount in a range of from about 0 g/L to about 3.4 g/L, or in an amount in a range from about 1.0 g/L to about 3.2 g/L, or in an amount from about 2.7 g/L to about 3.1 g/L, when the oral rehydration composition is added to water.

N. The oral rehydration composition according to any one of example embodiments A to L, wherein the oral rehydration composition comprises sodium in an amount in a range of about 450 mg/L to about 800 mg/L, when the oral rehydration composition is added to water.

O. The oral rehydration composition according to any one of example embodiments A to L or N, wherein the oral rehydration composition comprises potassium in an amount in a range of about 100 mg/L to about 400 mg/L, when the oral rehydration composition is added to water.

P. The oral rehydration composition according to any one of example embodiments A to O, wherein the starch comprising a resistant starch is present in an amount in a range of from about 10 g/L to about 80 g/L, or in an amount in a range from about 35 g/L to about 60 g/L, or in an amount from about 45 g/L to about 55 g/L, when the oral rehydration composition is added to water.

Q. The oral rehydration composition according to example embodiment A or example embodiment D, the wherein the other starches and starch containing materials is present in an amount in a range of from about 3 g/L to about 80 g/L, or in an amount in a range from about 35 g/L to about 60 g/L, or in an amount in a range from about 45 g/L to about 55 g/L, when the oral rehydration composition is added to water.

R. The oral rehydration composition according to example embodiment A or example embodiment C, wherein the dietary fibre is present in an amount in a range of from about 3 g/L to about 80 g/L, or in an amount in a range from about 35 g/L to about 60 g/L, or in an amount in a range from about 45 g/L to about 55 g/L, when the oral rehydration composition is added to water.

S. The oral rehydration composition according to any one of example embodiments A to R, wherein the suspending agent is selected from the group consisting of:
xanthan gum;
guar gum;
gelatine;
carrageenan;

agar;
alginate;
locust bean gum;
gum arabic;
cellulose (including methyl-, carboxy methyl-, and hydroxylpropyl methyl-cellulose);
gellan;
pectin; and
combinations thereof.

T. The oral rehydration composition according to example embodiment S, wherein:
the xanthan gum is present in an amount in a range of from about 0.5 g/L to about 5.0 g/L, or in an amount in a range from about 1 g/L to about 2.5 g/L, or in an amount from about 1.5 g/L to about 2.25 g/L; and/or
guar gum is present in an amount in a range of from about 1.0 g/L to about 10.0 g/L, or in an amount in a range from about 2.0 g/L to about 6.0 g/L, or in an amount from about 3.0 g/L to about 5.0 g/L; and/or
gelatine is present in an amount in a range of from about 5 g/L to about 20 g/L, or in an amount in a range from about 7 g/L to about 17.5 g/L, or in an amount from about 10.0 g/L to about 15.0 g/L; and/or
carrageenan is present in an amount in a range of from about 5 g/L to about 15 g/L, or in an amount in a range from about 6 g/L to about 12 g/L, or in an amount from about 7.5 g/L to about 10.0 g/L; and/or
agar is present in an amount in a range of from about 3 g/L to about 15 g/L, or in an amount in a range from about 4 g/L to about 12 g/L, or in an amount from about 5.0 g/L to about 10.0 g/L; and/or
alginate is present in an amount in a range of from about 3 g/L to about 15 g/L, or in an amount in a range from about 4 g/L to about 12 g/L, or in an amount from about 5.0 g/L to about 10.0 g/L; and/or
locust bean gum is present in an amount in a range of from about 3 g/L to about 15 g/L, or in an amount in a range from about 4 g/L to about 12 g/L, or in an amount from about 5.0 g/L to about 10.0 g/L; and/or
gum Arabic is present in an amount in a range of from about 5 g/L to about 25 g/L, or in an amount in a range from about 7 g/L to about 20 g/L, or in an amount from about 10.0 g/L to about 20.0 g/L; and/or
cellulose (including methyl-, carboxy methyl-, and hydroxylpropyl methyl-cellulose), is present in an amount in a range of from about 5 g/L to about 20 g/L, or in an amount in a range from about 6 g/L to about 15 g/L, or in an amount from about 7.5 g/L to about 12.0 g/L; and/or
gellan is present in an amount in a range of from about 2 g/L to about 15 g/L, or in an amount in a range from about 4 g/L to about 12 g/L, or in an amount from about 5.0 g/L to about 10.0 g/L; and/or
pectin is present in an amount in a range of from about 2 g/L to about 25 g/L, or in an amount in a range from about 3 g/L to about 20 g/L, or in an amount from about 3.5 g/L to about 10.0 g/L,
when an oral rehydration composition of the invention is added to water.

U. The oral rehydration composition according to any one of example embodiments A to T, wherein the suspending agent is xanthan gum.

V. The oral rehydration composition according to any one of example embodiments A to U, wherein water soluble salts of zinc, magnesium or copper are selected from the group consisting of:
zinc acetate;
zinc picolinate;
zinc gluconate;
magnesium chloride;
copper sulphate; and
combinations thereof.

W. The oral rehydration composition according to example embodiment V, wherein:
zinc acetate if present is present in an amount to provide elemental zinc in a range from about 1 mg/L to about 10 mg/L, or in an amount in a range from about 4 mg/L to about 7 mg/L, or in an amount in a range from about 5 mg/L to about 6 mg/L; and/or
zinc gluconate if present is present in an amount to provide elemental zinc in a range from about 1 mg/L to about 10 mg/L, or in an amount in a range from about 4 mg/L to about 7 mg/L, or in an amount in a range from about 5 mg/L to about 6 mg/L; and/or
zinc picolinate if present is present in an amount to provide elemental zinc in a range from about 1 mg/L to about 10 mg/L, or in an amount in a range from about 4 mg/L to about 7 mg/L, or in an amount in a range from about 5 mg/L to about 6 mg/L; and/or
magnesium chloride if present is present in an amount to provide elemental magnesium in a range from about 3 mg/L to about 7.8 mg/L, or in an amount in a range from about 4 mg/L to about 7 mg/L, or in an amount in a range from about 5 mg/L to about 6 mg/L; and/or
copper sulphate is present in an amount to provide elemental copper in a range from about 1 mg/L to about 4 mg/L, or in an amount in a range from about 2 mg/L to about 3 mg/L, or in an amount in a range from about 2.2 mg/L to about 2.8 mg/L; and/or
sodium bicarbonate if present is present in a range from about 0 g/L to about 3 g/L, or in an amount in a range from about 2.2 g/L to about 2.8 g/L, or in an amount from about 2.4 g/L to about 2.6 g/L; and/or
glucose if present is present in an amount in a range from about 1 g/L to about 25 g/L, or in an amount in a range from about 2 g/L to about 13 g/L, or in an amount in a range from about 2 g/L to about 8 g/L,
when an oral rehydration composition of the invention is added to water.

X. An aqueous composition comprising an oral rehydration composition according to any one of example embodiments A to W, and water.

Y. An aqueous composition comprising an oral rehydration composition according to any one of example embodiments A to W, and water, wherein the aqueous composition rehydrates an individual affected by dehydration.

Z. The aqueous composition according to example embodiment Y, wherein the dehydration is caused wholly or partially by diarrhoea.

AA. The aqueous composition according to example embodiment Y, wherein the dehydration is caused by the individual engaging in a physical activity.

AB. The aqueous composition according to example embodiment AA, wherein the physical activity is a sport.

AC. A method of making an oral rehydration solution according to any one of example embodiments A to W, the method comprising the step of adding the oral rehydration composition to water.

AD. A method of rehydrating an individual suffering from dehydration, wherein the method comprises administering an effective amount of the oral rehydration composition according to any one of example embodiments A to W to the individual.

AE. A method of rehydrating an individual suffering from dehydration, wherein the method comprises administering an effective amount of the aqueous composition according to any one of example embodiments X to AB to the individual.

AF. The method according to example embodiment AD or example embodiment AE, wherein the dehydration is caused wholly or partially by diarrhoea.

AG. The method according to example embodiment AD or example embodiment AE, wherein the dehydration is caused by the individual engaging in a physical activity.

AH. The method according to example embodiment AG, wherein the physical activity is a sport.

AI. A method of rehydrating an individual suffering from dehydration, the method comprising a step of administering an effective amount of an oral rehydration composition that comprises:
   a salts composition;
   a starch comprising a resistant starch;
   a suspending agent in an amount effective to suspend the starch comprising a
   resistant starch; and
   optionally one or more of:
      glucose;
      water soluble salts of zinc, magnesium or copper;
      sodium bicarbonate; or
      combinations thereof.

AJ. The method of example embodiment AI, wherein the starch comprising a resistant starch is selected from the group consisting of:
   a class V high amylose maize starch;
   a class VI high amylose maize starch;
   a class VII high amylose maize starch
   a class VIII high amylose maize starch;
   a class IX high amylose maize starch;
   a class X high amylose maize starch;
   a type IV resistant starch;
   a type V resistant starch; and
   combinations thereof.

AK. The method according to example embodiment AJ, wherein the type IV resistant starch is a resistant starch material that has been exposed to a chemical process selected from the group consisting of:
   a thermal or hydrothermal treatment;
   an enzymatic modification;
   an oxidation or bleaching process;
   a cross-bonding or crosslinking process;
   treatment with propylene oxide;
   treatment with glycerol;
   an etherification process;
   an esterification (or acylation) process;
   an acidification process;
   an alkalisation process;
   a dextrinisation process;
   a phosphorylation process; and
   combinations thereof,
   to produce the type IV resistant starch.

AL. The method according to any one of example embodiments AJ or AK, wherein the type IV resistant starch is selected from the group consisting of:
   a retrograded gelatinised class VII high amylose maize starch;
   a starch comprising a resistant starch that is acetylated;
   a starch comprising a resistant starch that is acylated;
   a bleached starch material;
   an oxidised starch material;
   an acid treated starch material;
   an alkaline treated starch material
   a phosphorylated starch material;
   acetylated tapioca starch;
   acetylated rice starch; and
   combinations thereof.

AM. The method according to example embodiment AJ, wherein the starch comprising a resistant starch is a type V resistant starch.

AN. The method according to any one of example embodiments AJ to AM, wherein the salts composition comprises one or more compounds selected from the group consisting of:
   sodium chloride;
   potassium chloride; and
   trisodium citrate (dihydrate).

AO. The method according to any one of example embodiments AJ to AN, wherein the suspending agent is selected from the group consisting of:
   xanthan gum;
   guar gum;
   gelatine;
   carrageenan;
   agar;
   alginate;
   locust bean gum;
   gum arabic;
   cellulose;
   gellan;
   pectin; and
   combinations thereof.

AP. The method according to any one of example embodiments AJ to AO, wherein the dehydration is caused wholly or partially by diarrhoea.

AQ. The method according to any one of example embodiments AJ to AO, wherein the dehydration is caused by the individual engaging in a physical activity.

AR. The method according to example embodiment AQ, wherein the physical activity is a sport.

AS. An oral rehydration composition according to any one of example embodiments A to W when used to rehydrate an individual affected by dehydration.

AT. An aqueous composition according to example embodiment X when used to rehydrate an individual affected by dehydration.

AU. The oral rehydration composition of example embodiment AS or the aqueous composition of example embodiment AT, wherein the dehydration is caused wholly or partially by diarrhoea.

AV. The oral rehydration composition of example embodiment AS or the aqueous composition of example embodiment AT, wherein the dehydration is caused by the individual engaging in a physical activity.

AW. The oral rehydration composition or the aqueous composition of example embodiment AV, wherein the physical activity is a sport.

AX. Use of an oral rehydration composition according to any one of example embodiments A to W in the formation of an aqueous oral rehydration solution for rehydrating an individual affected by dehydration.

AY. Use of an aqueous composition according to example embodiment X for rehydrating an individual affected by dehydration.

AZ. The use of according to example embodiment AX or example embodiment AY, wherein the dehydration is caused wholly or partially by diarrhoea.

BA. The use according to example embodiment AX or example embodiment AY, wherein the dehydration is caused by the individual engaging in a physical activity.

BB. The use according to example embodiment BA, wherein the physical activity is a sport.

BC. Use of an oral rehydration composition to rehydrate an individual suffering from dehydration, the oral rehydration composition comprising:
  a salts composition;
  a starch comprising a resistant starch;
  a suspending agent in an amount effective to suspend the starch comprising a
  resistant starch; and
  optionally one or more of:
    glucose;
    water soluble salts of zinc, magnesium or copper;
    sodium bicarbonate; or
    combinations thereof.

BD. The use of example embodiment BC, wherein the starch comprising a resistant starch is selected from the group consisting of:
  a class V high amylose maize starch;
  a class VI high amylose maize starch;
  a class VII high amylose maize starch
  a class VIII high amylose maize starch;
  a class IX high amylose maize starch;
  a class X high amylose maize starch;
  a type IV resistant starch;
  a type V resistant starch; and
  combinations thereof.

BE. The use according to example embodiment BD, wherein the type IV resistant starch is a resistant starch material that has been exposed to a chemical process selected from the group consisting of:
  a thermal or hydrothermal treatment;
  an enzymatic modification;
  an oxidation or bleaching process;
  a cross-bonding or crosslinking process;
  treatment with propylene oxide;
  treatment with glycerol;
  an etherification process;
  an esterification (or acylation) process;
  an acidification process;
  an alkalisation process;
  a dextrinisation process;
  a phosphorylation process; and
  combinations thereof,
  to produce the type IV resistant starch.

BF. The use according to any one of example embodiments BD or BE, wherein the type IV resistant starch is selected from the group consisting of:
  a retrograded gelatinised class VII high amylose maize starch;
  a starch comprising a resistant starch that is acetylated;
  a starch comprising a resistant starch that is acylated;
  a bleached starch material;
  an oxidised starch material;
  an acid treated starch material;
  an alkaline treated starch material
  a phosphorylated starch material;
  acetylated tapioca starch;
  acetylated rice starch; and
  combinations thereof.

BG. The use according to example embodiment BC or example embodiment BD, wherein the starch comprising a resistant starch is a type V resistant starch.

BH. The use according to any one of example embodiments BC to BG, wherein the salts composition comprises one or more compounds selected from the group consisting of:
  sodium chloride;
  potassium chloride; and
  trisodium citrate (dihydrate).

BI. The use according to any one of example embodiments BC to BH, wherein the suspending agent is selected from the group consisting of:
  xanthan gum;
  guar gum;
  gelatine;
  carrageenan;
  agar;
  alginate;
  locust bean gum;
  gum arabic;
  cellulose;
  gellan;
  pectin; and
  combinations thereof.

BJ. The use of according to any one of example embodiments BC to BI, wherein the dehydration is caused wholly or partially by diarrhoea.

BK. The use according to any one of example embodiments BC to BI, wherein the dehydration is caused by the individual engaging in a physical activity.

BL. The use according to example embodiment BK, wherein the physical activity is a sport.

BM. A beverage comprising a resistant starch, wherein the beverage is formulated for an individual to consume before, during or after the individual engages in a physical activity.

BN. The beverage of example embodiment BM, wherein the starch comprising a resistant starch is selected from the group consisting of:
  a class V high amylose maize starch;
  a class VI high amylose maize starch;
  a class VII high amylose maize starch
  a class VIII high amylose maize starch;
  a class IX high amylose maize starch;
  a class X high amylose maize starch;
  a type IV resistant starch;
  a type V resistant starch; and
  combinations thereof.

BO. A beverage comprising a resistant starch selected from the group consisting of:
  a class V high amylose maize starch;
  a class VI high amylose maize starch;
  a class VII high amylose maize starch
  a class VIII high amylose maize starch;
  a class IX high amylose maize starch;
  a class X high amylose maize starch;
  a type IV resistant starch;
  a type V resistant starch; and
  combinations thereof,
  wherein the beverage is formulated for an individual to consume before, during or after the individual engages in a physical activity.

BP. The beverage according to example embodiment BN or example embodiment BO, wherein the type IV resistant starch is a resistant starch material that has been exposed to a chemical process selected from the group consisting of:
  a thermal or hydrothermal treatment;
  an enzymatic modification;
  an oxidation or bleaching process;
  a cross-bonding or crosslinking process;
  treatment with propylene oxide;
  treatment with glycerol;
  an etherification process;
  an esterification (or acylation) process;

an acidification process;
an alkalisation process;
a dextrinisation process;
a phosphorylation process; and
combinations thereof,
to produce the type IV resistant starch.

BQ. The beverage according to any one of example embodiments BN to BP, wherein the type IV resistant starch is selected from the group consisting of:
   a retrograded gelatinised class VII high amylose maize starch;
   a starch comprising a resistant starch that is acetylated;
   a starch comprising a resistant starch that is acylated;
   a bleached starch material;
   an oxidised starch material;
   an acid treated starch material;
   an alkaline treated starch material
   a phosphorylated starch material;
   acetylated tapioca starch;
   acetylated rice starch; and
   combinations thereof.

BR. The beverage according to example embodiment BN or example embodiment BO, wherein the starch comprising a resistant starch is a type V resistant starch.

BS. The beverage according to any one of example embodiments BM to BR further comprising a salt composition.

BT. The beverage according to any one of example embodiments BM to BS, further comprising a salt composition comprising one or more than one of:
   sodium chloride;
   potassium chloride; and
   trisodium citrate (dihydrate).

BU. The beverage according to any one of example embodiments BS or BT, wherein:
   the salt composition comprises sodium chloride, wherein the sodium chloride is present in an amount in a range of from about 0.8 g/L to about 5.2 g/L, or in an amount in a range from about 2 g/L to about 3 g/L, or in an amount from about 2.4 g/L to about 2.8 g/L; and/or
   the salt composition comprises potassium chloride, wherein the potassium chloride is present in an amount in a range of from about 0.2 g/L to about 2 g/L, or in an amount in a range from about 0.8 g/L to about 1.9 g/L, or in an amount from about 1.4 g/L to about 1.6 g/L; and/or
   the salt composition comprises trisodium citrate (dihydrate), wherein the trisodium citrate (dihydrate) is present in an amount in a range of from about 0 g/L to about 3.4 g/L, or in an amount in a range from about 1.0 g/L to about 3.2 g/L, or in an amount from about 2.7 g/L to about 3.1 g/L.

BV. The beverage according to any one of example embodiments BS or BT, comprising sodium in an amount in a range of about 450 mg/L to about 800 mg/L.

BW. The beverage according to any one of example embodiments BS, BT or BV, comprising potassium in an amount in a range of about 100 mg/L to about 400 mg/L.

BX. The beverage according to any one of example embodiments BM to BW further comprising a suspending agent.

BY. The beverage according to any one of example embodiments BM to BW, further comprising a suspending agent selected from the group consisting of:
   xanthan gum;
   guar gum;
   gelatine;
   carrageenan;
   agar;
   alginate;
   locust bean gum;
   gum arabic;
   cellulose (including methyl-, carboxy methyl-, and hydroxylpropyl methyl-cellulose);
   gellan;
   pectin; and
   combinations thereof.

BZ. The oral rehydration composition according to example embodiment BY, wherein:
   the xanthan gum is present in an amount in a range of from about 0.5 g/L to about 5.0 g/L, or in an amount in a range from about 1 g/L to about 2.5 g/L, or in an amount from about 1.5 g/L to about 2.25 g/L; and/or
   guar gum is present in an amount in a range of from about 1.0 g/L to about 10.0 g/L, or in an amount in a range from about 2.0 g/L to about 6.0 g/L, or in an amount from about 3.0 g/L to about 5.0 g/L; and/or
   gelatine is present in an amount in a range of from about 5 g/L to about 20 g/L, or in an amount in a range from about 7 g/L to about 17.5 g/L, or in an amount from about 10.0 g/L to about 15.0 g/L; and/or
   carrageenan is present in an amount in a range of from about 5 g/L to about 15 g/L, or in an amount in a range from about 6 g/L to about 12 g/L, or in an amount from about 7.5 g/L to about 10.0 g/L; and/or
   agar is present in an amount in a range of from about 3 g/L to about 15 g/L, or in an amount in a range from about 4 g/L to about 12 g/L, or in an amount from about 5.0 g/L to about 10.0 g/L; and/or
   alginate is present in an amount in a range of from about 3 g/L to about 15 g/L, or in an amount in a range from about 4 g/L to about 12 g/L, or in an amount from about 5.0 g/L to about 10.0 g/L; and/or
   locust bean gum is present in an amount in a range of from about 3 g/L to about 15 g/L, or in an amount in a range from about 4 g/L to about 12 g/L, or in an amount from about 5.0 g/L to about 10.0 g/L; and/or
   gum Arabic is present in an amount in a range of from about 5 g/L to about 25 g/L, or in an amount in a range from about 7 g/L to about 20 g/L, or in an amount from about 10.0 g/L to about 20.0 g/L; and/or
   cellulose (including methyl-, carboxy methyl-, and hydroxylpropyl methyl-cellulose), is present in an amount in a range of from about 5 g/L to about 20 g/L, or in an amount in a range from about 6 g/L to about 15 g/L, or in an amount from about 7.5 g/L to about 12.0 g/L; and/or
   gellan is present in an amount in a range of from about 2 g/L to about 15 g/L, or in an amount in a range from about 4 g/L to about 12 g/L, or in an amount from about 5.0 g/L to about 10.0 g/L; and/or
   pectin is present in an amount in a range of from about 2 g/L to about 25 g/L, or in an amount in a range from about 3 g/L to about 20 g/L, or in an amount from about 3.5 g/L to about 10.0 g/L.

CA. The beverage according to any one of example embodiments BM to BZ, further comprising one or more of:
   glucose;
   one or more water soluble salts of zinc, magnesium or copper; and
   sodium bicarbonate.

CB. The beverage according to example embodiment CA, wherein water soluble salts of zinc, magnesium or copper are selected from the group consisting of:

zinc acetate;
zinc picolinate;
zinc gluconate;
magnesium chloride;
copper sulphate; and
combinations thereof.

CC. The beverage composition according to example embodiment CB, wherein:
  zinc acetate if present is present in an amount to provide elemental zinc in a range from about 1 mg/L to about 10 mg/L, or in an amount in a range from about 4 mg/L to about 7 mg/L, or in an amount in a range from about 5 mg/L to about 6 mg/L; and/or
  zinc gluconate if present is present in an amount to provide elemental zinc in a range from about 1 mg/L to about 10 mg/L, or in an amount in a range from about 4 mg/L to about 7 mg/L, or in an amount in a range from about 5 mg/L to about 6 mg/L; and/or
  zinc picolinate if present is present in an amount to provide elemental zinc in a range from about 1 mg/L to about 10 mg/L, or in an amount in a range from about 4 mg/L to about 7 mg/L, or in an amount in a range from about 5 mg/L to about 6 mg/L; and/or
  magnesium chloride if present is present in an amount to provide elemental magnesium in a range from about 3 mg/L to about 7.8 mg/L, or in an amount in a range from about 4 mg/L to about 7 mg/L, or in an amount in a range from about 5 mg/L to about 6 mg/L; and/or
  copper sulphate is present in an amount to provide elemental copper in a range from about 1 mg/L to about 4 mg/L, or in an amount in a range from about 2 mg/L to about 3 mg/L, or in an amount in a range from about 2.2 mg/L to about 2.8 mg/L; and/or
  sodium bicarbonate if present is present in a range from about 0 g/L to about 3 g/L, or in an amount in a range from about 2.2 g/L to about 2.8 g/L, or in an amount from about 2.4 g/L to about 2.6 g/L; and/or
  glucose if present is present in an amount in a range from about 1 g/L to about 25 g/L, or in an amount in a range from about 2 g/L to about 13 g/L, or in an amount in a range from about 2 g/L to about 8 g/L.

CD. A beverage comprising an oral rehydration composition according to any one of example embodiments A to W that is formulated for an individual to consume before, during or after the individual engages in a physical activity.

CE. The beverage according to any one of example embodiments BM to CD, wherein the beverage is selected from the group consisting of:
  a diluted cordial drink;
  a milk based drink (including, for example: milk from a dairy source, soy/almond/rice/oat or coconut milk (non-dairy milks or plant derived milks), powdered milk that can be mixed with water, or long-life milk);
  a smoothie, (including, for example: a combination of: fruit and milk, fruit and water, yoghurt and fruit, or ice-cream and fruit);
  a protein shake (including, for example: a protein shake that uses a milk or water as a base for example a protein powder that is mixed with water or milk); and
  breakfast beverages.

CF. The beverage according to any one of example embodiments BM to CE, wherein the physical activity is a sport.

CG. The beverage according to any one of example embodiments BM to CF, wherein the beverage is consumed before the individual engages in the physical activity.

CH. The beverage according to any one of example embodiments BM to CG, wherein the beverage is consumed at least about 1, 2, 3, 4, 5, 6, 7, 8, 9, 10, 11, 12, 13, 14, 15 or 16 hours before the individual engages in the physical activity.

CI. The beverage according to any one of example embodiments BM to CH, wherein the beverage is consumed at least about 1, 2, 3, 4, 5, 6, 7, 8, 9, 10, 11, 12, 13, 14, 15 or 16 hours before the individual engages in the physical activity.

CJ. The beverage according to any one of example embodiments BM to CI, wherein the individual consumes a food item and/or an additional drink, in combination with consumption of the beverage.

CK. The beverage according to example embodiment CJ, wherein the food item comprises a starch comprising a resistant starch.

CL. The beverage according to example embodiment CJ, wherein the additional drink comprises a starch comprising a resistant starch.

CM. The beverage according to example embodiment CJ or example embodiment CL, wherein the additional drink is selected from the group consisting of:
  a diluted cordial drink;
  a milk based drink (including, for example: milk from a dairy source, soy/almond/rice/oat or coconut milk (non-dairy milks or plant derived milks), powdered milk that can be mixed with water, or long-life milk);
  a smoothie, (including, for example: a combination of: fruit and milk, fruit and water, yoghurt and fruit, or ice-cream and fruit);
  a protein shake (including, for example: a protein shake that uses a milk or water as a base for example a protein powder that is mixed with water or milk); and
  breakfast beverages.

CN. The beverage according to any one of example embodiments CJ to CM, wherein the food item and/or the additional drink is consumed before, during or after the individual engages in the physical activity.

CO. The beverage according to any one of example embodiments CJ to CN, wherein the food item and/or the additional drink is consumed before or after the individual consumes the beverage.

CP. The beverage according to any one of example embodiments CJ to CO, wherein the food item and/or the additional drink is consumed at least about 1, 2, 3, 4, 5, 6, 7, 8, 9, 10, 11, 12, 13, 14, 15 or 16 hours after consumption of the beverage.

CQ. The beverage according to any one of example embodiments CJ to CP, wherein the additional drink is a beverage according to any one of example embodiments BM to BT or an oral rehydration composition according to any one of example embodiments A to W.

CR. The beverage according to any one of example embodiments BM to CQ, wherein the individual is suffering from dehydration.

CS. The beverage according to example embodiment CR, wherein the dehydration is caused wholly or partially by diarrhoea.

CT. A food item comprising a resistant starch selected from the group consisting of:
  a class V high amylose maize starch;
  a class VI high amylose maize starch;
  a class VII high amylose maize starch
  a class VIII high amylose maize starch;
  a class IX high amylose maize starch;
  a class X high amylose maize starch;

a type IV resistant starch;
a type V resistant starch; and
combinations thereof,
wherein the food item is formulated for an individual to consume before, during or after the individual engages in a physical activity.

CU. The food item according to example embodiment CT, wherein the type IV resistant starch is a resistant starch material that has been exposed to a chemical process selected from the group consisting of:
a thermal or hydrothermal treatment;
an enzymatic modification;
an oxidation or bleaching process;
a cross-bonding or crosslinking process;
treatment with propylene oxide;
treatment with glycerol;
an etherification process;
an esterification (or acylation) process;
an acidification process;
an alkalisation process;
a dextrinisation process;
a phosphorylation process; and
combinations thereof,
to produce the type IV resistant starch.

CV. The food item according to example embodiment CT, wherein the starch comprising a resistant starch is a type V resistant starch.

CW. The food item according to any one of example embodiments CT to CV, wherein the food item is formulated in a form selected from the group consisting of:
a bar,
bread,
a biscuit,
a cake,
a muffin,
a cookie,
a cereal,
pasta,
noodles,
pancakes, waffles,
pizza,
yoghurt,
ice cream
a flour or a flour substitute, which can be used in the production of food items including, but not limited to: bars, biscuits, breads, cakes, muffins, cookies, cereals, pastas, noodles, pancakes, waffles, pizza bases, yoghurts or ice creams, or
a tablet.

CX. The food item according to any one of example embodiments CT to CW further comprising a salt composition.

CY. The food item according to any one of example embodiments CT to CX, further comprising a salt composition comprising one or more than one of:
sodium chloride;
potassium chloride; and
trisodium citrate (dihydrate).

CZ. The food item according to any one of example embodiments CT to CY, wherein the physical activity is a sport.

DA. The food item according to any one of example embodiments CT to CZ, wherein the food item is consumed before the individual engages in the physical activity.

DB. The food item according to any one of example embodiments CT to DA, wherein the food item is consumed at least 1, 2, 3, 4, 5, 6, 7, 8, 9, 10, 11, 12, 13, 14, 15 or 16 before the individual engages in the physical activity.

DC. The food item according to any one of example embodiments CT to DB, wherein the individual consumes a beverage according to any one of example embodiments BM to CE and/or an additional drink, in combination with consumption of the food item.

DD. The food item according to example embodiment DC, wherein the additional drink comprises a starch comprising a resistant starch.

DE. The food item according to example embodiment DC or example embodiment DD, wherein the additional drink is selected from the group consisting of:
a diluted cordial drink;
a milk based drink (including, for example: milk from a dairy source, soy/almond/rice/oat or coconut milk (non-dairy milks or plant derived milks), powdered milk that can be mixed with water, or long-life milk);
a smoothie, (including, for example: a combination of: fruit and milk, fruit and water, yoghurt and fruit, or ice-cream and fruit);
a protein shake (including, for example: a protein shake that uses a milk or water as a base for example a protein powder that is mixed with water or milk); and
breakfast beverages.

DF. The food item according to any one of example embodiments DC to DE, wherein the beverage and/or the additional drink is consumed at least about 1, 2, 3, 4, 5, 6, 7, 8, 9, 10, 11, 12, 13, 14, 15 or 16 hours after consumption of the food item.

DG. The food item according to any one of example embodiments CT to DF, wherein the individual is suffering from dehydration.

DH. The food item according to example embodiment DG, wherein the dehydration is caused wholly or partially by diarrhoea.

DI. Use of a starch comprising a resistant starch in a composition to maintain hydration in an individual and/or rehydrate the individual.

DJ. The use according to example embodiment DI, wherein the starch comprising a resistant starch is selected from the group consisting of: an RS1, RS2, RS3, RS4 or RS5 starch, or combinations thereof.

DK. The use according to example embodiment DI, wherein the starch comprising a resistant starch is selected from the group consisting of:
a class V high amylose maize starch;
a class VI high amylose maize starch;
a class VII high amylose maize starch
a class VIII high amylose maize starch;
a class IX high amylose maize starch;
a class X high amylose maize starch;
a type IV resistant starch;
a type V resistant starch; and
combinations thereof.

DL. Use of a starch comprising a resistant starch selected from the group consisting of:
a class V high amylose maize starch;
a class VI high amylose maize starch;
a class VII high amylose maize starch
a class VIII high amylose maize starch;
a class IX high amylose maize starch;
a class X high amylose maize starch;
a type IV resistant starch;
a type V resistant starch; and
combinations thereof.

in a composition to maintain hydration in an individual and/or rehydrate the individual.

DM. The use according to example embodiment DK or example embodiment DL, wherein the type IV resistant starch is a resistant starch material that has been exposed to a chemical process selected from the group consisting of:
 a thermal or hydrothermal treatment;
 an enzymatic modification;
 an oxidation or bleaching process;
 a cross-bonding or crosslinking process;
 treatment with propylene oxide;
 treatment with glycerol;
 an etherification process;
 an esterification (or acylation) process;
 an acidification process;
 an alkalisation process;
 a dextrinisation process;
 a phosphorylation process; and
 combinations thereof,
to produce the type IV resistant starch.

DN. The use according to any one of example embodiments DK to DM, wherein the type IV resistant starch is selected from the group consisting of:
 a retrograded gelatinised class VII high amylose maize starch;
 a starch comprising a resistant starch that is acetylated;
 a starch comprising a resistant starch that is acylated;
 a bleached starch material;
 an oxidised starch material;
 an acid treated starch material;
 an alkaline treated starch material
 a phosphorylated starch material;
 acetylated tapioca starch;
 acetylated rice starch; and
 combinations thereof.

DO. The use according to example embodiment DK or example embodiment DL, wherein the starch comprising a resistant starch is a type V resistant starch.

DP. The use according to any one of example embodiments DI to DO, wherein the composition is: an oral rehydration composition according to any one of example embodiments A to W; an aqueous composition according to example embodiment X or example embodiment Y; a beverage according to any one of example embodiments BM to CE; or a food item according to any one of example embodiments CT to CY.

DQ. The use according to any one of example embodiments DI to DP, wherein the composition is consumed before the individual engages in a physical activity.

DR. The use according to example embodiment DQ, wherein the composition is consumed at least about 1, 2, 3, 4, 5, 6, 7, 8, 9, 10, 11, 12, 13, 14, 15 or 16 hours before the individual engages in the physical activity.

DS. The use according to example embodiment DQ or example embodiment DR, wherein the physical activity is a sport.

DT. The use according to any one of example embodiments DI to DS, wherein the individual is suffering from dehydration.

DU. The use according to any one of example embodiments DI to DT, wherein the individual is suffering from dehydration caused by diarrhoea.

DV. The oral rehydration composition according to any one of example embodiments AS or AU to AW, wherein the individual is a human being.

DW. The oral rehydration composition according to any one of example embodiments AS or AU to AW, wherein the individual is an animal.

DX. The aqueous composition according to any one of example embodiments Y to AB or AT to AW, wherein the individual is a human being.

DY. The aqueous composition according to any one of example embodiments Y to AB or AT to AW, wherein the individual is an animal.

DZ. The method according to any one of example embodiments AD to AR, wherein the individual is a human being.

EA. The method according to any one of example embodiments AD to AR, wherein the individual is an animal.

EB. The use according to any one of example embodiments AX to BL or DI to DU, wherein the individual is a human being.

EC. The use according to any one of example embodiments AX to BL or DI to DU, wherein the individual is an animal ED. The beverage according to any one of example embodiments BM to CS, wherein the individual is a human being.

EE. The beverage according to any one of example embodiments BM to CS, wherein the individual is an animal.

EF. The food item according to any one of example embodiments CT to DH, wherein the individual is a human being.

EG. The food item according to any one of example embodiments CT to DH, wherein the individual is an animal.

EH. The oral rehydration composition according to any one of example embodiments A to W, AS, AU to AW, DV or DW, wherein the starch comprising a resistant starch is selected from the group consisting of:
 an acid treated starch;
 an alkaline treated starch;
 a bleached starch;
 an oxidised starch;
 a mono-starch phosphate;
 a di-starch glycerol;
 a di-starch phosphate;
 a phosphatylated di-starch phosphate;
 an acetylated di-starch phosphate;
 an acetylated starch;
 an acetylaled di-starch adipate;
 an acetylated di-starch glycerol;
 a hydroxypropylstarch;
 a hydroxypropyl-di-starchglycerol;
 a hydroxypropyl-di-starchphosphate; and
 a starch comprising sodium octenyl succinate groups.

EI. The aqueous composition according to any one of example embodiments Y to AC, AT to AW, DX or DY, wherein the starch comprising a resistant starch is selected from the group consisting of:
 an acid treated starch;
 an alkaline treated starch;
 a bleached starch;
 an oxidised starch;
 a mono-starch phosphate;
 a di-starch glycerol;
 a di-starch phosphate;
 a phosphatylated di-starch phosphate;
 an acetylated di-starch phosphate;
 an acetylated starch;
 an acetylaled di-starch adipate;

an acetylated di-starch glycerol;
a hydroxypropylstarch;
a hydroxypropyl-di-starchglycerol;
a hydroxypropyl-di-starchphosphate; and
a starch comprising sodium octenyl succinate groups.

EJ. The method according to any one of example embodiments AC to AR, DZ or EA, wherein the starch comprising a resistant starch is selected from the group consisting of:
an acid treated starch;
an alkaline treated starch;
a bleached starch;
an oxidised starch;
a mono-starch phosphate;
a di-starch glycerol;
a di-starch phosphate;
a phosphatylated di-starch phosphate;
an acetylated di-starch phosphate;
an acetylated starch;
an acetylaled di-starch adipate;
an acetylated di-starch glycerol;
a hydroxypropylstarch;
a hydroxypropyl-di-starchglycerol;
a hydroxypropyl-di-starchphosphate; and
a starch comprising sodium octenyl succinate groups.

EK. The beverage according to any one of example embodiments BM to CS, ED or EE, wherein the starch comprising a resistant starch is selected from the group consisting of:
an acid treated starch;
an alkaline treated starch;
a bleached starch;
an oxidised starch;
a mono-starch phosphate;
a di-starch glycerol;
a di-starch phosphate;
a phosphatylated di-starch phosphate;
an acetylated di-starch phosphate;
an acetylated starch;
an acetylaled di-starch adipate;
an acetylated di-starch glycerol;
a hydroxypropylstarch;
a hydroxypropyl-di-starchglycerol;
a hydroxypropyl-di-starchphosphate; and
a starch comprising sodium octenyl succinate groups.

EL. The food item according to any one of example embodiments CT to DH, EF or EG, wherein the starch comprising a resistant starch is selected from the group consisting of:
an acid treated starch;
an alkaline treated starch;
a bleached starch;
an oxidised starch;
a mono-starch phosphate;
a di-starch glycerol;
a di-starch phosphate;
a phosphatylated di-starch phosphate;
an acetylated di-starch phosphate;
an acetylated starch;
an acetylaled di-starch adipate;
an acetylated di-starch glycerol;
a hydroxypropylstarch;
a hydroxypropyl-di-starchglycerol;
a hydroxypropyl-di-starchphosphate; and
a starch comprising sodium octenyl succinate groups.

EM. The use according to any one of example embodiments AX to BL, DI to DU, EB or EC, wherein the starch comprising a resistant starch is selected from the group consisting of:
an acid treated starch;
an alkaline treated starch;
a bleached starch;
an oxidised starch;
a mono-starch phosphate;
a di-starch glycerol;
a di-starch phosphate;
a phosphatylated di-starch phosphate;
an acetylated di-starch phosphate;
an acetylated starch;
an acetylaled di-starch adipate;
an acetylated di-starch glycerol;
a hydroxypropylstarch;
a hydroxypropyl-di-starchglycerol;
a hydroxypropyl-di-starchphosphate; and
a starch comprising sodium octenyl succinate groups.

EXAMPLES

Oral Rehydration Compositions and Solutions

Table 3 discloses the existing recommended WHO/UNICEF oral rehydration formulation and Table 4 and Table 5 disclose exemplified oral rehydration compositions of the invention.

Table 6, Table 7 and Table 8 examine various suspending agents and their ability to suspend acetylated high amylose starch, rice starch or high acetylated rice starch over a period of time. The total suspension height in each case was 3.5 cm. The height of material that has settled in each experiment, if any, is disclosed in the respective tables.

Table 9 discloses a beverage to be consumed by an individual taking part in a physical activity, the beverages comprising an exemplified oral rehydration composition of the invention.

TABLE 3

The formula for an ORS recommended by the WHO and UNICEF.[a), b)]

| Compound | Mass (g/L) | Relative molecular mass | % (w/w) | Concentration (mmol/L) | Concentration of specific elements/compounds (mmol/L) | | | | |
|---|---|---|---|---|---|---|---|---|---|
| | | | | | $Na^+$ | $K^+$ | $Cl^-$ | Citrate | Glucose |
| Sodium chloride | 2.6 | 58.4 | 12.7 | 45 | 45 | | 45 | | |
| Glucose (anhydrous) | 13.5 | 180.2 | 65.9 | 75 | | | | | 75 |
| Potassium chloride | 1.5 | 74.6 | 7.3 | 20 | | 20 | 20 | | |

TABLE 3-continued

The formula for an ORS recommended by the WHO and UNICEF.[a), b)]

| Compound | Mass (g/L) | Relative molecular mass | % (w/w) | Concentration (mmol/L) | Concentration of specific elements/compounds (mmol/L) | | | | |
|---|---|---|---|---|---|---|---|---|---|
| | | | | | Na$^+$ | K$^+$ | Cl$^-$ | Citrate | Glucose |
| Trisodium citrate (dihydrate) | 2.9 | 294.1 | 14.1 | 9.9 | 30 | | | 10 | |
| TOTAL | 20.5 | — | 100 | — | 75 | 20 | 65 | 10 | 75 |

[a)]Composition as of 4 Sep. 2012;
[b)]total osmolarity is 245 mOsmol/L.

TABLE 4

An exemplified oral rehydration composition of the present invention.[a)]

| Compound | Mass (g/L) | Relative molecular mass | Concentration (mmol/L) | Concentrations (mmol/L) | | | |
|---|---|---|---|---|---|---|---|
| | | | | Na$^+$ | K$^+$ | Cl$^-$ | Citrate |
| Sodium chloride | 2.6 | 58.44 | 45 | 45 | | 45 | |
| Potassium chloride | 1.5 | 74.55 | 20 | | 20 | 20 | |
| Trisodium citrate (dihydrate) | 2.9 | 294.1 | 10 | 30 | | | 10 |
| Starch (comprising a resistant starch)[a)] | 50[c)] | >1,000 | [d)] | | | | |
| Xanthan gum[e)] | 2 | >1,000 | [d)] | | | — | — |
| TOTAL | 59 | | | 75 | 20 | 65 | 10 |

[a)]The total osmolarity is 172.5 mOsm/L;
[b)]the actual resistant starches incorporated in the present example are chosen from: a class VII high amylose maize starch (for example Hylon ® VII obtainable from Ingredion), a starch comprising a resistant starch, that has been acetylated up to a substitution value of 2.5% (for example, Crisp Film ® obtainable from Ingredion), a starch comprising a resistant starch, that has been acetylated with a substitution value greater than 2.5% (for example Starplus ™ A (obtainable from CSIRO) with a substitution value of 4.0, 6.0 or 7.5%), or an acetylated tapioca starch or an acetylated rice starch;
[c)]50 g/L of resistant starch will yield approximately the same amount of glucose that is available in the composition of Table 3;
[d)]it is not possible to give the concentration of the fermentable substrate or xanthan gum in mmol/L since the molecular weights are >1,000 and not all molecules are the same size;
[e)]the specific xanthan gum to use in this example is Grindsted Xanthan Clear Easy A21191; it contains 2 g sodium/100 g.

The components of Table 4 can be placed in individual sachets grouped, for example, as: sodium chloride, potassium chloride and trisodium citrate (dihydrate) in sachet 1; and the starch comprising a resistant starch and xanthan gum in sachet 2. To prepare an oral rehydration solution, the contents of sachet 1 should first be mixed in drinking water. When the contents of sachet 1 are dissolved, the contents of sachet 2 should be added and vigorously mixed until an even milky suspension is achieved.

TABLE 5

An exemplified oral rehydration composition of the present invention.

| Compound | Mass (g/L) | Relative molecular mass | Concentration (mmol/L) | Concentrations (mmol/L) | | | | |
|---|---|---|---|---|---|---|---|---|
| | | | | Na$^+$ | K$^+$ | Cl$^-$ | Citrate | Glucose |
| Sodium chloride | 2.6 | 58.44 | 45 | 45 | | 45 | | |
| Potassium chloride | 1.5 | 74.55 | 20 | | 20 | 20 | | |
| Trisodium citrate (dihydrate) | 2.9 | 294.1 | 10 | 30 | | | 10 | |
| Glucose (anhydrous) | 6.75[e)] | 180.2 | 37 | | | | | 37 |

TABLE 5-continued

An exemplified oral rehydration composition of the present invention.

| Compound | Mass (g/L) | Relative molecular mass | Concentration (mmol/L) | Concentrations (mmol/L) | | | | |
|---|---|---|---|---|---|---|---|---|
| | | | | Na$^+$ | K$^+$ | Cl$^-$ | Citrate | Glucose |
| Starch (comprising a resistant starch)$^{a)}$ | 25$^{b)}$ | >1,000 | $^{c)}$ | | | | | |
| Xanthan gum$^{d)}$ | 2 | >1,000 | $^{c)}$ | — | — | | | |
| TOTAL | 40.75 | | | 75 | 20 | 65 | 10 | 37 |

$^{a)}$The actual resistant starches incorporated in the present example are chosen from: a class VII high amylose maize starch (for example Hylon ® VII obtainable from Ingredion), a starch comprising a resistant starch, that has been acetylated up to a substitution value of 2.5% (for example, Crisp Film ® obtainable from Ingredion), a starch comprising a resistant starch, that has been acetylated with a substitution value greater than 2.5% (for example Starplus ™ A (obtainable from CSIRO) with a substitution value of 4.0, 6.0 or 7.5%), or an acetylated tapioca starch or an acetylated rice starch;
$^{b)}$the actual amount of starch added may be in the range 0 to 50 g/L but the starch together with the glucose would be combined in such quantities so as to yield approximately the same amount of glucose as contained in the composition of Table 3;
$^{c)}$it is not possible to give the concentration of the fermentable substrate or xanthan gum in mmol/L since the molecular weights are >1,000 and not all molecules are the same size;
$^{d)}$the specific xanthan gum to use in this example is Grindsted Xanthan Clear Easy A21191; it contains 2 g sodium/100 g;
$^{e)}$the actual amount of glucose may be added in the range 0-13.5 g/L.

TABLE 6

Exemplified compositions with high amylose maize starch (50 g/L) assessed with 0.75 g in 15 mL.

| Suspending Agent | Ease of Solubility$^{a)}$ | State of Composition at Specific Time Intervals After Composition is Produced | | | |
|---|---|---|---|---|---|
| | | 2 hours | 4 hours | 6 hours | 24 hours |
| 1 g/L Xanthan | 3+ | 90% Suspended | 75% Suspended | 90% Settled | Settled (0.5 cm) |
| 2 g/L Xanthan | 2+ | Suspended | Suspended | Suspended | 90% Suspended |
| 3 g/L Xanthan | 1+ | Suspended | Suspended | Suspended | Suspended |
| 2 g/L Guar gum | 3+ | 90% Settled | Settled (0.5 cm) | Settled (0.5 cm) | Settled (0.5 cm) |
| 4 g/L Guar gum$^{b)}$ | 3+ | Suspended | Suspended | 75% Settled | Settled (0.7 cm) |
| 6 g/L Guar gum$^{c)}$ | 2+ | Suspended | Suspended | Suspended | Suspended |
| 11 g/L Gelatine | 3+$^{d)}$ | Settled (0.5 cm) | Settled (0.5 cm) | Settled (0.5 cm) | Settled (0.5 cm) |
| 15 g/L Gelatine | 3+$^{d)}$ | Settled (0.5 cm) | Settled (0.5 cm) | Settled (0.5 cm) | Settled (0.5 cm) |
| 120 g/L Gelatine | 2+$^{d)}$ | Settled (0.5 cm) | Settled (0.5 cm) | Settled (0.5 cm) | Settled (0.5 cm) |
| 9 g/L Carrageenan | 3+$^{d)}$ | Settled (1.6 cm) | Settled (1.6 cm) | Settled (1.6 cm) | Settled (1.6 cm) |
| 12 g/L Carrageenan | 2+$^{d)}$ | Settled (1.9 cm) | Settled (1.9 cm) | Settled (1.9 cm) | Settled (1.9 cm) |
| 15 g/L Carrageenan | 1+$^{d)}$ | Settled (2.1 cm) | Settled (2.1 cm) | Settled (2.1 cm) | Settled (2.1 cm) |
| 8 g/L Agar | 3+$^{d)}$ | Settled (0.5 cm) | Settled (0.5 cm) | Settled (0.5 cm) | Settled (0.5 cm) |
| 12 g/L Agar | 1+$^{d)}$ | Settled (0.7 cm) | Settled (0.7 cm) | Settled (0.7 cm) | Settled (0.7 cm) |
| 15 g/L Agar | 1+$^{d)}$ | Settled (0.8 cm) | Settled (0.8 cm) | Settled (0.8 cm) | Settled (0.8 cm) |
| 4 g/L Alginate | 3+ | Settled (0.4 cm) | Settled (0.4 cm) | Settled (0.4 cm) | Settled (0.4 cm) |
| 8 g/L Alginate | 3+ | 75% Settled | 90% Settled | Settled (0.5 cm) | Settled (0.5 cm) |
| 12 g/L Alginate | 3+$^{d)}$ | Suspended | 90% Suspended | 90% Settled | Settled (0.6 cm) |
| 4 g/L Locust bean gum | 2+$^{d)}$ | Settled (0.5 cm) | Settled (0.5 cm) | Settled (0.5 cm) | Settled (0.5 cm) |
| 8 g/L Locust bean gum | 1+$^{d)}$ | 75% Settled | 90% Settled | Settled (0.5 cm) | Settled (0.5) |
| 12 g/L Locust bean gum | 1+$^{d)}$ | Suspended | Suspended | 75% Settled | 90% Settled (0.8 cm) |
| 13 g/L Gum Arabic | 2+$^{d)}$ | Settled (0.3 cm) | Settled (0.3 cm) | Settled (0.3 cm) | Settled (0.3 cm) |
| 20 g/L Gum Arabic | 2+$^{d)}$ | Settled (0.4 cm) | Settled (0.4 cm) | Settled (0.4 cm) | Settled (0.4 cm) |
| 25 g/L Gum Arabic | 2+$^{d)}$ | Settled (0.4 cm) | Settled (0.4 cm) | Settled (0.4 cm) | Settled (0.4 cm) |
| 10 g/L Cellulose | 2+$^{d)}$ | Settled (0.6 cm) | Settled (0.6 cm) | Settled (0.6 cm) | Settled (0.6 cm) |
| 14 g/L Cellulose | 1+$^{d)}$ | Settled (0.8 cm) | Settled (0.8 cm) | Settled (0.8 cm) | Settled (0.8 cm) |
| 20 g/L Cellulose | 1+$^{d)}$ | Settled (0.9 cm) | Settled (0.9 cm) | Settled (0.9 cm) | Settled (0.9 cm) |
| 8 g/L Gellan | 2+$^{d)}$ | Settled (1.3 cm) | Settled (1.3 cm) | Settled (1.3 cm) | Settled (1.3 cm) |
| 12 g/L Gellan | 1+$^{d)}$ | Settled (1.8 cm) | Settled (1.8 cm) | Settled (1.8 cm) | Settled (1.8 cm) |
| 15 g/L Gellan | 1+$^{d)}$ | Settled (2.0 cm) | Settled (2.0 cm) | Settled (2.0 cm) | Settled (2.0 cm) |
| 7 g/L Pectin | 2+$^{d)}$ | Settled (0.4 cm)$^{e}$ | Settled (0.4 cm)$^{e}$ | Settled (0.4 cm)$^{e}$ | Settled (0.4 cm)$^{e}$ |
| 15 g/L Pectin | 1+$^{d)}$ | Settled (0.5 cm)$^{e)}$ | Settled (0.5 cm)$^{e)}$ | Settled (0.5 cm)$^{e)}$ | Settled (0.5 cm)$^{e)}$ |
| 25 g/L Pectin | 1+$^{d)}$ | Suspended | 75% Suspended | 75% Settled | Settled (0.7 cm)$^{e)}$ |

$^{a)}$3+ = easily suspended after a few swirls; 2+ = suspended after at least 5-6 swirls; 1+ = suspended after >6 swirls;
$^{b)}$viscous composition;
$^{c)}$very viscous composition;
$^{d)}$composition heated to 60° C. for 15 minutes;
$^{e)}$brown cloudy appearance.

TABLE 7

Exemplified compositions with rice starch (50 g/L) assessed with 0.75 g in 15 mL.

| Suspending Agent | Ease of Solubility[a] | State of Composition at Specific Time Intervals After Composition is Produced | | | |
|---|---|---|---|---|---|
| | | 2 hours | 4 hours | 6 hours | 24 hours |
| 1 g/L Xanthan | 3+ | Suspended | Suspended | 50% Settled | Settled (0.6 cm) |
| 2 g/L Xanthan | 2+ | Suspended | Suspended | Suspended | Suspended |
| 3 g/L Xanthan | 1+ | Suspended | Suspended | Suspended | Suspended |
| 2 g/L Guar gum | 3+ | 75% Suspended | 75% Settled | 90% Settled | Settled (0.5 cm) |
| 4 g/L Guar gum[b] | 3+ | Suspended | Suspended | Suspended | 90% Settled |
| 6 g/L Guar gum[c] | 2+ | Suspended | Suspended | Suspended | 50% Settled |
| 11 g/L Gelatine | 3+[d] | Settled (0.4 cm) | Settled (0.4 cm) | Settled (0.4 cm) | Settled (0.4 cm) |
| 15 g/L Gelatine | 3+[d] | Settled (0.4 cm) | Settled (0.4 cm) | Settled (0.4 cm) | Settled (0.4 cm) |
| 120 g/L Gelatine | 2+[d] | Settled (0.5 cm) | Settled (0.5 cm) | Settled (0.5 cm) | Settled (0.5 cm) |
| 9 g/L Carrageenan | 3+[d] | Settled (1.5 cm) | Settled (1.5 cm) | Settled (1.5 cm) | Settled (1.5 cm) |
| 12 g/L Carrageenan | 2+[d] | Settled (1.8 cm) | Settled (1.8 cm) | Settled (1.8 cm) | Settled (1.8 cm) |
| 15 g/L Carrageenan | 1+[d] | Settled (1.9 cm) | Settled (1.9 cm) | Settled (1.9 cm) | Settled (1.9 cm) |
| 8 g/L Agar | 3+[d] | Settled (0.5 cm) | Settled (0.5 cm) | Settled (0.5 cm) | Settled (0.5 cm) |
| 12 g/L Agar | 1+[d] | Settled (0.8 cm) | Settled (0.8 cm) | Settled (0.8 cm) | Settled (0.8 cm) |
| 15 g/L Agar | 1+[d] | Settled (0.8 cm) | Settled (0.8 cm) | Settled (0.8 cm) | Settled (0.8 cm) |
| 4 g/L Alginate | 3+ | Settled (0.4 cm) | Settled (0.4 cm) | Settled (0.4 cm) | Settled (0.4 cm) |
| 8 g/L Alginate | 3+ | 75% Suspended | 75% Settled | 90% Settled | Settled (0.6 cm) |
| 12 g/L Alginate | 3+[d] | Suspended | Suspended | 75% Settled | 90% Settled (0.7 cm) |
| 4 g/L Locust bean gum | 2+[d] | Settled (0.6 cm) | Settled (0.6 cm) | Settled (0.6 cm) | Settled (0.6 cm) |
| 8 g/L Locust bean gum | 1+[d] | Suspended | 50% Settled | 90% Settled | Settled (0.6 cm) |
| 1 g/L Xanthan | 3+ | Suspended | Suspended | 50% Settled | Settled (0.6 cm) |
| 2 g/L Xanthan | 2+ | Suspended | Suspended | Suspended | Suspended |
| 3 g/L Xanthan | 1+ | Suspended | Suspended | Suspended | Suspended |
| 12 g/L Locust bean gum | 1+[d] | Suspended | Suspended | Suspended | 90% Settled (0.7 cm) |
| 13 g/L Gum Arabic | 2+[d] | Settled (0.3 cm) | Settled (0.3 cm) | Settled (0.3 cm) | Settled (0.3 cm) |
| 20 g/L Gum Arabic | 2+[d] | Settled (0.4 cm) | Settled (0.4 cm) | Settled (0.4 cm) | Settled (0.4 cm) |
| 25 g/L Gum Arabic | 2+[d] | Settled (0.4 cm) | Settled (0.4 cm) | Settled (0.4 cm) | Settled (0.4 cm) |
| 10 g/L Cellulose | 2+[d] | Settled (0.4 cm) | Settled (0.4 cm) | Settled (0.4 cm) | Settled (0.4 cm) |
| 14 g/L Cellulose | 1+[d] | Settled (0.6 cm) | Settled (0.6 cm) | Settled (0.6 cm) | Settled (0.6 cm) |
| 20 g/L Cellulose | 1+[d] | Settled (0.6 cm) | Settled (0.6 cm) | Settled (0.6 cm) | Settled (0.6 cm) |
| 8 g/L Gellan | 2+[d] | Settled (1.3 cm) | Settled (1.3 cm) | Settled (1.3 cm) | Settled (1.3 cm) |
| 12 g/L Gellan | 1+[d] | Settled (1.7 cm) | Settled (1.7 cm) | Settled (1.7 cm) | Settled (1.7 cm) |
| 15 g/L Gellan | 1+[d] | Settled (1.7 cm) | Settled (1.7 cm) | Settled (1.7 cm) | Settled (1.7 cm) |
| 7 g/L Pectin | 2+[d] | Settled (0.3 cm)[e] | Settled (0.3 cm)[e] | Settled (0.3 cm)[e] | Settled (0.3 cm)[e] |
| 15 g/L Pectin | 1+[d] | Settled (0.5 cm)[e] | Settled (0.5 cm)[e] | Settled (0.5 cm)[e] | Settled (0.5 cm)[e] |
| 25 g/L Pectin[f] | 1+[d] | Suspended | Settled (0.3 cm)[e] | Settled (0.4 cm)[e] | Settled (0.5 cm)[e] |

[a] 3+ = easily suspended after a few swirls; 2+ = suspended after at least 5-6 swirls; 1+ = suspended after >6 swirls;
[b] viscous composition;
[c] very viscous composition;
[d] composition heated to 60° C. for 15 minutes;
[e] brown cloudy appearance;
[f] difficult to suspend, brown cloudy appearance.

TABLE 8

Exemplified compositions with high acetylated rice starch (50 g/L) assessed with 0.75 g in 15 mL.

| Suspending Agent | Ease of Solubility[a] | State of Composition at Specific Time Intervals After Composition is Produced | | | |
|---|---|---|---|---|---|
| | | 2 hr | 4 hrs | 6 hrs | 24 hrs |
| 1 g/L Xanthan | 3+ | Suspended | Suspended | Suspended | 90% Settled |
| 2 g/L Xanthan | 2+ | Suspended | Suspended | Suspended | Suspended |
| 3 g/L Xanthan | 1+ | Suspended | Suspended | Suspended | Suspended |
| 2 g/L Guar gum | 3+ | 75% Suspended | 75% Settled | 90% Settled | Settled (0.5 cm) |
| 4 g/L Guar gum[b] | 3+ | Suspended | Suspended | Suspended | 50% Settled |
| 6 g/L Guar gum[c] | 2+ | Suspended | Suspended | Suspended | Suspended |
| 11 g/L Gelatine | 3+[d] | Settled (0.5 cm)[e] | Settled (0.5 cm)[e] | Settled (0.5 cm)[e] | Settled (0.5 cm)[e] |
| 15 g/L Gelatine | 3+[d] | Settled (0.5 cm)[e] | Settled (0.5 cm)[e] | Settled (0.5 cm)[e] | Settled (0.5 cm)[e] |
| 20 g/L Gelatine | 2+[d] | 90% Settled | 90% Settled | 90% Settled | 90% Settled |
| 9 g/L Carrageenan | 3+[d] | Settled (1.5 cm) | Settled (1.5 cm) | Settled (1.5 cm) | Settled (1.5 cm) |
| 12 g/L Carrageenan | 2+[d] | Settled (1.8 cm) | Settled (1.8 cm) | Settled (1.8 cm) | Settled (1.8 cm) |
| 15 g/L Carrageenan | 1+[d] | Settled (2.1 cm) | Settled (2.1 cm) | Settled (2.1 cm) | Settled (2.1 cm) |
| 8 g/L Agar | 3+[d] | Settled (0.6 cm) | Settled (0.6 cm) | Settled (0.6 cm) | Settled (0.6 cm) |
| 12 g/L Agar | 1+[d] | Settled (0.7 cm) | Settled (0.7 cm) | Settled (0.7 cm) | Settled (0.7 cm) |
| 15 g/L Agar | 1+[d] | Settled (0.8 cm) | Settled (0.8 cm) | Settled (0.8 cm) | Settled (0.8 cm) |
| 4 g/L Alginate | 3+ | Settled (0.6 cm) | Settled (0.6 cm) | Settled (0.6 cm) | Settled (0.6 cm) |
| 8 g/L Alginate | 3+ | 90% Suspended | 50% Suspended | 90% Settled | Settled (0.5 cm) |
| 12 g/L Alginate | 3+[d] | Suspended | Suspended | Suspended | 90% Settled |
| 4 g/L Locust bean gum | 2+[d] | 90% Settled | Settled (0.6 cm) | Settled (0.6 cm) | Settled (0.6 cm) |

TABLE 8-continued

Exemplified compositions with high acetylated rice starch (50 g/L) assessed with 0.75 g in 15 mL.

| Suspending Agent | Ease of Solubility[a] | State of Composition at Specific Time Intervals After Composition is Produced | | | |
|---|---|---|---|---|---|
| | | 2 hr | 4 hrs | 6 hrs | 24 hrs |
| 8 g/L Locust bean gum | 1+[d] | Suspended | Suspended | Suspended | Suspended |
| 12 g/L Locust bean gum | 1+[d] | Suspended | Suspended | Suspended | Suspended |
| 13 g/L Gum Arabic | 2+[d] | Settled (0.4 cm) | Settled (0.4 cm) | Settled (0.4 cm) | Settled (0.4 cm) |
| 20 g/L Gum Arabic | 2+[d] | Settled (0.4 cm) | Settled (0.4 cm) | Settled (0.4 cm) | Settled (0.4 cm) |
| 25 g/L Gum Arabic | 2+[d] | Settled (0.5 cm) | Settled (0.5 cm) | Settled (0.5 cm) | Settled (0.5 cm) |
| 10 g/L Cellulose | 2+[d] | Settled (0.7 cm) | Settled (0.7 cm) | Settled (0.7 cm) | Settled (0.7 cm) |
| 14 g/L Cellulose | 2+[d] | Settled (0.7 cm) | Settled (0.7 cm) | Settled (0.7 cm) | Settled (0.7 cm) |
| 20 g/L Cellulose | 1+[d] | Settled (0.8 cm) | Settled (0.8 cm) | Settled (0.8 cm) | Settled (0.8 cm) |
| 8 g/L Gellan | 2+[d] | Settled (1.3 cm) | Settled (1.3 cm) | Settled (1.3 cm) | Settled (1.3 cm) |
| 12 g/L Gellan | 1+[d] | Settled (1.8 cm) | Settled (1.8 cm) | Settled (1.8 cm) | Settled (1.8 cm) |
| 15 g/L Gellan | 1+[d] | Settled (2.0 cm) | Settled (2.0 cm) | Settled (2.0 cm) | Settled (2.0 cm) |
| 7 g/L Pectin | 2+[d] | Settled (0.4 cm)[e] | Settled (0.4 cm)[e] | Settled (0.4 cm)[e] | Settled (0.4 cm)[e] |
| 15 g/L Pectin | 1+[d] | Settled (0.5 cm)[e] | Settled (0.5 cm)[e] | Settled (0.5 cm)[e] | Settled (0.5 cm)[e] |
| 25 g/L Pectin[f] | 1+[d] | Suspended | Settled (0.6 cm)[e] | Settled (0.6 cm)[e] | Settled (0.6 cm)[e] |

[a]3+ = easily suspended after a few swirls; 2+ = suspended after at least 5-6 swirls; 1+ = suspended after >6 swirls;
[b]viscous composition;
[c]very viscous composition;
[d]composition heated to 60° C. for 15 minutes;
[e]cloudy appearance;
[f]difficult to suspend even when heated.

TABLE 9

An exemplary beverage that comprises an oral rehydration composition of the invention.

| Component | Amount |
|---|---|
| Sodium Chloride[a] | 1.45 g/L |
| Potassium Chloride | 0.4 g/L |
| Trisodium citrate (dihydrate) | 1.6 g/L |
| Glucose | 5.0 g/L |
| Xanthan | 2.0 g/L |
| Starch (high amylose maize starch or high amylose maize starch acetylated to 2.5%) | 45 g/L |

The components of Table 9 were introduced into drinking water that further comprised Cottee's® low sugar apple-raspberry cordial to flavour the beverage. The cordial consisting of reconstituted fruit juices (apple 48%, raspberry 2%), water, thickener (sodium carboxymethylcellulose), food acid (citric acid), natural flavour, sweeteners (calcium cyclamate, acesulfame potassium, sucralose), natural colour (anthocyanins) and preservatives (sodium benzoate, sodium metabisulphite).

Closed Loop Intestinal Perfusion Studies of Oral Rehydration Composition Additives Studies were undertaken to determine whether the addition of suspending agents as additives to high amylose maize 6% acetate (hereinafter HAMSA6) oral rehydration solution would affect the absorption of fluid from the control oral rehydration solution (Glucose-ORS)

Methods Used

Adult Sprague Dawley rats weighing 250-300 g were used for these studies. The rats were anaesthetised with an intraperitoneal injection of ketamine and pentobarbitone. Anaesthesia was maintained during the perfusion by supplemental doses of pentobarbitone as necessary. The rats' abdomens were opened through midline incision, and two loops of 10 cm length constructed in the ileum and in the colon. The loops were filled with 2 mL of a test solution containing fluoresceinated dextran sulphate along with cholera toxin 100 mcg and tied at both ends. The loops were emptied of content after 60 minutes and the fluid examined for fluorescence.

The test solutions all had the following salt composition, identical to that of the recommended WHO oral rehydration solutions:
 sodium chloride 45 mmol/L;
 potassium chloride 20 mmol/L; and
 trisodium citrate 10 mmol/L.
The individual test solutions are shown in Table 10.

TABLE 10

Composition utilised in the closed loop intestinal perfusion studies.

| Specific Oral Rehydration Solution | NaCl mmol/L | KCl mmol/L | Trisodium citrate mmol/L | Glucose Source | Suspending Agent | Osmolarity mmol/kg |
|---|---|---|---|---|---|---|
| Glucose-ORS | 45 | 20 | 10 | Glucose (75 mmol/L) | — | 245 |
| HAMSA6 | 45 | 20 | 10 | HAMSA6 (50 g/L) | — | 170 |
| HAMSA6 + Xanthan | 45 | 20 | 10 | HAMSA6 (50 g/L) | Xanthan (2.0 g/L) | 170 |
| HAMSA6 + Guar Gum | 45 | 20 | 10 | HAMSA6 (50 g/L) | Guar gum (2.0 g/L) | 170 |
| HAMSA6 + CMC | 45 | 20 | 10 | HAMSA6 (50 g/L) | CMC (2.0 g/L) | 170 |

TABLE 10-continued

Composition utilised in the closed loop intestinal perfusion studies.

| Specific Oral Rehydration Solution | NaCl mmol/L | KCl mmol/L | Trisodium citrate mmol/L | Glucose Source | Suspending Agent | Osmolarity mmol/kg |
|---|---|---|---|---|---|---|
| HAMSA6 + Carrageenan | 45 | 20 | 10 | HAMSA6 (50 g/L) | Carrageenan (2.0 g/L) | 170 |
| HAMSA6 + Alginate | 45 | 20 | 10 | HAMSA6 (50 g/L) | Alginate (2.0 g/L) | 170 |
| HAMSA6 + Gelatin | 45 | 20 | 10 | HAMSA6 (50 g/L) | Gelatin (2.0 g/L) | 170 |

Materials and Equipment

Fluorescent (FITC-conjugated) dextran (MW 3000-5000, FD4-1G, Sigma Chemical Co, MO, USA) was used as a non-absorbable marker at a concentration of 2.5 mg/mL. All solutions, except Ringer solution, were composed of hypo-osmolar oral rehydration solution (HO-ORS) as the base with or without added fermentable substrate. Dextran fluorescence was read in a Victor 3 (Perkin-Elmer) multilabel plate reader and expressed as fluorescence units.

Net water transport (μL/min/cm) was calculated using the following equation:

$$\text{Net transport} = Vi - [Vi \times DEXi/DEXo]/\text{length of gut in cm} \times 1000$$

where:
Vi=Volume of fluid infused in milliliters
DEXi=Dextran concentration in infusate (mg/mL)
DEXo=Dextran concentration in effluent (mg/mL)

Results

Net water secretion was noted both in ileum and colon in Glucose-ORS perfused loops. Addition of high amylose maize acetate was associated with reversal of net secretion to net water absorption. The effect of HAMSA6 was not significantly altered by the addition of the "suspending agents" tested (Table 11).

TABLE 11

Net water secretion for specific oral rehydration solutions of Table 10.

| Specific Oral Rehydration Solution | N | Net ileal water transport (μL/min/cm) | Net colonic water transport (μL/min/cm |
|---|---|---|---|
| Glucose | 3 | −2.60 (3.39) | −7.23 (3.44) |
| HAMSA6 | 4 | 1.09 (0.92) | 1.55 (1.46) |
| HAMSA6 + Xanthan | 5 | 1.41 (0.35) | 2.32 (0.81) |
| HAMSA6 + Guar Gum | 4 | 1.61 (0.12) | 1.31 (0.73) |
| HAMSA6 + Carboxymethylcellulose | 5 | 1.22 (0.17) | 2.04 (0.54) |
| HAMSA6 + Carrageenan | 3 | 0.35 (0.54) | 1.97 (1.25) |
| HAMSA6 + Alginate | 3 | 1.47 (0.35) | 3.51 (0.18) |
| HAMSA6 + Gelatin | 3 | 1.22 (0.69) | 1.18 (0.61) |

Conclusion

Additives used to suspend HAMSA6 did not significantly alter absorption from ileal and colonic loops in the rat.

Utilising Oral Rehydration Compositions of the Invention with Australian Football Players Method and Materials Australian football players were provided with the following beverages:

1. an oral rehydration composition (SpORS) that was to be consumed during and after a training session. SpORS consisted of the following components: 1.45 g NaCl, 0.4 g KCl, 1.6 g trisodium citrate (dihydrate), 5 g glucose, 45 g high acetylated maize starch (HAMS) acetylated to a substitution value of 2.5% (Crispfilm), Xanthan and Cottees double concentrate cordial (apple and raspberry flavouring); and 2. a beverage comprising a resistant starch (RS-Shake) that was to be consumed the night before a training session. RS-Shake consisted of the following components: high acetylated maize starch (HAMS-A) (50 g or 100 g of HAMS-A) acetylated to a substitution value of 2.5% (Crisp Film) and flavoured milk.

Each participant was studied in a control week (where the participant undertook their normal routine before, during and after a training session) and an intervention week (where the participant consumed the SpORS and RS-Shake at the required times). In the intervention week, a participant consumed a RS-Shake in the evening prior to a training session and consumed SpORS in training drink breaks from halfway through the training session until 1 hour after training has finished. Participants were assessed during both weeks.

The following measurements were taken as hydration indicators before, after and around 1 hour after each training session:
  weight; and
  a finger-prick of blood for a haematocrit test.

Predictive statistical models were used to assess any differences between intervention and control groups at each of the following time points: A—before a training session; B—at the end of a training session; and C—1 hour after training has finished.

The models adjusted for variation between players to incorporate effects of an intervention (consumption of SpORS/RS-Shake), overall workload and intensity (GPS data), recovery time and random variations between training days. Players were excluded if they had a light training session (light training session was taken as a session of less than 80 minutes). This was to ensure that players with a low workload did not bias the analysis.

Figure 2:
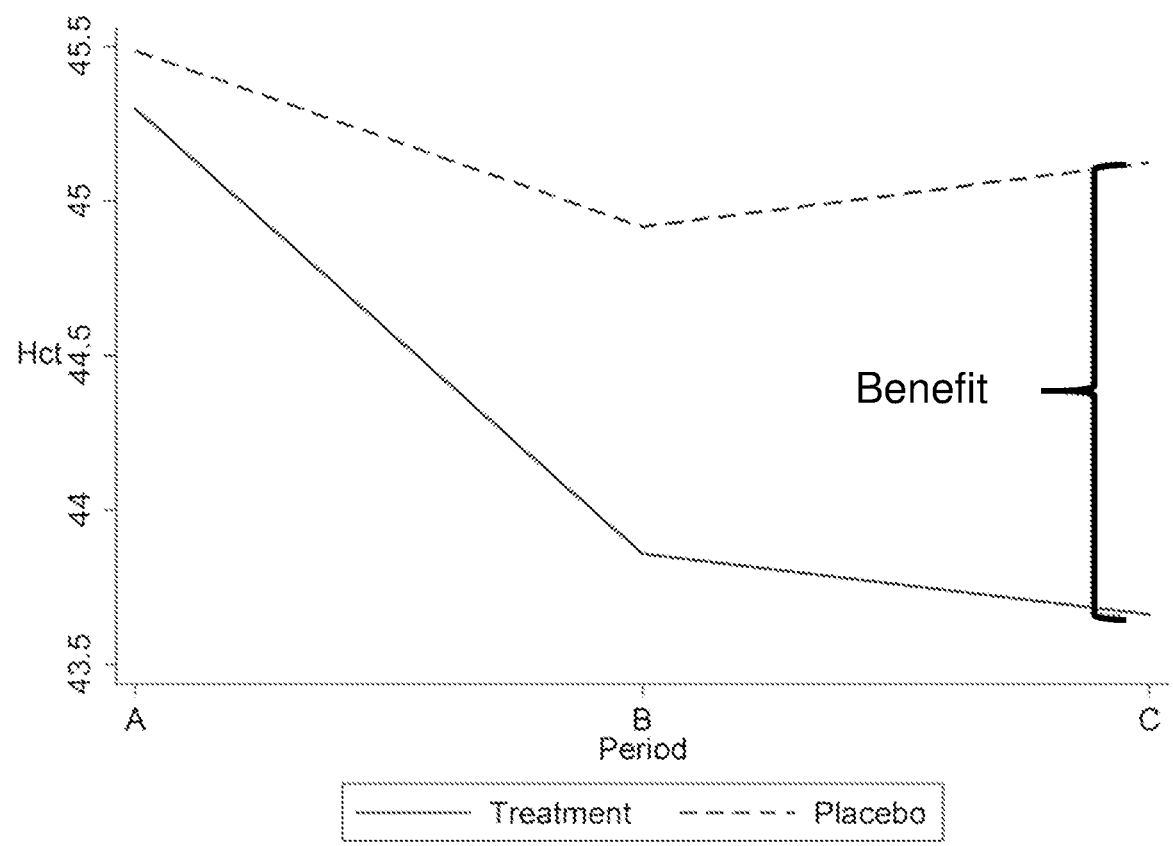
FIG. 2 shows is the mean packed cell volume percentage (%) of red blood cells (haematocrit test) in the blood of Australian football players during a control week and a week consuming compositions of the invention, at three time periods (A—before a training session; B—at the end of a training session; and C—1 hour after training has finished)

Results:

The results of the weight and blood analyses are shown in FIG. 1 and FIG. 2, respectively. In addition, the specific results are shown in Table 12 and Table 13, respectively.

TABLE 12

Detailed weight analysis for Australian football players study

| Time Period | A | B | C |
|---|---|---|---|
| Treatment Effect | 0.280 kg (P = 0.042) | 0.427 kg (P = 0.009) | 0.591 kg (P = 0.001) |

With regards to Table 12, a 280 g mean higher weight at time point A implies that the RS-Shake worked and players were better hydrated at the start of the day (and control groups were potentially under-hydrated before training). A 427 g mean higher weight at time point B implies that intervention players were better hydrated players throughout training. In addition, a 591 g mean higher weight time point C implies that intervention players rehydrated players faster during their recovery period.

TABLE 13

Detailed hematocrit analysis for Australian football players study

| Time Period | A | B | C |
|---|---|---|---|
| Treatment Effect | −0.374 (P = 0.377) | 0-1.041 (P = 0.137) | −0.993 (P = 0.059) |

With regards to Table 13, the trend is consistent with the weight data shown in Table 12 and the improved hydration as measured by haematocrit demonstrated that the increase in weight did not just represent fluid retention in the intestines but true rehydration of the players.

Conclusions

Based on the results, ingestion of the SpORS and RS-Shake helps to provide better hydration before training, less dehydration during training, and aids a player to rehydrate faster once training has finished. This, in turn, should improve a player's performance.

Utilising Oral Rehydration Compositions in Clinical Trails

A study was undertaken to examine the effects of oral rehydration solutions comprising either a:
high amylose maize starch (HAMS);
HAMS acetylated with a substitution value of 2.5%;
HAMS acetylated with a substitution value of 6%.

The actual formulations used for the present study can be found in Table 14.

TABLE 14

Formulations used in clinical trials of oral rehydration compositions of the invention.

| Compound | Mass (g/L) | Relative molecular mass | Concentration (mmol/L) | Concentrations (mmol/L) | | | |
|---|---|---|---|---|---|---|---|
| | | | | $Na^+$ | $K^+$ | $Cl^-$ | Citrate |
| Sodium chloride | 2.6 | 58.44 | 44.5 | 44.5 | | 44.5 | |
| Potassium chloride | 1.5 | 74.55 | 20.1 | | 20.1 | 20.1 | |
| Trisodium citrate (dihydrate) | 2.9 | 294.1 | 9.9 | 29.6 | | | 9.9 |
| Starch (comprising a resistant starch[a]) | 50 | [b] | 0.02-0.05[c] | | | | |
| Xanthan gum | 2 | >1000 | 1.4[c] | 1.4[c] | | | |
| TOTAL | 59 | | | 75.5 | 20.1 | 64.6 | 9.9 |

[a]The starch was either HAMS; HAMS acetylated to a substitution value of 2.5% or HAMS acetylated to a substitution value of 6%;
[b]the relative molecular weight is dependent on the specific resistant starch utilised in the study; and
[c]approximate values are provided as the molecular weights of the starch and xanthan gum are not exact;

These formulations were compared to the current WHO standard oral rehydration formulation (HO-ORS).

The HAMS formulations all contained the xanthan gum as an anti-settling agent.

Figure 3:
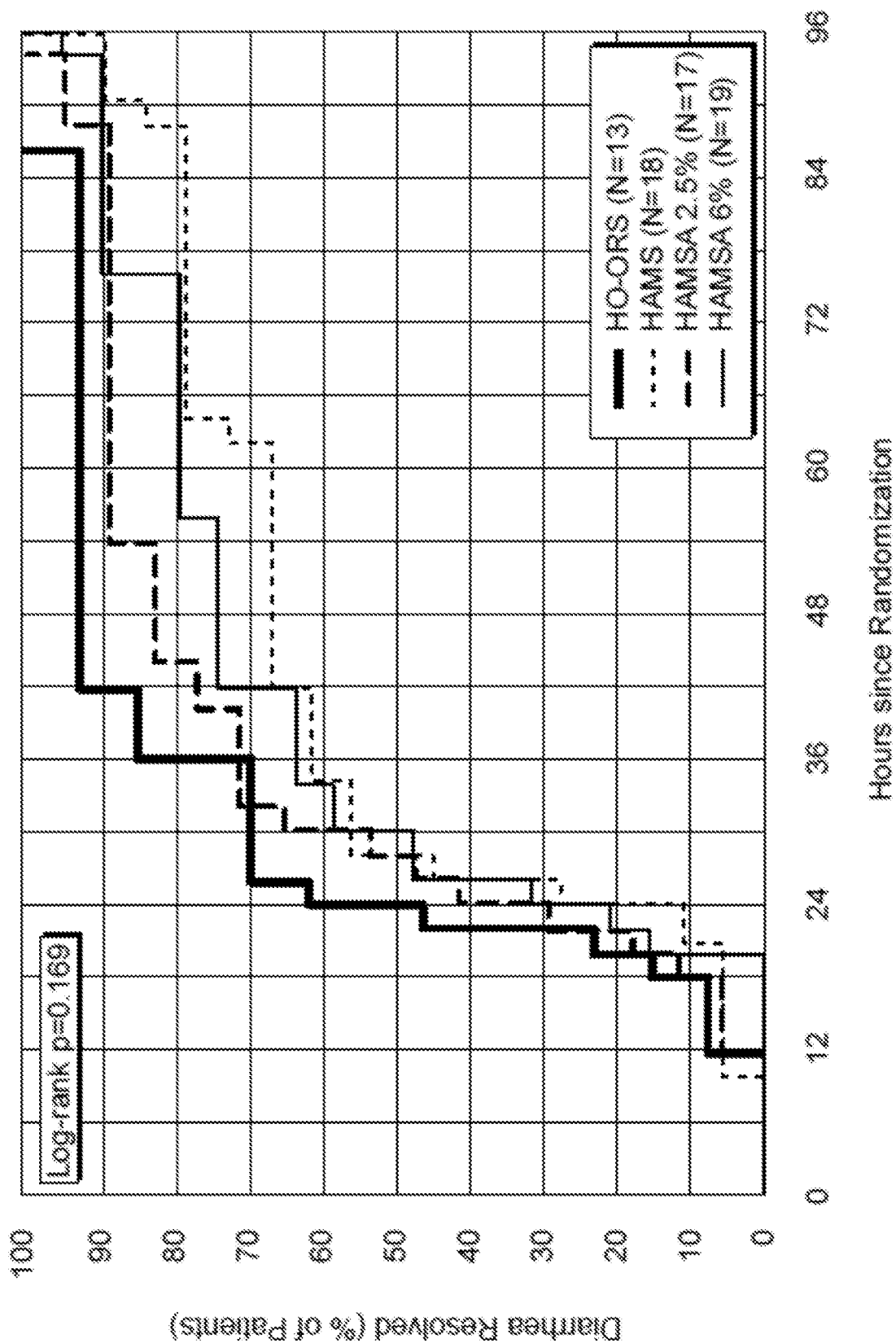
FIG. 3 shows a Kaplan-Meier plot of the duration of diarrhoea for individuals treated with either a: high amylose maize starch (HAMS); HAMS acetylated at 2.5%; HAMS acetylated at 6% or the current World Health Organisation standard oral rehydration formulation (HO-ORS).

The results of the study are shown in FIG. 3. The statistical analysis of the results are shown below in Table 15

TABLE 15

Statistical analyses for the clinical trials with various high amylose maize starches in comparison to the current WHO standard oral rehydration formulation.

| Statistic | HAMS (N = 18) | HAMS with 2.5% Acetylation (N = 17) | HAMS with 6% Acetylation (N = 19) | HO-ORS (N = 13) | Overall P-value |
|---|---|---|---|---|---|
| Mean duration of diarrhoea (hrs) | 44.9 | 35.8 | 41.3 | 30.0 | 0.262 |
| 90% Confidence Interval (CI) of Mean (hrs) | 34.9-57.7 | 27.6-46.3 | 32.3-52.7 | 22.3-40.3 | |
| Δ ORS (%) | 49.6 | 19.2 | 37.5 | — | |
| 90% CI Δ ORS (%) | 1.6-120.3% | −19.4-76.4% | 37.5-101.7% | — | |
| P-value vs ORS | 0.087 | 0.457 | 0.169 | — | |

The data shows that the formulations comprising HAMS, and the acetylated HAMS were beneficial in the treatment of diarrhoea. The overall differences were not found to be statistically significant.

It will be appreciated by persons skilled in the art that numerous variations and/or modifications may be made to the invention as shown in the specific embodiments without departing from the scope of the invention as broadly described. The present embodiments are, therefore, to be considered in all respects as illustrative and not restrictive.

The invention claimed is:

1. An oral rehydration composition for addition to water comprising:
   a salt composition;
   a fermentable acetylated type IV resistant starch in an amount of 35 g/L to 60 g/L that is acetylated to a substitution value of up to and including 2.5%, and has an amylose content of at least 70% w/w;
   xanthan gum in an amount of 1 g/L to 3 g/L to suspend the fermentable acetylated type IV resistant starch in water; and
   optionally one or more of:
   glucose;
   water soluble salts of zinc, magnesium or copper;
   sodium bicarbonate; and
   combinations thereof.

2. The oral rehydration composition according to claim 1, wherein the salt composition comprises one or more compounds selected from the group consisting of:
   sodium chloride;
   potassium chloride; and
   trisodium citrate (dihydrate).

3. The oral rehydration composition according to claim 1, wherein the oral rehydration composition comprises water soluble salts of zinc, magnesium or copper, optionally selected from the group consisting of:
   zinc acetate;
   zinc picolinate;
   zinc gluconate;
   magnesium chloride;
   copper sulphate; and
   combinations thereof.

4. An aqueous composition comprising an oral rehydration composition according to claim 1, and water, wherein the aqueous composition rehydrates an individual affected by dehydration.

5. The aqueous composition according to claim 4, wherein the dehydration is caused wholly or partially by diarrhoea, or the dehydration is caused by an individual engaging in a physical activity.

6. A method of rehydrating an individual suffering from dehydration, the method comprising a step of administering an effective amount of an oral rehydration composition to the individual, the oral rehydration composition comprising:
   water;
   a salt composition;
   a fermentable acetylated type IV resistant starch in an amount of 35 g/L to 60 g/L that is acetylated to a substitution value of up to and including 2.5%, and has an amylose content of at least 70% w/w;
   xanthan gum in an amount of 1 g/L to 3 g/L to suspend the fermentable acetylated type IV resistant starch in water; and
   optionally one or more of:
   glucose;
   water soluble salts of zinc, magnesium or copper;
   sodium bicarbonate; or
   combinations thereof.

7. The method according to claim 6, wherein the salt composition comprises one or more compounds selected from the group consisting of:
   sodium chloride;
   potassium chloride; and
   trisodium citrate (dihydrate).

8. The method according to claim 6, wherein the dehydration is caused wholly or partially by diarrhoea, or the dehydration is caused by the individual engaging in a physical activity.

9. A beverage comprising an oral rehydration composition according to claim 1 that is formulated for an individual to consume before, during or after the individual engages in a physical activity, wherein the beverage is optionally selected from the group consisting of:
   a diluted cordial drink;
   a milk based beverage;
   a smoothie;
   a protein shake; and
   a breakfast beverage.

10. The beverage according to claim 9, wherein the beverage is consumed at least 6 hours before the individual engages in the physical activity.

11. The oral rehydration composition of claim 1, wherein the fermentable acetylated type IV resistant starch is present in an amount of 45 g/L to 55 g/L.

12. The oral rehydration composition of claim 1, wherein the oral rehydration composition comprises glucose in an amount of 1 g/L to 7.5 g/L.

13. The oral rehydration composition of claim 1, wherein the oral rehydration composition comprises glucose in an amount of 1 g/L to 5 g/L.

14. The oral rehydration composition of claim 2, wherein the oral rehydration composition comprises:
   sodium chloride;
   potassium chloride; and
   trisodium citrate (dihydrate).

* * * * *

UNITED STATES PATENT AND TRADEMARK OFFICE
CERTIFICATE OF CORRECTION

PATENT NO. : 10,596,187 B2
APPLICATION NO. : 15/034965
DATED : March 24, 2020
INVENTOR(S) : Balakrishnan Siddartha Ramakrishna et al.

It is certified that error appears in the above-identified patent and that said Letters Patent is hereby corrected as shown below:

On the Title Page

Item (87), Column 1, Line 1, delete "WO2015/006767" and insert -- WO2015/066767 --

In the Specification

Column 1, Line 8, delete "2014" and insert -- 2014, --

Signed and Sealed this
Twenty-first Day of July, 2020

Andrei Iancu
*Director of the United States Patent and Trademark Office*